US005910626A

United States Patent [19]
Haselkorn et al.

[11] Patent Number: 5,910,626
[45] Date of Patent: Jun. 8, 1999

[54] ACETYL-COA CARBOXYLASE COMPOSITIONS AND METHODS OF USE

[75] Inventors: Robert Haselkorn; Piotr Gornicki, both of Chicago, Ill.

[73] Assignee: ARCH Development Corporation, Chicago, Ill.

[*] Notice: This patent is subject to a terminal disclaimer.

[21] Appl. No.: 08/422,560

[22] Filed: Apr. 14, 1995

Related U.S. Application Data

[63] Continuation-in-part of application No. 07/956,700, Oct. 2, 1992, Pat. No. 5,539,092.

[51] Int. Cl.⁶ .............................. C12N 5/00; C12N 15/00; A01H 1/04; C07H 21/04
[52] U.S. Cl. .......................... 800/205; 800/250; 435/69.1; 435/320.1; 435/172.3; 435/419; 435/252.3; 435/252.33; 435/254.2; 435/257.1; 536/23.6; 935/9; 935/67; 935/69; 935/73
[58] Field of Search ............................... 435/69.1, 172.3, 435/325, 419, 243, 320.1, 252.3, 252.33, 254.2, 257.1; 536/23.6, 23.7, 23.4, 23.1, 24.3; 800/205, 250; 935/6, 8, 9, 22, 60, 64, 66, 67, 79, 69, 73

[56] References Cited

U.S. PATENT DOCUMENTS

| | | | |
|---|---|---|---|
| 4,535,060 | 8/1985 | Comai | 435/172.3 |
| 4,757,011 | 7/1988 | Chaleff et al. | 435/172.1 |
| 4,769,061 | 9/1988 | Comai | 71/86 |
| 4,940,835 | 7/1990 | Shah et al. | 800/205 |
| 4,971,908 | 11/1990 | Kishore et al. | 435/172.1 |
| 5,162,602 | 11/1992 | Somers et al. | 800/235 |
| 5,498,544 | 3/1996 | Gengenbach et al. | 435/320.1 |
| 5,539,092 | 7/1996 | Haselkorn et al. | 536/23.2 |
| 5,559,220 | 9/1996 | Roessler et al. | 536/23.6 |

FOREIGN PATENT DOCUMENTS

| | | |
|---|---|---|
| 2048040 | 1/1992 | Canada . |
| 0068693 A2 | 5/1983 | European Pat. Off. . |
| 0 469 810 A1 | 2/1992 | European Pat. Off. . |
| 04698101 | 2/1992 | European Pat. Off. . |
| 2-057179 | 2/1990 | Japan . |
| WO93/11243 | 6/1993 | WIPO . |
| WO94/08016 | 4/1994 | WIPO . |
| WO94/17188 | 8/1994 | WIPO . |
| WO94/23027 | 10/1994 | WIPO . |
| WO94/29467 | 12/1994 | WIPO . |
| WO95/29246 | 11/1995 | WIPO . |
| WO96/31609 | 10/1996 | WIPO . |

OTHER PUBLICATIONS

Foreign Search Report dated Mar. 27, 1997.
Elborough et al., "Isolation of cDNAs from *Brassica napus* encoding the biotin–binding and transcarboxylase domains of acetyl–CoA carboxylase: assignment of the domain structure in a full–length *Arabidopsis thaliana* genomic clone," *Biochem J.*, 301:599–605, 1994; EMBL Sequence Database, Release 40, 1994, Accession Number X77382.

Egli et al., "Characterization of Maize Acetyl–Coenzyme A Carboxylase," *Plant Physiol.*, 101:499–506, 1993.
Elborough et al., "Studies on wheat acetyl CoA carboxylase and the cloning of a partial cDNA," *Plant Mol. Biol.*, 24:21–34, 1994, XP002026094.
Elborough et al., "Regulation of primary storage products of oil seeds by manipulating the level of genes involved in lipid metabolism on plant acetyl CoA carboxylase," *J. Cell. Biol.*, Supplemental 18A, p. 113, 1994, XP002026102, Abstract X1–418.
Gornicki et al., "Wheat acetyl–CoA carboxylase," *Plant Mol. Biol.*, 22:547–542, 1993, XP002026093.
Gornicki et al. "Genes for Two Subunits of Acetyl Coenzyme A Carboxylase of Anabaena sp. Strain PCC 7120: Biotin Carboxylase and Biotin Carboxyl Carrier Protein," *J. of Bacteriology*, 175(16):5268–5272, 1993; EMBL Sequence Database, Release 35, 1993, Accession Number L14862; EMBL Sequence Database, Release 35, 1993, Accession Number L14863.
Gornicki et al. "Wheat acetyl–coenzyme A carboxylase: cDNA and protein structure," *Proc. Natl. Acad. Sci.*, 91:6860–6864, 1994; EMBL Sequence Database, Release 40, 1994, Accession Number U10187.
Podkowinski et al., "Structure of a gene encoding a cytosolic acetyl–CoA carboxylase of hexaploid wheat," *Proc. Natl. Acad. Sci.*, 93(5):1870–1874, 1996, ISSN:0027–8424, XP002026103; EMBL Sequence Database, Release 47, Accession Number U39321, 1996.
Phung et al., "Genes for Fatty Acid Biosynthesis in the Cyanobacterium Synechococcus sp. strain PCC 7942," *95th General Meeting of the American Society for Microbiology*, May 21–25, 1995, Abstract H–182, ISSN:1060–2011, XP000601370.
Roesler et al., "Structure and Expression of an Arabidopsis Acetyl–Coenzyme A Carboxylase Gene," *Plant Physiol*, 105:611–617, 1994 (XP 002013209).
Valentin et al., "Glutamate synthase is plastid–encoded in a red alga: Implications for the evolution of glutamate synthases," *Plant Mol. Biol.* 23:77–85, 1993; EMBL Sequence Database Release 39, 1994, Accession Number Z33874, XP002026098.
Slabas et al., "Rapid purification of a high molecular weight subunit polypeptide form of rape seed acetyl CoA carboxylase," *Plant Science*, 39:177–182, 1985.
Winz et al., "Unique structural features and differential phosphorylation of the 280–kDa component (isozyme) of rat liver acetyl–CoA carboxylase," *J. Biol. Chem.* 269(20):14438–14445, 1994, XP002026101.

(List continued on next page.)

*Primary Examiner*—Bruce R. Campell
*Attorney, Agent, or Firm*—Arnold White & Durkee

[57] ABSTRACT

The present invention provides isolated and purified polynucleotides that encode plant and cyanobacterial polypeptides that participate in the carboxylation of acetyl-CoA. Isolated cyanobacterial and plant polypeptides that catalyze acetyl-CoA carboxylation are also provided. Processes for altering acetyl-CoA carboxylation, increasing herbicide resistance of plants and identifying herbicide resistant variants of acetyl-CoA carboxylase are also provided.

52 Claims, 7 Drawing Sheets

OTHER PUBLICATIONS

Sasaki et al., "Chloroplast–encoded protein as a subunit of acetyl–CoA carboxylase in pea plant," *J. Biol. Chem.* 268(33):25118–25123, 1993, XP002013210.

Abu–Elheiga, Lutfi, et al., "Human acetyl–CoA carboxylase: Characterization, molecular cloning, and evidence for two isoforms", *Proc. Natl. Acad. Sci. USA*, 92:4011–4015, Apr. 1995.

Egli, Margaret A., et al., "A Maize Acetyl–Coenyme A Carboxylase cDNA Sequence", *Plant Physiol.*, 108:1299–1300, 1995.

Fu, Hongyong, et al., "High–Level Tuber Expression and Sucrose Inducibility of a Potato Sus4 Sucrose Synthase Gene Require 5' and 3' Flanking Sequences and the Leader Intron", *The Plant Cell*, 7:1387–1394, Sep. 1995.

Gornicki, P., et al., "Wheat acetyl–coenzyme A carboxylase: cDNA and protein structure", *Proc. Natl. Acad. Sci. USA*, 91:6860–6864, Jul. 1994.

Norman, Elizabeth, et al., "Lipid Synthesis in Mycobacteria: Characterization of the Biotin Carboxyl Carrier Protein Genes from *Mycobacterium leprae* and *M. tuberculosis*", *Journal of Bacteriology*, 176(9):2525–2531, May 1994.

Page, Rachel A., et al., "Acetyl–CoA carboxylase exerts strong flux control over lipid synthesis in plants", *Biochimica et Biophysica Acta*, 1210:369–372, 1994.

Shorrosh, Basil S., et al., "Molecular cloning, characterization, and elicitation of acetyl–CoA carboxylase from alfalfa", *Proc. Natl. Acad. Sci. USA*, 91:4323–4327, May 1994.

Weaver, Lisa M., et al., "Molecular Cloning of the Biotinylated Subunit of 3–Methylcrotonyl–Coenzyme A Carboxylase of *Arabidopsis thaliana*", Plant Physiol., 107:1013–1014, 1995.

Winz, Robert, et al., "Unique Structural Features and Differential Phosphorylation of the 280–kDa Component (Isozyme) of Rat Liver Acetyl–CoA Carboxylase", *The Journal of Biological Chemistry*, 269(2)14438–14445, 1994.

Yanai, Yukihiro, et al., "Genomic Organization of 251 kDa Acetyl–CoA Carboxylase Genes in Arabidopsis: Tandem Gene Duplication has Made Two Differentially Expressed Isozymes", *Plant Cell Physiol.*, 36(5):779–787, 1995.

Aebersold et. al, Internal amino acid sequence analysis of protiens separated by one or two–dimensional gel electrophoresis after in situ protease, *Proc. Natl. Acad. Sci. USA* 84:6970–6974, 1987.

Al–Feel et. al, Cloning of the yeast FAS3 gene and primary structure of yeast acetyl–CoA carboxylase, *Proc. Natl. Acad. Sci. USA*, 89:4534–4538, 1992.

Alix, Laboratory Methods; A Rapid Procedure for Cloning Genes from λ Libraries by Complementation of *E. coli* Defective Mutants: Application to the fabE Region of the *E. coli* Chromosome, *DNA* 8:(10)779–789, 1989.

Bai et. al, Analysis of the biotin–binding site on acetyl–CoA carboxylase from rat, *Eur. J. Biochem.* 182:239–245, 1989.

Buhler et. al, Improved Purification and Further Characterization of Acetyl–CoA Carboxylase from Cultured Cells of Parsley (*Petroselinum hortense*) *Eur. J. Biochem.* 133:335–339, 1983.

Craig et. al, Genetic engineering of micro–algae, Micro–Algal Biotechnology Cambridge University Press, 16:415–455, 1988.

Eichholtz et. al, Expression of Mouse Dihydrofolate Reductase Gene Confers Methotrexate Resistance in Transgenic Petunia Plants, *Somatic Cell and Molecular Genetics*, 13:(1)67–76, 1987.

Evenson et. al, Purification and Characterization of Acetyl–CoA Carboxylase from Diclofop–Resistant and Susceptible Italian Ryegrass (*Lolium Multiflorum*), *Plant Physiol*, 99(1 Suppl):59, Abstract #351, 1992.

Golden, Genetic Engineering of the cyanobacterial Chromosome, *J. Bacteriol*, 165:(964)215–231, 1986.

Guchhait et.al, Acetyl Coenzyme A Carboxylase System of *Escherichia coli*, *J. Biol. Chem.* 249:(20)6633–6645, 1974.

Harwood, Fatty Acid Metabolism, *Ann. Rev. Plant Physiol. Plant Mol. Biol.*, 39:101–138, 1988.

Harwood, Medium and Long–Chain Fatty Acid Synthesis in, The Metabolism, Structure, and Function of Plant Lipids, Edited by: Stumpf et. al, 465–472.

Haymerle et.al, Efficient construction of cDNA libraries in plasmid expression vectors using an adaptor strategy, *Nucleic Acids Research*, 14:(21)8615–8624, 1986.

Jaye et. al, Isolation of a human anti–haemophilic factor IX cDNA clone using a unique 52–base synthetic oligonucleotide probe deduced from the amino acid sequence of bovine factor IX, *Nucleic Acids Research* 11:(8)2325–2335, 1983.

Knowles, The Mechanism of Biotin–Dependent Enzymes, *Annu. Rev. Biochem.* 58:195–221, 1989.

Kondo et. al, Acetyl–CoA carboxylase from *Escherichia coli*: Gene organization and nucleotide sequence of the biotin carboxylase subunit, *Proc. Natl. Acad. Sci. USA* 88:9730–9733, 1991.

Lamppa et. al, Structure and Developmental Regulation of a Wheat Gene Encoding the Major Chlorophyll a/b–BInding Polypeptide, *Mole. Cell. Bio.*, 5:(6)1370–1378, 1985.

Li et.al, The Gene Encoding the Biotin Carboxylase Subunit of *Escherichia coli* Acetyl–CoA Carboxylase, *J. Biol. Chem.*, 267:(2)855–863, 1992.

Lichtenthaler, Mode of Action of Herbicides Affecting Acety;–CoA Carboxylase and Fatty Acid Biosynthesis, *Z. Naturforsch*, 45c:521–528, 1990.

Livine et. al, Acetyl–Coenzyme A Carboxylase from the Marine Prymnesiophyte *Isochrysis glabana*, *Plant Cell Physiol*, 31:(6)851–858, 1990.

Lopez–Casillas et. al, Structure of the coding sequence and primary amino acid sequence of acetyl–coenzyme A carboxylase, *Proc. Natl. Acad. Sci. USA*, 85:5784–5788, 1988.

Lopez–Casillas et. al, Heterogeneity at the 5' End of Rat Acetyl–coenzyme A Carboxylase mRNA, *J. Biological Chem.*, 264:(13)7176–7184, 1989.

Luo et. al, Structural features of the acetyl–CoA carboxylase gene: Mechanisms for the generation of mRNAs with 5' end heterogeneity, *Proc. Natl. Acad. Sci. USA*, 86:4042–4046, 1989.

Muramatsu et. al, Nucleotide sequence of the fabE gene and flanking regions containing a bent DNA sequence of *Escherichia coli*, *Nucleic Acids Research*, 17:(10)3982, 1989.

Palosarri et. al, Comparison of Acetyl–Coenzyme A Carboxylase From Graminicide–Tolerant and Susceptible Maize Lines, *Plant Physiol.*, 99(1Suppl):59, Abstract #352, 1992.

Pecker et. al, A single polypeptide catalyzing the conversion of phytoene to ζ–carotene is transcriptionally regulated during tomato fruit ripening, *Proc. Natl. Acad. Sci. USA*, 89:4962–4966, 1992.

Post–Beittenmiller et. al, In Vivo Pools of Free and Acylated Acyl Carrier Proteins in Spinach, *J. Biol. Chem.*, 266:(3)1858–1865, 1991.

Roessler et. al, Characterization of the Gene for Acetyl–CoA Carboxylase From the Alga *Cyclotella Cryptica*, *Plant Physiol.*, 99(1 Suppl):19 Abstract #113, 1992.

Roessler et. al, Purification and Characterization of Acetyl––CoA Carboxylase from the Diatom *Cyclotella cryptica*, *Plant Physiol.*, 92:73–78, 1990.

Samols et. al, Evolutionary Conservation among Biotin Enzymes, *J. Biol. Chem.*, 263:6461–6464, 1988.

Slabas et. al, Rapid Purification of a High Molecular Weight Subunit Polypeptide Form of Rape Seed Acetyl CoA Carboxylase, *Plant Science*, 39:177–182, 1985.

Sedlak, Iowa State Scientists Clone A Key Plant Oil Production Gene, *Genetic Engineering News*, May 1991.

Takai et. al, Primary Structure of Chicken Liver Acetyl–CoA Carboxylase Deduced from cDNA Sequence, *J. Biol. Chem.*, 263:(6)2651–2657, 1988.

Vasil et. al, Herbicide Resistant Fertile Transgenic Wheat Plants Obtained By Microprojectile Bombardment of Regenerable Embryogenic Callus, *Bio/Technology*, 10:667–674, 1992.

Wurtele et. al, Plants Contain Multiple Biotin Enzymes: Discovery of 3–Methylcrotonyl–CoA Carboxylase, Propionyl–CoA Carboxylase and Pyruvate Carboxylase in the Plant Kingdom,*Archives of Biochemistry and Biophysics*, 278:(1)179–186, 1990.

Slabas et al., "The Biochemistry and Molecular Biology of Plant Lipid Biosynthesis," *Plant Molecular Biology*, 19:169–191, 1992.

Egin–Buehler et al., "Comparison of Acetyl Coenzyme A Carboxylases (ED 6.4.1.2) From Parsley (Petroselinum Hortense) Cell Cultures and Wheat Germ," *Arch Biochem Biophys.*, 203(1):90–100, 1980 (Abstract).

Egli et al., "A 223 kDa Subunit of Acetyl–CoA Carboxylase is Encoded by the Accl Gene," *Maize Genetics Cooperation Newsletter*, 66:94–95, 1992.

Egli et al., "Purification of Maize Leaf Acetyl–CoA Carboxylase," *Maize Genetics Cooperaton Newsletter*, 65:95, 1991.

Egli et al., "Purification and Characterization of Maize Acetyl–CoA Carboxylase," *Plant Physiology*, 96(1):92(581), 1991.

Gornicki et al., "Genes for Two Subunits of Acetyl Coenzyme A Carboxylase of Anabaena sp. Strain PCC 7120: Biotin Carboxylase and Biotin Carboxyl Carrier Protein," *Journal of Bacteriology*, 175(16):5268–5272, 1993.

Nicolau et al., "Use of Streptavidin to Detect Biotin–Containing Proteins in Plants," *Anal Biochem.*, 149(2):448–453, 1985.

International Search Report, Mailed Feb. 22, 1994.

Alban et al., "Purification and characterization of 3–methylcrotonyl–coenzyme A carboxylase from higher plant mitochondria," *Plant. Physiol.*, 102:957–965, 1993.

Best, E.A., and Knauf, V.C., "Organization and nucleotide sequence of the genes encoding the biotin carboxyl carrier protein and biotin cargboxylase protein of *Pseudomonas aeruginosa* acetyl coenzyme a carboxylase," *J. Bacteriol.*, 175:6881–6889, 1993.

Bettey et al., "Purification and characterization of acetyl–coA carboxylase from developing pea embryos," *J. Plant. Physiol.*, 140:513–520, 1992.

Browner et al., "Sequence analysis, biogenesis and mitochonoriald import of the alpha–subunit of rat liver propionyl–CoA carboxylase," *J. Biol. Chem.*, 264:12680–12685.

Chen et al., Purification and characterization of 3–methylocrotonyl–CoA carboxylase from somatic embryos of Dacuscarota., *Arch. Biochem. Biophys.*, 305:103–109, 1993.

Chirala, S.S., "Coordinated regulation and inositol–mediated and fatty acid–mediaed repression of fatty acid synthase genes in *Saccharomyces cerevisiae*," *proc. Natl. Acad. Sci. USA*, 89:10232–10236, 1992.

Egin–Buhler, B. and Ebel, J., "Comparison of acetyl–CoA carboxylase from parsley cell culture and from wheat germ," *Eur J. Biochem.*, 133:335–339, 1983.

Egli et al., "Characterization of maize acetyl–coenzyme A carboxylase," *Plant. Physiol.*, 101:499–506, 1993.

Fall, R.R., "Analysis of microbiol biotin proteins," *Meth. Enzymol.*, 62:390–398, 1979.

Gornicki, P. and Haselkorn, R., "Wheat acetyl–CoA carboxylase," *Plant Mol. Biol.* 22:547–552, 1993.

Hardie et al., "The AMP–activated protein kinase: a multisubstrate regulator of lipid metabolism," *Trends in Biochem. Sci.*, 14:20–23, 1989.

HaBlacher et al., "Acetyl–CoA carboxylase from yeast is an essential cnzyme and is regulated by factors that control phospholipid metabolism," *J. Biol. Chem.*, 268:10946–10952, 1993.

Holt et al., "Mechanisms and agronomic aspects of herbicide resistance," *Annu. Rev. Plant. Physiol. Plant Mol. Biol.*, 44:203–229, 1993.

Li, S–1 and Cronan, J.E., Growth rate regulation of *Escherichiacoli* acetyl coenzyme A carboxylase, which catalyzes the first commited step of lipid biosynthesis, *J. Bacteriol.*, 175:332–340, 1993.

Marshall et al., "Allelic mutations in acetyl–coenzyme A carboxylse confer herbicide tolerance in maiz," *Theor. Appl. Genet.*, 83:435–442, 1992.

Nikolau et al., "Acetyl–coenzyme A carboxylase in maize leaves," *Arch. Biochem. and Biophys.*, 211:605–612, 1981.

Nikolau et al., "Tissue distribution of ACC in leaves," *Plant Physiol.*, 75:895–901, 1984.

Post–Beittenmiller et al., "Regulation of plant fatty acid biosynthesis," *Plant. Physiol.*, 100:923–930, 1992.

Reitzel, L. and Nielsen, N.C., "Acetyl–coenzyme A carboxylase during development of plastides in wild–type and mutant barley seedlings," *Eur. J. Biochem.*, 65:131–138, 1976.

Rendina et al., "Kinetic characterization , stereoselectivity and species selectivity of the inhibition of plant acetyl–CoA carboxylase by the aryloxyphenoxypropionic acid grass herbicides," *Arch. Biochem. Biophys.*, 265:219–225, 1988.

Roessler, P.G. and Ohlrogge, J.B., "Cloning and characterization of the gene that encodes acetyl–coenzyme A carboxylase in the alga *Cyclotellacryptica*," *J. Biol. Chem.*, 268:19259, 1993.

Sasaki et al., "Chloroplast–edcloded protein as a subunit of acetyl–CoA carboxylase in pea plant," *J. Biol. Chem.*, 268:25118–25123, 1993.

Shenoy et al., "The importance of methonine residues for the catalysis of the biotin enzyme, transcarboxylase," *J. Biol. Chem.*, 18407–18412, 1992.

Slabas, A.R., and T. Fawcett, "The biochemistry and molecular biology of plant lipid biosynthesis," *Plant. Mol. Biol.*, 19:169–191, 1992.

Somers et al., "Expression of the Accl gene–encoded acetyl–coenzyme A carboxylase in developing maize (*Zea mays L.*) kernels," *Plant Physiol*, 101:1097–1101, 1993.

Somerville, A. and Browse, J., "Plant lipids: metabolism, mutants, and membranes," *Science*, 252:80–87, 1991.

Toh et al., "Molecular evolution of biotin–dependent carboxylases," *Eur. J. Biochem.*, 215:687–696, 1993.

Turnham, E., and Northcote, D.H., "Changes in the activity of acetyl–CoA carboxylase during rape–see formation," *Biochem. J.*, 212:223–229, 1983.

Witters, L.A., and Kemp, B.E., "Insulin activation of acetyl–CoA carboxylase by inhibition of the 5'–AMP–activated protein kinase," *J. Biol. Chem.*, 267:2864–2867, 1992.

Wood, H.G., and Barden, R.E., "Biotin enzymes," *Ann. Rev. Biochem.*, 46:385–413, 1977.

Wurtele, E.S., and Nikolau, B.J., "Differential accumulation of biotin enzymes during carrot somatic embryogenesis," *Plant. Physiol.* 99:1699–1703, 1992.

Al–Feel et al., "Cloning of the yeast FAS3 gene and primary structure of yeast acetyl–CoA carboxylase," *Proc. Natl. Acad. Sci. USA*, 89:4534–4538, May 1992.

Aston et al., "Molecular cloning of two different cDNAs for maize acetyl CoA carboxylase," *Plant Molecular Biology*, 24:35–49, 1994.

Best and Knauf, "Organization and Nucleotide Sequences of the Genes Encoding the Biotin Carboxyl Carrier Protein and Biotin Carboxylase Protein of *Pseudomonas aeruginosa* Acetyl Coenzyme A Carboxylase," *Journal of Bacteriology*, 175(21):6881–6889, Nov. 1993.

Bettey et al., "Purification and Characterization of Acetyl CoA Carboxylase from Developing Pea Embryos," *J. Plant Physiol.*, 140:513–520, 1992.

Bowness et al., "Conservation of T cell receptor usage by HLA B24–resitricted influenza–specific cytotoxic T lymphocytes suggests a general pattern for antigen–specific major histocompatibility complex class I–restricted responses," *Eur. J. Immunol.*, 23:1417–1421, 1993.

Brichard et al., "The Tyrosinase Gene Codes for an Antigen Recognized by Autologous Cytolytic T Lymphocytes on HLA–A2 Melanomas," *J. Exp. Med.*, 178:489–495, Aug. 1993.

Egin–Bühler et al., "Comparison of Acetyl–CoA Carboxylases from Parsley Cel Cultures and Wheat Germ," *Archives of Biochemistry and Biophysics*, 203(1):90–100, Aug. 1980.

Egin–Bühler and Ebel, Improved Purification and Further Characterization of Acetyl–CoA Carboxylase from Cultured cells of Parsley (*Petroselinum hortense*), *Eur. J. Biochem.*, 133:335–339, 1983.

Egli et al., "Characterization of Maize Acetyl–Coenzyme A Carboxylase," *Plant Physiol.*, 101:499–506, 1993.

Elborough et al., "Studies on wheat acetyl CoA carboxylase and the cloning of a partial cDNA," *Plant Molecular Biology*, 24:21–34, 1994.

Fernandez and Lamppa, "Acyl Carrier Protein Import into Chloroplasts," *The Journal of Biological Chemistry*, 266(11):7220–7226, Apr. 1991.

Fraley et al., "The SEV System: A New Disarmed TI Plasmid Vector System for Plant Transformation," *Bio/Technology*, 3:629–635, Jul. 1985.

Fraley et al., "Expression of bacterial genes in plant cells," *Proc. Natl. Acad. Sci. USA*, 80:4803–4807, Aug. 1983.

Gornicki and Haselkorn, "Wheat acetyl–CoA carboxylase," *Plant Molecular Biology*, 22:547–552, 1993.

Gornicki et al., "Genes for Two Subunits of Acetyl Coenzyme A Carboxylase of *Anabaena* sp. Strain PCC 7120:Biotin Carboxylase and Biotin Carboxyl Carrier Protein," *Journal of Bacteriology*, 175(16):5268–5272, Aug. 1993.

Ha et al., "Critical Phosphorylation Sites for Acetyl–CoA Carboxylase Activity," *The Journal of Biological Chemistry*, 269(35):22162–22168, Sep. 1994.

Ha et al., "Cloning of human acetyl–CoA carboxylase cDNA," *Eur. J. Biochem.*, 219:297–306, 1994.

Hasslacher et al., "Acetyl–CoA Carboxylse from Yeast Is an Essential Enzyme and Is Regulated by Factors That Control Phospholipid Metabolism," *The Journal of Biological Chemistry*, 268(15):10946–10952, May 1993.

Holt et al., "Mechanism and Agronomic Aspects of Herbicide Resistance," *Annu. Rev. Plant Physiol. Plant Mol. Biol.*, 44:203–229, 1993.

Hu et al., "An Evaluation of the Potential to Use Tumor––associated Antigens as Targets for Antitumor T Cell Therapy Using Transgenic Mice Expressing a Retroviral Tumor Antigen in Normal Lymphoid Tissues," *J. Exp. Med.*, 177:1681–1690, Jun. 1993.

Huffman et al., "Optimizing Plant Expression Vectors," *Journal of Cellular Biochemistry*, ABSTRACT A434, Jan. 1991.

Klein et al., "High–velocity microprojectiles for delivering nucleic acids into living cells," *Nature*, 327:70–73, May 1987.

Klein et al., "Genetic Transformation of Maize Cells by Particle Bombardment," *Plant Physiol.*, 91:440–444, May 1989.

Klein et al., "Stable genetic transformation of intact Nicotiana cells by the particle bombardment process," *Proc. Natl. Acad. Sci. USA*, 85:8502–8505, Nov. 1988.

Kondo et al., "Acetyl–CoA carboxylase from *Escherichia coli*: Gene organization and nucleotide sequence of the biotin carboxylase subunit," *Proc. Natl. Acad. Sci. USA*, 88:9730–9733, Nov. 1991.

Li and Cronan, "Growth Rate Regulation of *Escherichia coli* Acetyl Coenzyme A Carboxylase, Which Catalyzes the First Committed STtep of Lipid Biosynthesis," *Journal of Bacteriology*, 175(2):332–340, Jan. 1993.

Li and Cronan, "Putative zinc finger protein encoded by a conserved chloroplast gene is very likely a subunit of a biotin–depenedent carboxylase," *Plantn Molecular Biology*, 20:759–761, 1992.

Li and Cronan, "The Gene Encoding the Biotin Carboxylase Subunit of *Escherichia coli* Acetyl–CoA Carboxylase," *The Journal of Biological Chemistry*, 267(2):855–863, Jan. 1992.

Lichtenthaler, "Mode of Action of Herbicides Affecting Acety–CoA Carboxylase and Fatty Acid Biosynthesis," *Z. Naturforsch.*:521–528, Dec. 2, 1989.

Lòpez–Casillas et al., "Structure of the coding sequence and primary amino acid sequence of acetyl–coenzyme A carboxylase," *Proc. natl. Acad. Sci. USA*, 85:5784–578, Aug. 1988.

Luo et al., "Molecular cloning and analysis of a cDNA coding for the bifunctional dihydrofolate reductase–thymidylate synthase of Daucuscarota," *Plant Molecular Biology*, 22:427–435, 1993.

Luo et al., "Structural features of the acetyl–CoA carboxylase gene: Mechanisms for the generation of mRNAs with 5' end heterognenity," *Proc. Natl. Acad. Sci. USA*, 86:4042–4046, Jun. 1989.

Marshall et al., "Allelic mutations in acetyl–coenzyme A carboxylase confer herbicide tolerance in maize," *Theor Appl Genet*, 83:435–442, 1992.

Muramatsu and Mizuno, "Nucleotide sequence of the fabE gene and flanking regions containing a bent DNA sequence of *Escherichia coli*," *Nucleic Acids Research*, 17(10):3982, 1989.

Omirulleh et al., "Activity of a chimeric promoter with the doubled CaMV 35S enhancer element in protoplast–derived cells and transgenic plants in maize," *Plant Molecular Biology*, 21:415–428, 1993.

Roessler and Ohlrogge, "Cloning and Characterization of the Gene That Encodes Acetyl–coenzyme A Carboxylase in the Alga *Cyclotella cryptica*," *The Journal of Biological Chemistry*, 268(26), 19254–19259, Sep. 1993.

Samols et al., "Evolutionary Conservation among Biotin Enzymes," *The Journal of Biological Chemistry*, 263(14):6461–6464, May 1988.

Sasaki et al., "Chloroplast–encoded Protein as a Subunit of Acetyl–CoA Carboxylase in Pea Plant," *The Journal of Biological Chemistry*, 268(33):25118–15123, Nov. 1993.

Schneider and Haselkorn, "RNA Polymerase Subunit Homology among Cyanobacteria, Other Eubacteria, and Archaebacteria," *Journal of Bacteriology*, 170(9):4136–4140, Sep. 1988.

Slabas and Hellyer, "Rapid Purification of a High Molecular Weight Subunit Polypeptide Form of Rape Seed Acetyl CoA Carboxylase," *Plant Science*, 39:177–182, 1985.

Somers et al., "Expression of the Accl Gene–Encoded Acetyl–Coenzyme A Carboxylase in Developing Maize (*Zea mays L.*) Kernels," *Plant Physiol.*, 101:1097–1101, 1993.

Toh et al., "Molecular evolution of biotin–dependent carboxylases," *Eur. J. Biochem.*, 215:687–696, 1993.

Wurtele and Nikolau, "Plants Contain Multiple Biotin Enzymes: Discovery of 3–Methylcrotonyl–CoA Carboxylase, Propionyl–CoA Carboxylase and Pyruvate Carboxylase in the Plant Kingdom," *Archives of Biochemistry and Biophysics*, 278(1):179–186, Apr. 1990.

HG Tomasiewicz et al (1987) J Bacteriol 169: 5735–5744.

F Lopez–Casillas et al (1988) Proc Natl Acad Sci USA 85:5784–5788.

H Kondo et al (1991) Proc Natl Acad Sci USA 88: 9730–9733.

B Guss et al (1984) Eur J Biochem 138: 413–420.

D Holland et al (1990) J Bacteriol 172: 3131–3137.

H Suzuki et al (1987) Biochem Biophys Res Comm 146: 403–409.

V Gamulin et al (1983) Nucleic Acids Research 11: 8537–8546.

W Pansdegrau et al (1987) Plasmid 18: 193–204.

T Konishi et al (1994) Proc Natl Acad Sci USA 91: 3598–3601.

WJ Gordon–Kamm et al (1990) Plant Cell 2: 603–618.

ACETYL-CoA CARBOXYLASE COMPOSITIONS AND METHODS OF USE

BACKGROUND OF THE INVENTION

The present application is a continuation-in-part of U.S. Ser. No. 07/956,700, filed Oct. 2, 1992, issued Jul. 23, 1996 as U.S. Pat. No. 5,539,092; the entire text and figures of which disclosure are specifically incorporated herein by reference without disclaimer.

The United States government has certain rights in the present invention pursuant Grant #90-34190-5207 from the United States Department of Agriculture.

A. FIELD OF THE INVENTION

The present invention relates to the field of enzymes. More specifically, it concerns cyanobacterial and plant acetyl-CoA carboxylase (ACC) compositions and methods for making and using ACC-encoding polynucleotides and ACC polypeptides.

B. DESCRIPTION OF THE RELATED ART

1. Acetyl-CoA Carboxylase

Acetyl-CoA carboxylase (ACC) catalyzes the first committed step in de novo fatty acid biosynthesis, the addition of $CO_2$ to acetyl-CoA to yield malonyl-CoA. It belongs to a group of carboxylases that use biotin as cofactor and bicarbonate as a source of the carboxyl group. ACC catalyzes the addition of $CO_2$ to acetyl-CoA to yield malonyl-CoA in two steps as shown below.

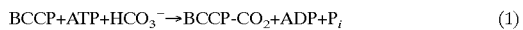
$$BCCP + ATP + HCO_3^- \rightarrow BCCP\text{-}CO_2 + ADP + P_i \quad (1)$$

$$BCCP\text{-}CO_2 + \text{Acetyl-CoA} \rightarrow BCCP + \text{malonyl-CoA} \quad (2)$$

First, biotin becomes carboxylated at the expense of ATP. The carboxyl group is then transferred to Ac-CoA (Knowles, 1989). This irreversible reaction is the committed step in fatty acid synthesis and is a target for multiple regulatory mechanisms. Reaction (1) is catalyzed by biotin carboxylase (BC); reaction (2) by transcarboxylase (TC); BCCP=biotin carboxyl carrier protein.

There are two types of ACC: prokaryotic ACC in which the three functional domains: biotin carboxylase (BC), biotin carboxyl carrier protein (BCCP) and carboxyltransferase (CT) are located on separable subunits (e.g., E. coli, P. aeruginosa, Anabaena, Synechococcus and probably pea chloroplast) and eukaryotic ACC in which all the domains are located on one large polypeptide (e.g., rat, chicken, yeast, diatom and wheat).

E. coli ACC consists of a dimer of 49-kDa BC monomers, a dimer of 17-kDa BCCP monomers and a CT tetramer containing two each of 33-kDa and 35-kDa subunits. The primary structures of all of the E. coli ACC subunits (Alix, 1989; Muramatsu and Mizuno, 1989; Kondo et al., 1991; Li and Cronan, 1992; Li and Cronan, 1992) as well as the structure of the BC and BCCP of Anabaena 7120 (Gornicki et al., 1993), and P. aeruginosa (Best and Knauf, 1993) are known, based on the gene sequences. The genes encoding the subunits of E. coli ACC are called: accA (CT α subunit), accB (BCCP), accC (BC) and accD (CT β subunit). accC and accB form one operon, while accA and accD are not linked to each other or to accCB (Li and Cronan, 1992). In cyanobacteria, accC and accB are unlinked as well (Gornicki et al., 1993).

Yeast, rat, chicken and human ACCs are cytoplasmic enzymes consisting of 250- to 280-kDa subunits while diatom ACC is most likely a chloroplast enzyme consisting of 230-kDa subunits. Their primary structure has been deduced from cDNA sequences (Al-feel et al., 1992; Lopez-Casillas et al., 1988; Takai et al., 1988; Roessler and Ohlrogge, 1993; Ha et al., 1994). In eukaryotes, homologs of the four bacterial genes are fused in the following order: accC, accB, accD and accA. Animal ACC activity varies with the rate of fatty acid synthesis or energy requirements in different nutritional, hormonal and developmental states. In the rat, ACC mRNA is transcribed using different promoters in different tissues and can be regulated by alternative splicing. The rat enzyme activity is also allosterically regulated by a number of metabolites and by reversible phosphorylation (Ha et al., 1994 and references therein). The expression of the yeast gene was shown to be coordinated with phospholipid metabolism (Chirala, 1992; Haslacher et al., 1993).

Much less is known relating to plant ACC. Early attempts at characterization of plant ACC led to the suggestion that it consisted of low molecular weight subunits similar to those of bacteria (Harwood, 1988). More recent efforts indicate that at least one plant isozyme is composed of >200-kDa subunits, similar to the enzyme from other eukaryotes (Egin-Buhler and Ebel, 1983; Slabas and Hellyer, 1985; Gornicki and Haselkorn, 1993; Egli et al., 1993; Betty et al., 1992).

While strong evolutionary conservation exists among biotin carboxylases and biotin carboxylase domains of all biotin-dependent carboxylases, BCCP domains show very little conservation outside the conserved sequence E(A/V) MKM (lysine residue is biotinylated) (Knowles, 1989; Samols et al., 1988). Although the three functional domains of the E. coli ACC are located on separate polypeptides, plant ACC is quite different, having all 3 domains on a single polypeptide.

At least one form of plant ACC is located in plastids, the primary site of fatty acid synthesis. The gene encoding it, however, must be nuclear because no corresponding sequence has been seen in the complete chloroplast DNA sequences of tobacco, liverwort or rice. The idea that in some plants plastid ACC consisted of several smaller subunits was revived by the discovery of an accD homolog in some chloroplast genomes (Li and Cronan, 1992). Indeed, it has been shown that the product of this gene in pea binds two other peptides, one of which is biotinylated. The complex may be a chloroplast isoform of ACC in pea and some other plants (Sasaki et at., 1993).

2. Genes Encoding ACC

Plant genes encoding eukaryotic-type plastid ACC are nuclear-encoded, since no corresponding sequences have been identified in the complete chloroplast DNA sequences of tobacco, liverwort or rice. ACC, like the vast majority of chloroplast proteins which are encoded in nuclear DNA, most probably is synthesized in the cytoplasm and then transported into the chloroplast, presumably requiring a chloroplast transport sequence. Although the basic features of plant ACC are the same as those of prokaryotic and other eucaryotic ACCs, significant differences may also be expected due, for example, to differences in plant cell metabolism and ACC cellular localization.

The possibility of different ACC isoforms, one present in plastids and another in the cytoplasm, is now accepted. The rationale behind the search for a cytoplasmic ACC isoform is the requirement for malonyl-CoA in this cellular compartment, where it is used in fatty acid elongation and synthesis of secondary metabolites. Indeed, two isoforms were found in maize, both consisting of >200-kDa subunits but differing in size, herbicide sensitivity and immunological properties. The major form was found to be located in mesophyll chloroplasts. It is also the major ACC in the endosperm and in embryos (Egli et al., 1993).

3. Herbicide Resistance

Although the mechanisms of inhibition and resistance are unknown (Lichtenthaler, 1990), it has been shown that aryloxyphenoxypropionates and cyclohexane-1,3-dione derivatives, powerful herbicides effective against monocot weeds, inhibit fatty acid biosynthesis in sensitive plants.

The aryloxyphenoxypropionate class comprises derivatives of aryloxyphenoxypropionic acid such as diclofop, fenoxaprop, fluazifop, haloxyfop, propaquizafop and quizalofop. Several derivatives of cyclohexane-1,3-dione are also important post-emergence herbicides which also selectively inhibit monocot plants. This group comprises such compounds as oxydim, cycloxydim, clethodim, sethoxydim, and tralkoxydim.

Recently it has been determined that ACC is the target enzyme for both of these classes of herbicide at least in monocots. Dicotyledonous plants, on the other hand, such as soybean rape, sunflower, tobacco, canola, bean, tomato, potato, lettuce, spinach, carrot, alfalfa and cotton are resistant to these compounds, as are other eukaryotes and prokaryotes.

Important grain crops, such as wheat, rice, maize, barley, rye, and oats, however, are monocotyledonous plants, and are therefore sensitive to these herbicides. Thus herbicides of the aryloxyphenoxypropionate and cyclohexane-1,3-dione groups are not useful in the agriculture of these important grain crops owing to the inactivation of monocot ACC by such chemicals.

4. Cyanobacteria

Unlike monocot plants, members of the cyanobacteria are resistant to these herbicide families. Cyanobacteria are prokaryotes that carry out green plant photosynthesis, evolving $O_2$ in the light. They are believed to be the evolutionary ancestors of chloroplasts. Virtually nothing is known about fatty acid biosynthesis in cyanobacteria.

Synechococcus is a unicellular obligate phototroph with an efficient DNA transformation system. Replicating vectors based on endogenous plasmids are available, and selectable markers include resistance to kanamycin, chloramphenicol, streptomycin and the PSII inhibitors diuron and atrazine. Inactivation and/or deletion of Synechococcus genes by transformation with suitable cloned material interrupted by resistance cassettes is well known in the art. Genes may also be replaced by specifically mutated versions using selection for closely linked resistance cassettes.

Anabaena differentiates specialized cells for nitrogen fixation when the culture is deprived of a source of combined nitrogen. The differentiated cells have a unique glycolipid envelope containing C26 and C28 fatty acids (Murata and Nishida, 1987), whose synthesis must start with the reaction catalyzed by ACC. Therefore ACC must be developmentally regulated in Anabaena. Powerful systems of genetic analysis exist for Anabaena as well (Golden et al., 1987).

That cyanobacteria and plants are evolutionarily-related make the former useful sources of cloned genes for the isolation of plant cDNAs. This method is well known to those of skill in the art. For example, the cloned gene for the enzyme phytoene desaturase, which functions in the synthesis of carotenoids, isolated from cyanobacteria was used as a probe to isolate the cDNA for that gene from tomato (Pecker et al., 1992).

5. Deficiencies in the Prior Art

The genetic transformation of important commercial monocotyledonous agriculture crops with DNA segments encoding herbicide-resistant ACC enzymes would be a revolution in the farming of such grains as wheat, rice, maize, barley, rye, and oats. Moreover the availability for modulating the herbicide resistance of plants through the alteration of ACC-encoding DNA segments and the polypeptides themselves would be highly desirable. Methods of identifying and assaying the levels of ACC activity in these plants would also be important in genetically engineering grain crops and the like with desirable herbicide-resistant qualities. Likewise the availability of DNA segments encoding dicotyledonous ACC and nucleic acid segments derived therefrom would provide a much-needed means of genetically altering the activity of ACC in vivo and in vitro.

What is lacking in the prior art, therefore, is the identification of DNA segments encoding plant and cyanobacterial ACC enzymes, and the development of methods and processes for their use in creation of modified, transgenic plants which have altered herbicide resistance. Moreover, novel methods providing transgenic plants using DNA segments encoding ACC polypeptides to modulate ACC activity, fatty acid biosynthesis in general, and oil content of plant cells in specific, are greatly needed to provide transformed plants altered in such activity. Methods for determining ACC activity in vivo and quantitating herbicide resistance in plants would also represent major improvements over the current state of the art.

SUMMARY OF THE INVENTION

The present invention seeks to overcome these and other inherent deficiencies in the prior art by providing compositions comprising novel ACC polypeptides from plant and cyanobacterial species. The invention also provides novel DNA segments encoding eukaryotic and prokaryotic ACCs, and methods and processes for their use in regulating the oil content of plant tissues, for conferring and modulating resistance to particular herbicides in a variety of plant species, and for altering the activity of ACC in plant cells in vivo. Also disclosed are methods for determining herbicide resistance and kits for identifying the presence of plant ACC polypeptides and DNA segments.

1. ACC Genes and Polynucleotides

The present invention provides polynucleotides and polypeptides relating to a whole or a portion of acetyl-CoA carboxylase (ACC) of cyanobacteria and plants as well as processes using those polynucleotides and polypeptides.

As used herein the term "polynucleotide" means a sequence of nucleotides connected by phosphodiester linkages. A polynucleotide of the present invention can comprise from about 2 to about several hundred thousand base pairs. Preferably, a polynucleotide comprises from about 5 to about 150,000 base pairs. Preferred lengths of particular polynucleotides are set forth hereinafter.

A polynucleotide of the present invention can be a deoxyribonucleic acid (DNA) molecule or a ribonucleic acid (RNA) molecule. Where a polynucleotide is a DNA molecule, that molecule can be a gene or a cDNA molecule. Nucleotide bases are indicated herein by a single letter code: adenine (A), guanine (G), thymine (T), cytosine (C), and uracil (U).

In one embodiment, the present invention contemplates isolated and purified polynucleotides comprising DNA segments encoding polypeptides which have the ability to catalyze the carboxylation of a biotin carboxyl carrier protein of a cyanobacterium. Preferably, the cyanobacterium is Anabaena or Synechococcus. A preferred Anabaena is Anabaena 7120. A preferred Synechococcus is *Anacystis nidulans* R2 (Synechococcus sp. strain PCC 7942).

Preferably, a polypeptide is a biotin carboxylase enzyme of a cyanobacterium. This enzyme is a subunit of cyanobacterial acetyl-CoA carboxylase and participates in the carboxylation of acetyl-CoA. In a preferred embodiment, a BC polypeptide is encoded by a polynucleotide comprising an accC gene which has the nucleic acid sequence of SEQ ID NO:5 (Anabaena accC) or SEQ ID NO:7 (Synechococcus accC), or functional equivalents thereof. The BC polypeptide preferably comprises the amino acid sequence of SEQ ID NO:6 (Anabaena BC) or SEQ ID NO:8 (Synechococcus BC), or functional equivalents thereof.

In a second embodiment, the present invention contemplates isolated and purified polynucleotides comprising DNA segments encoding a biotin carboxyl carrier protein of a cyanobacterium. Preferably, the cyanobacterium is Anabaena or Synechococcus. A preferred Anabaena is Anabaena 7120. A preferred Synechococcus is *Anacystis nidulans* R2 (Synechococcus sp. strain PCC 7942).

Preferably, a polypeptide is a biotin carboxyl carrier protein of a cyanobacterium. This polypeptide is a subunit of cyanobacterial acetyl-CoA carboxylase and participates in the carboxylation of acetyl-CoA. In a preferred embodiment, a BCCP polypeptide is encoded by a polynucleotide comprising an accB gene which has the nucleic acid sequence of SEQ ID NO:1 (Anabaena accB) or SEQ ID NO:3 (Synechococcus accB), or functional equivalents thereof. The BCCP polypeptide preferably comprises the amino acid sequence of SEQ ID NO:2 (Anabaena BCCP) or SEQ ID NO:4 (Synechococcus BCCP), or functional equivalents thereof.

In a third embodiment, the present invention contemplates isolated and purified polynucleotides comprising DNA segments encoding a carboxyltransferase protein of a cyanobacterium. Preferably, the cyanobacterium is Anabaena or Synechococcus. A preferred Anabaena is Anabaena 7120. A preferred Synechococcus is *Anacystis nidulans* R2 (Synechococcus sp. strain PCC 7942).

Preferably, a polypeptide is a carboxyltransferase α or β subunit protein of a cyanobacterium. These polypeptides are subunits of cyanobacterial acetyl-CoA carboxylase and participate in the carboxylation of acetyl-CoA. In a preferred embodiment, a CTα polypeptide is encoded by a polynucleotide comprising an accA gene which has the nucleic acid sequence of SEQ ID NO:11 (Synechococcus accA), or a functional equivalent thereof. The CTα polypeptide preferably comprises the amino acid sequence of SEQ ID NO:12 (Synechococcus CTα), or a functional equivalent thereof.

In a fourth embodiment, the present invention contemplates isolated and purified polynucleotides comprising DNA segments encoding an acetyl-CoA carboxylase protein of a plant. Preferably, the plant is a monocotyledonous or a dicotyledonous plant. An exemplary and preferred monocotyledonous plant is wheat, rice, maize, barley, rye, oats or timothy grass. An exemplary and preferred dicotyledonous plant is soybean, rape, sunflower, tobacco, Arabidopsis, petunia, pea, canola, bean, tomato, potato, lettuce, spinach, alfalfa, cotton or carrot. A preferred monocotyledonous plant is wheat, and a preferred dicotyledonous plant is canola.

Preferably, a polypeptide is an acetyl-CoA carboxylase (ACC) protein of a plant. This polypeptide participates in the carboxylation of acetyl-CoA. In a preferred embodiment, an ACC polypeptide is encoded by a polynucleotide comprising an ACC cDNA which has the nucleic acid sequence of SEQ ID NO:9 (wheat ACC) or SEQ ID NO:19 (canola ACC), or functional equivalents thereof. The ACC polypeptide preferably comprises the amino acid sequence of SEQ ID NO:10 (wheat ACC) or SEQ ID NO:20 (canola ACC), or functional equivalents thereof.

In yet another aspect, the present invention provides an isolated and purified DNA molecule comprising a promoter operatively linked to a coding region that encodes (1) a polypeptide having the ability to catalyze the carboxylation of a biotin carboxyl carrier protein of a cyanobacterium, (2) a biotin carboxyl carrier protein of a cyanobacterium or (3) a plant polypeptide having the ability to catalyze the carboxylation of acetyl-CoA, which coding region is operatively linked to a transcription-terminating region, whereby said promoter drives the transcription of said coding region.

In another aspect, the present invention provides an isolated polypeptide having the ability to catalyze the carboxylation of a biotin carboxyl carrier protein of a cyanobacterium such as Synechococcus. Preferably a biotin carboxyl carrier protein gene includes the nucleic acid sequence of SEQ ID NO:2 and the polypeptide has the amino acid residue sequence of SEQ ID NO:6.

2. ACC Polypeptides and Anti-ACC Antibodies

The present invention also provides (1) an isolated and purified biotin carboxyl carrier protein of a cyanobacterium such as Anabaena or Synechococcus, which protein includes the amino acid residue sequence of SEQ ID NO:2 or SEQ ID NO:4, respectively; (2) an isolated and purified biotin carboxylase of a cyanobacterium such as Anabaena or Synechococcus, which protein includes the amino acid residue sequence of SEQ ID NO:6 or SEQ ID NO:8, respectively; (3) an isolated and purified carboxyltransferase α subunit protein of a cyanobacterium such as Synechococcus, which protein includes the amino acid residue sequence of SEQ ID NO:12; (4) an isolated and purified monocotyledonous plant polypeptide from wheat having a molecular weight of about 220 kDa, dimers of which have the ability to catalyze the carboxylation of acetyl-CoA, which protein includes the amino acid sequence of SEQ ID NO:10; and (5) an isolated and purified dicotyledonous plant polypeptide from canola having the ability to catalyze the carboxylation of acetyl-CoA, which protein includes the amino acid sequence of SEQ ID NO:20.

Another aspect of the invention concerns methods and compositions for the use of the novel peptides of the invention in the production of anti-ACC antibodies. The present invention also provides methods for identifying ACC and ACC-related polypeptides, which methods comprise contacting a sample suspected of containing such polypeptides with an immunologically effective amount of a composition comprising one or more specific anti-ACC antibodies disclosed herein. Peptides that include the amino acid sequence of any of SEQ ID NO:4 through SEQ ID NO:8 and their derivatives will be preferred for use in generating such anti-ACC antibodies. Samples which may be tested or assayed for the presence of such ACC and ACC-related polypeptides include whole cells, cell extracts, cell homogenates, cell-free supernatants, and the like. Such cells may be either eukaryotic (such as plant cells) or prokaryotic (such as cyanobacterial and bacterial cells).

In certain aspects, diagnostic reagents comprising the novel peptides of the present invention and/or DNA segments which encode them have proven useful as test reagents for the detection of ACC and ACC-related polypeptides.

3. ACC Transformation and Identification of Herbicide-Resistant Variants

In yet another aspect, the present invention provides a process of modulating the herbicide resistance of a plant cell by a process of transforming the plant cell with a DNA molecule comprising a promoter operatively linked to a coding region that encodes a herbicide resistant polypeptide having the ability to catalyze the carboxylation of acetyl-CoA, which coding region is operatively linked to a transcription-terminating region, whereby the promoter is capable of driving the transcription of the coding region in a monocotyledonous plant.

Preferably, a polypeptide is an acetyl-CoA carboxylase enzyme and, more preferably, a plant acetyl-CoA carboxylase. In a preferred embodiment, a coding region includes the DNA sequence of SEQ ID NO:9 or SEQ ID NO:19 and a promoter is CaMV35.

In a preferred embodiment, a cell is a cyanobacterium or a plant cell and a plant polypeptide is a monocotyledonous plant acetyl-CoA carboxylase enzyme such as wheat acetyl-CoA carboxylase enzyme. The present invention also provides a transformed cyanobacterium produced in accordance with such a process.

The present invention still further provides a process for determining the inheritance of plant resistance to herbicides of the aryloxyphenoxypropionate or cyclohexane-1,3-dione classes, which generally involves measuring resistance to these herbicides in a parental plant line and in the progeny of the parental plant line, detecting the presence of complexes between DNA restriction fragments and the ACC gene, and then correlating the herbicide resistance of the parental and progeny plants with the presence of particular sizes of ACC gene-containing DNA fragments as an indication of the inheritance of resistance to herbicides of these classes.

Preferably, the acetyl-CoA carboxylase is a dicotyledonous plant acetyl-CoA carboxylase enzyme or a mutated monocotyledonous plant acetyl-CoA carboxylase that confers herbicide resistance or a hybrid acetyl-CoA carboxylase comprising a portion of a dicotyledonous plant acetyl-CoA carboxylase, a portion of a monocotyledonous plant acetyl-CoA carboxylase or one or more domains of a cyanobacterial acetyl-CoA carboxylase.

Where a cyanobacterium is transformed with a plant ACC DNA molecule, that cyanobacterium can be used to identify herbicide resistant mutations in the gene encoding ACC. In accordance with such a use, the present invention provides a process for identifying herbicide resistant variants of a plant acetyl-CoA carboxylase comprising the steps of:

(a) transforming cyanobacteria with a DNA molecule that encodes a monocotyledonous plant acetyl-CoA carboxylase enzyme to form transformed or transfected cyanobacteria;

(b) inactivating cyanobacterial acetyl-CoA carboxylase;

(c) exposing the transformed cyanobacteria to an effective herbicidal amount of a herbicide that inhibits acetyl-CoA carboxylase activity;

(d) identifying transformed cyanobacteria that are resistant to the herbicide; and (e) characterizing DNA that encodes acetyl-CoA carboxylase from the cyanobacteria of step (d).

Means for transforming cyanobacteria as well as expression vectors used for such transformation are preferably the same as set forth above. In a preferred embodiment, cyanobacteria are transformed or transfected with an expression vector comprising a coding region that encodes wheat ACC. Cyanobacteria resistant to the herbicide are identified. Identifying comprises growing or culturing transformed cells in the presence of the herbicide and recovering those cells that survive herbicide exposure. Transformed, herbicide-resistant cells are then grown in culture, collected and total DNA extracted using standard techniques. ACC DNA is isolated, amplified if needed and then characterized by comparing that DNA with DNA from ACC known to be inhibited by that herbicide.

In still yet another aspect, the present invention provides a process for identifying herbicide resistant variants of a plant acetyl-CoA carboxylase. Such methods generally involve transforming a cyanobacterium or a bacterium or a yeast cell with a DNA molecule that encodes a plant acetyl-CoA carboxylase enzyme, inactivating the host-cell acetyl-CoA carboxylase, and exposing the cells to a herbicide that inhibits monocotyledonous plant acetyl-CoA carboxylase activity. Transformed cells may be identified which are resistant to the herbicide; and the DNA that encodes resistant acetyl-CoA carboxylase in these transformed cells may be examined and characterized.

4. ACC Transgenes and Transgenic Plants

In yet another aspect, the present invention provides a process of altering the carboxylation of acetyl-CoA in a cell comprising transforming the cell with a DNA molecule comprising a promoter operatively linked to a coding region that encodes a plant polypeptide having the ability to catalyze the carboxylation of acetyl-CoA, which coding region is operatively linked to a transcription-terminating region, whereby the promoter is capable of driving the transcription of the coding region in the cell. The invention also provides a means of reducing the amount of ACC in plants by expression of ACC antisense mRNA.

Another aspect of the invention relates generally to transgenic plants which express genes or gene segments encoding the novel polypeptide compositions disclosed herein. As used herein, the term "transgenic plants" is intended to refer to plants that have incorporated DNA sequences, including but not limited to genes which are perhaps not normally present, DNA sequences not normally transcribed into RNA or translated into a protein ("expressed"), or any other genes or DNA sequences which one desires to introduce into the non-transformed plant, such as genes which may normally be present in the non-transformed plant but which one desires to either genetically engineer or to have altered expression. It is contemplated that in some instances the genome of transgenic plants of the present invention will have been augmented through the stable introduction of the transgene. However, in other instances, the introduced gene will replace an endogenous sequence.

A preferred gene which may be introduced includes, for example, the ACC DNA sequences from cyanobacterial or plant origin, particularly those described herein which are obtained from the cyanobacterial species Synechococcus or Anabaena, or from plant species such as wheat or canola, of any of those sequences which have been genetically engineered to decrease or increase the activity of the ACC in such transgenic species.

Vectors, plasmids, cosmids, YACs (yeast artificial chromosomes) and DNA segments for use in transforming such cells will, of course, generally comprise either the cDNA, gene or gene sequences of the present invention, and particularly those encoding ACC. These DNA constructs can further include structures such as promoters, enhancers, polylinkers, or even regulatory genes as desired. The DNA segment or gene may encode either a native or modified ACC, which will be expressed in the resultant recombinant cells, and/or which will impart an improved phenotype to the regenerated plant.

Such transgenic plants may be desirable for increasing the herbicide resistance of a monocotyledonous plant, by incorporating into such a plant, a transgenic DNA segment encoding a plant acetyl-CoA carboxylase enzyme which is resistant to herbicide inactivation, e.g., a dicotyledonous ACC gene. Alternatively a cyanobacterial ACC polypeptide-encoding DNA segment could also be used to prepare a transgenic plant with increased resistance to herbicide inactivation.

Alternatively transgenic plants may be desirable having an decreased herbicide resistance. This would be particularly desirable in creating transgenic plants which are more sensitive to such herbicides. Such a herbicide-sensitive plant could be prepared by incorporating into such a plant, a transgenic DNA segment encoding a plant acetyl-CoA carboxylase enzyme which is sensitive to herbicide inactivation, e.g., a monocotyledonous ACC gene, or a mutated dicotyledonous or cyanobacterial ACC-encoding gene.

In other aspects of the present invention, the invention concerns processes of modifying the oil content of a plant cell. Such modifications generally involve expressing in such plant cells transgenic DNA segments encoding a plant or cyanobacterial acetyl-CoA carboxylase composition of the present invention. Such processes would generally result in increased expression of ACC and hence, increased oil production in such cells. Alternatively, when it is desirable to decrease the oil production of such cells, ACC-encoding transgenic DNA segments or antisense (complementary) DNA segments to genomic ACC-encoding DNA sequences may be used to transform cells.

Either process may be facilitated by introducing into such cells DNA segments encoding a plant or cyanobacterial acetyl-CoA carboxylase polypeptide, as long as the resulting transgenic plant expresses the acetyl-CoA carboxylase-encoding transgene.

The present invention also provides a transformed plant produced in accordance with the above process as well as a transgenic plant and a transgenic plant seed having incorporated into its genome a transgene that encodes a herbicide resistant polypeptide having the ability to catalyze the carboxylation of acetyl-CoA. All such transgenic plants having incorporated into their genome transgenic DNA segments encoding plant or cyanobacterial acetyl-CoA carboxylase polypeptides are aspects of this invention.

5. ACC Screening and Immunodetection Kits

The present invention contemplates methods and kits for screening samples suspected of containing ACC polypeptides or ACC-related polypeptides, or cells producing such polypeptides. Said kit can contain a nucleic acid segment or an antibody of the present invention. The kit can contain reagents for detecting an interaction between a sample and a nucleic acid or antibody of the present invention. The provided reagent can be radio-, fluorescently- or enzymatically-labeled. The kit can contain a known radiolabeled agent capable of binding or interacting with a nucleic acid or antibody of the present invention.

The reagent of the kit can be provided as a liquid solution, attached to a solid support or as a dried powder. Preferably, when the reagent is provided in a liquid solution, the liquid solution is an aqueous solution. Preferably, when the reagent provided is attached to a solid support, the solid support can be chromatograph media, a test plate having a plurality of wells, or a microscope slide. When the reagent provided is a dry powder, the powder can be reconstituted by the addition of a suitable solvent, that may be provided.

In still further embodiments, the present invention concerns immunodetection methods and associated kits. It is proposed that the ACC peptides of the present invention may be employed to detect antibodies having reactivity therewith, or, alternatively, antibodies prepared in accordance with the present invention, may be employed to detect ACC or ACC-related epitope-containing peptides. In general, these methods will include first obtaining a sample suspected of containing such a protein, peptide or antibody, contacting the sample with an antibody or peptide in accordance with the present invention, as the case may be, under conditions effective to allow the formation of an immunocomplex, and then detecting the presence of the immunocomplex.

In general, the detection of immunocomplex formation is quite well known in the art and may be achieved through the application of numerous approaches. For example, the present invention contemplates the application of ELISA, RIA, immunoblot (e.g., dot blot), indirect immunofluorescence techniques and the like. Generally, immunocomplex formation will be detected through the use of a label, such as a radiolabel or an enzyme tag (such as alkaline phosphatase, horseradish peroxidase, or the like). Of course, one may find additional advantages through the use of a secondary binding ligand such as a second antibody or a biotin/avidin ligand binding arrangement, as is known in the art.

For assaying purposes, it is proposed that virtually any sample suspected of comprising either an ACC peptide or an ACC-related peptide or antibody sought to be detected, as the case may be, may be employed. It is contemplated that such embodiments may have application in the titering of antigen or antibody samples, in the selection of hybridomas, and the like. In related embodiments, the present invention contemplates the preparation of kits that may be employed to detect the presence of ACC or ACC-related proteins or peptides and/or antibodies in a sample. Samples may include cells, cell supernatants, cell suspensions, cell extracts, enzyme fractions, protein extracts, or other cell-free compositions suspected of containing ACC peptides. Generally speaking, kits in accordance with the present invention will include a suitable ACC peptide or an antibody directed against such a protein or peptide, together with an immunodetection reagent and a means for containing the antibody or antigen and reagent. The immunodetection reagent will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, as noted above, a number of exemplary labels are known in the art and all such labels may be employed in connection with the present invention.

The container will generally include a vial into which the antibody, antigen or detection reagent may be placed, and preferably suitably aliquotted. The kits of the present invention will also typically include a means for containing the antibody, antigen, and reagent containers in close confinement for commercial sale. Such containers may include injection or blow-molded plastic containers into which the desired vials are retained.

6. ELISAs and Immunoprecipitation

ELISAs may be used in conjunction with the invention. En an ELISA assay, proteins or peptides incorporating ACC antigen sequences are immobilized onto a selected surface, preferably a surface exhibiting a protein affinity such as the wells of a polystyrene microtiter plate. After washing to remove incompletely adsorbed material, it is desirable to bind or coat the assay plate wells with a nonspecific protein that is known to be antigenically neutral with regard to the test antisera such as bovine serum albumin (BSA), casein or solutions of milk powder. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hours, at temperatures preferably on the order of about 25° to about 27° C. Following incubation, the antisera-contacted surface is washed so as to remove non-immunocomplexed material. A preferred washing procedure includes washing with a solution such as PBS/Tween®, or borate buffer.

Following formation of specific immunocomplexes between the test sample and the bound antigen, and subsequent washing, the occurrence and even amount of immunocomplex formation may be determined by subjecting same to a second antibody having specificity for the first. To provide a detecting means, the second antibody will preferably have an associated enzyme that will generate a color development upon incubating with an appropriate chromogenic substrate. Thus, for example, one will desire to contact and incubate the antisera-bound surface with a urease or peroxidase-conjugated anti-human IgG for a period of time and under conditions which favor the development of immunocomplex formation (e.g., incubation for 2 hours at room temperature in a PBS-containing solution such as PBS Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethylbenzthiazoline)-6-sulfonic acid (ABTS) and $H_2O_2$, in the case of peroxidase as the enzyme label. Quantification is then achieved by measuring the degree of color generation, e.g., using a visible spectra spectrophotometer.

The antibodies of the present invention are particularly useful for the isolation of antigens by immunoprecipitation. Immunoprecipitation involves the separation of the target antigen component from a complex mixture, and is used to discriminate or isolate minute amounts of protein. For the isolation of membrane proteins cells must be solubilized into detergent micelles. Nonionic salts are preferred, since other agents such as bile salts, precipitate at acid pH or in the presence of bivalent cations.

In an alternative embodiment the antibodies of the present invention are useful for the close juxtaposition of two antigens. This is particularly useful for increasing the localized concentration of antigens, e.g. enzyme-substrate pairs.

7. Western Blots

The compositions of the present invention will find great use in immunoblot or western blot analysis. The anti-peptide antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. This is especially useful when the antigens studied are immunoglobulins (precluding the use of immunoglobulins binding bacterial cell wall components), the antigens studied cross-react with the detecting agent, or they migrate at the same relative molecular weight as a cross-reacting signal.

Immunologically-based detection methods for use in conjunction with Western blotting include enzymatically-, radiolabel-, or fluorescently-tagged secondary antibodies against the toxin moiety are considered to be of particular use in this regard.

8. Epitopic Core Sequences

The present invention is also directed to protein or peptide compositions, free from total cells and other peptides, which comprise a purified protein or peptide which incorporates an epitope that is immunologically cross-reactive with one or more anti-ACC antibodies.

As used herein, the term "incorporating an epitope(s) that is immunologically cross-reactive with one or more anti-ACC antibodies" is intended to refer to a peptide or protein antigen which includes a primary, secondary or tertiary structure similar to an epitope located within an ACC polypeptide. The level of similarity will generally be to such a degree that monoclonal or polyclonal antibodies directed against the ACC polypeptide will also bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art.

The identification of ACC immunodominant epitopes, and/or their functional equivalents, suitable for use in vaccines is a relatively straightforward matter. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, for example, Jameson and Wolf, 1988; Wolf et al., 1988; U.S. Pat. No. 4,554,101). The amino acid sequence of these "epitopic core sequences" may then be readily incorporated into peptides, either through the application of peptide synthesis or recombinant technology.

Preferred peptides for use in accordance with the present invention will generally be on the order of 8 to 20 amino acids in length, and more preferably about 8 to about 15 amino acids in length. It is proposed that shorter antigenic ACC-derived peptides will provide advantages in certain circumstances, for example, in the preparation of vaccines or in immunologic detection assays. Exemplary advantages include the ease of preparation and purification, the relatively low cost and improved reproducibility of production, and advantageous biodistribution.

It is proposed that particular advantages of the present invention may be realized through the preparation of synthetic peptides which include modified and/or extended epitopic/immunogenic core sequences which result in a "universal" epitopic peptide directed to ACC and ACC-related sequences. These epitopic core sequences are identified herein in particular aspects as hydrophilic regions of the ACC polypeptide antigen. It is proposed that these regions represent those which are most likely to promote T-cell or B-cell stimulation, and, hence, elicit specific antibody production.

An epitopic core sequence, as used herein, is a relatively short stretch of amino acids that is "complementary" to, and therefore will bind, antigen binding sites on transferrin-binding protein antibodies. Additionally or alternatively, an epitopic core sequence is one that will elicit antibodies that are cross-reactive with antibodies directed against the peptide compositions of the present invention. It will be understood that in the context of the present disclosure, the term "complementary" refers to amino acids or peptides that exhibit an attractive force towards each other. Thus, certain epitope core sequences of the present invention may be operationally defined in terms of their ability to compete with or perhaps displace the binding of the desired protein antigen with the corresponding protein-directed antisera.

In general, the size of the polypeptide antigen is not believed to be particularly crucial, so long as it is at least large enough to carry the identified core sequence or sequences. The smallest useful core sequence anticipated by the present disclosure would generally be on the order of about 8 amino acids in length, with sequences on the order of 10 to 20 being more preferred. Thus, this size will generally correspond to the smallest peptide antigens prepared in accordance with the invention. However, the size of the antigen may be larger where desired, so long as it contains a basic epitopic core sequence.

The identification of epitopic core sequences is known to those of skill in the art, for example, as described in U.S. Pat. No. 4,554,101, incorporated herein by reference, which teaches the identification and preparation of epitopes from amino acid sequences on the basis of hydrophilicity. Moreover, numerous computer programs are available for use in predicting antigenic portions of proteins (see e.g., Jameson and Wolf, 1988; Wolf et al., 1988). Computerized peptide sequence analysis programs (e.g., DNAStar® software, DNAStar, Inc., Madison, Wis.) may also be useful in designing synthetic peptides in accordance with the present disclosure.

Syntheses of epitopic sequences, or peptides which include an antigenic epitope within their sequence, are readily achieved using conventional synthetic techniques such as the solid phase method (e.g., through the use of commercially available peptide synthesizer such as an Applied Biosystems Model 430A Peptide Synthesizer). Peptide antigens synthesized in this manner may then be aliquotted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of about 7.0 to about 7.5. Moreover, it may be desirable to include agents which will inhibit microbial growth, such as sodium azide or Merthiolate. For extended storage in an aqueous state it will be desirable to store the solutions at 4° C., or more preferably, frozen. Of course, where the peptides are stored in a lyophilized or powdered state, they may be stored virtually indefinitely, e.g., in metered aliquots that may be rehydrated with a predetermined amount of water (preferably distilled) or buffer prior to use.

9. DNA Segments

The present invention also concerns DNA segments, that can be isolated from virtually any source, that are free from total genomic DNA and that encode the novel peptides disclosed herein. DNA segments encoding these peptide species may prove to encode proteins, polypeptides, subunits, functional domains, and the like of ACC-related or other non-related gene products. In addition these DNA segments may be synthesized entirely in vitro using methods that are well-known to those of skill in the art.

As used herein, the term "DNA segment" refers to a DNA molecule that has been isolated free of total genomic DNA of a particular species. Therefore, a DNA segment encoding an ACC peptide refers to a DNA segment that contains ACC coding sequences yet is isolated away from, or purified free from, total genomic DNA of the species from which the DNA segment is obtained. Included within the term "DNA segment", are DNA segments and smaller fragments of such segments, and also recombinant vectors, including, for example, plasmids, cosmids, phagemids, phage, viruses, and the like.

Similarly, a DNA segment comprising an isolated or purified ACC gene refers to a DNA segment which may include in addition to peptide encoding sequences, certain other elements such as, regulatory sequences, isolated substantially away from other naturally occurring genes or protein-encoding sequences. In this respect, the term "gene" is used for simplicity to refer to a functional protein-, polypeptide- or peptide-encoding unit. As will be understood by those in the art, this functional term includes both genomic sequences, cDNA sequences and smaller engineered gene segments that express, or may be adapted to express, proteins, polypeptides or peptides.

"Isolated substantially away from other coding sequences" means that the gene of interest, in this case, a gene encoding ACC, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences that encode an ACC peptide species that includes within its amino acid sequence an amino acid sequence essentially as set forth in any of SEQ ID NO:2, SEQ ID NO:4, SEQ ID NO:6, SEQ ID NO:8, SEQ ID NO:10, SEQ ID NO:12, and SEQ ID NO:20.

The term "a sequence essentially as set forth in any of SEQ ID NO:2, SEQ ID NO:4, SEQ ID NO:6, SEQ ID NO:8, SEQ ID NO:10, SEQ ID NO:12, and SEQ ID NO:20" means that the sequence substantially corresponds to a portion of the sequence of either SEQ ID NO:2, SEQ ID NO:4, SEQ ID NO:6, SEQ ID NO:8, SEQ ID NO:10, SEQ ID NO:12, or SEQ ID NO:20 and has relatively few amino acids that are not identical to, or a biologically functional equivalent of, the amino acids of any of these sequences. The term "biologically functional equivalent" is well understood in the art and is further defined in detail herein (for example, see Preferred Embodiments). Accordingly, sequences that have between about 70% and about 80%, or more preferably between about 81% and about 90%, or even more preferably between about 91% and about 99% amino acid sequence identity or functional equivalence to the amino acids of any of SEQ ID NO:2, SEQ ID NO:4, SEQ ID NO:6, SEQ ID NO:8, SEQ ID NO:10, SEQ ID NO:12, and SEQ ID NO:20 will be sequences that are "essentially as set forth in any of SEQ ID NO:2, SEQ ID NO:4, SEQ ID NO:6, SEQ ID NO:8, SEQ ID NO:10, SEQ ID NO:12, and SEQ ID NO:20."

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared that include a short contiguous stretch encoding either of the peptide sequences disclosed in any of SEQ ED NO:2, SEQ ID NO:4, SEQ ID NO:6, SEQ ID NO:8, SEQ ID NO:10, SEQ ID NO:12, and SEQ ID NO:20, or that are identical to or complementary to DNA sequences which encode any of the peptides disclosed in SEQ ID NO:2, SEQ ID NO:4, SEQ ID NO:6, SEQ ID NO:8, SEQ ID NO:10, SEQ ID NO:12, and SEQ ID NO:20, and particularly those DNA segments disclosed in SEQ ID NO:1, SEQ ID NO:3, SEQ ID NO:5, SEQ ID NO:7, SEQ ID NO:9, SEQ ID NO:11, or SEQ ID NO:19. For example, DNA sequences such as about 14 nucleotides, and that are up to about 10,000, about 5,000, about 3,000, about 2,000, about 1,000, about 500, about 200, about 100, about 50, and about 14 base pairs in length (including all intermediate lengths) are also contemplated to be useful.

It will be readily understood that "intermediate lengths", in these contexts, means any length between the quoted ranges, such as 14, 15, 16, 17, 18, 19, 20, etc.; 21, 22, 23, etc.; 30, 31, 32, etc.; 50, 51, 52, 53, etc.; 100, 101, 102, 103, etc.; 150, 151, 152, 153, etc.; including all integers through the 200–500; 500–1,000; 1,000–2,000; 2,000–3,000; 3,000–5,000; and up to and including sequences of about 10,000 nucleotides and the like.

It will also be understood that this invention is not limited to the particular nucleic acid sequences which encode peptides of the present invention, or which encode the amino acid sequences of SEQ ED NO:2, SEQ ID NO:4, SEQ ID NO:6, SEQ ID NO:8, SEQ ID NO:10, SEQ ID NO:12, and SEQ ID NO:20, including those DNA sequences which are particularly disclosed in SEQ ID NO:1, SEQ ID NO:3, SEQ ID NO:5, SEQ ID NO:7, SEQ ID NO:9, SEQ ED NO:11, and SEQ ID NO:19. Recombinant vectors and isolated DNA segments may therefore variously include the peptide-coding regions themselves, coding regions bearing selected alterations or modifications in the basic coding region, or they may encode larger polypeptides that nevertheless include these peptide-coding regions or may encode biologically functional equivalent proteins or peptides that have variant amino acids sequences.

The DNA segments of the present invention encompass biologically-functional equivalent peptides. Such sequences may arise as a consequence of codon redundancy and functional equivalency that are known to occur naturally within nucleic acid sequences and the proteins thus encoded. Alternatively, functionally-equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test mutants in order to examine activity at the molecular level.

If desired, one may also prepare fusion proteins and peptides, e.g., where the peptide-coding regions are aligned within the same expression unit with other proteins or peptides having desired functions, such as for purification or immunodetection purposes (e.g., proteins that may be purified by affinity chromatography and enzyme label coding regions, respectively).

Recombinant vectors form further aspects of the present invention. Particularly useful vectors are contemplated to be those vectors in which the coding portion of the DNA segment, whether encoding a full length protein or smaller peptide, is positioned under the control of a promoter. The promoter may be in the form of the promoter that is naturally associated with a gene encoding peptides of the present invention, as may be obtained by isolating the 5' non-coding sequences located upstream of the coding segment or exon, for example, using recombinant cloning and/or PCR™ technology, in connection with the compositions disclosed herein.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a DNA segment encoding an ACC peptide in its natural environment. Such promoters may include promoters normally associated with other genes, and/or promoters isolated from any bacterial, viral, eukaryotic, or plant cell. Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al., 1989. The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression include, but are not limited to, the Pichia expression vector system (Pharmacia LKB Biotechnology).

In connection with expression embodiments to prepare recombinant proteins and peptides, it is contemplated that longer DNA segments will most often be used, with DNA segments encoding the entire peptide sequence being most preferred. However, it will be appreciated that the use of shorter DNA segments to direct the expression of ACC peptides or epitopic core regions, such as may be used to generate anti-ACC antibodies, also falls within the scope of the invention. DNA segments that encode peptide antigens from about 8 to about 50 amino acids in length, or more preferably, from about 8 to about 30 amino acids in length, or even more preferably, from about 8 to about 20 amino acids in length are contemplated to be particularly useful. Such peptide epitopes may be amino acid sequences which comprise contiguous amino acid sequences from any of SEQ ID NO:2, SEQ ID NO:4, SEQ ID NO:6, SEQ ID NO:8, SEQ ID NO:10, SEQ ID NO:12, or SEQ ID NO:20.

In addition to their use in directing the expression of ACC peptides of the present invention, the nucleic acid sequences contemplated herein also have a variety of other uses. For example, they also have utility as probes or primers in nucleic acid hybridization embodiments. As such, it is contemplated that nucleic acid segments that comprise a sequence region that consists of at least a 14 nucleotide long contiguous sequence that has the same sequence as, or is complementary to, a 14 nucleotide long contiguous DNA segment any of SEQ ID NO:1, SEQ ID NO:3, SEQ ID NO:5, SEQ ID NO:7, SEQ ID NO:9, SEQ ID NO:11, and SEQ ID NO:19 will find particular utility. Longer contiguous identical or complementary sequences, e.g., those of about 20, 30, 40, 50, 100, 200, 500, 1000, 2000, 5000, 10000 etc. (including all intermediate lengths and up to and including full-length sequences will also be of use in certain embodiments.

The ability of such nucleic acid probes to specifically hybridize to ACC-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of 10–14, 15–20, 30, 50, or even of 100–200 nucleotides or so, identical or complementary to DNA sequences of any of SEQ ID NO:1, SEQ ID NO:3, SEQ ID NO:5, SEQ ID NO:7, SEQ ID NO:9, SEQ ID NO:11, and SEQ ID NO:19, are particularly contemplated as hybridization probes for use in, e.g., Southern and Northern blotting. Smaller fragments will generally find use in hybridization embodiments, wherein the length of the contiguous complementary region may be varied, such as between about 10–14 and about 100 or 200 nucleotides, but larger contiguous complementarity stretches may be used, according to the length complementary sequences one wishes to detect.

The use of a hybridization probe of about 14 nucleotides in length allows the formation of a duplex molecule that is both stable and selective. Molecules having contiguous complementary sequences over stretches greater than 14 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 contiguous nucleotides, or even longer where desired.

Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. Nos. 4,683,195 and 4,683,202 (each incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by about 0.02M to about 0.15M NaCl at temperatures of about 50° C. to about 70° C. Such selective conditions tolerate little, if any, mismatch between the probe and the template or target strand, and would be particularly suitable for isolating ACC-encoding DNA segments. Detection of DNA segments via hybridization is well-known to those of skill in the art, and the teachings of U.S. Pat. Nos. 4,965,188 and 5,176,995 (each incorporated herein by reference) are exemplary of the methods of hybridization analyses. Teachings such as those found in the texts of Maloy et al., 1993; Segal 1976; Proskop, 1991; and Kuby, 1991, are particularly relevant.

Of course, for some applications, for example, where one desires to prepare mutants employing a mutant primer strand hybridized to an underlying template or where one seeks to isolate ACC-encoding sequences from related species, functional equivalents, or the like, less stringent hybridization conditions will typically be needed in order to allow formation of the heteroduplex. In these circumstances, one may desire to employ conditions such as about 0.15M to about 0.9M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide-variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, colorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

10. Biological Functional Equivalents

Modification and changes may be made in the structure of the peptides of the present invention and DNA segments which encode them and still obtain a functional molecule that encodes a protein or peptide with desirable characteristics. The following is a discussion based upon changing the amino acids of a protein to create an equivalent, or even an improved, second-generation molecule. The amino acid changes may be achieved by changing the codons of the DNA sequence, according to the following codon table:

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

11. Site-Specific Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as E. coli polymerase 1 Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected peptide-encoding DNA segments using site-directed mutagenesis is provided as a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants.

12. Monoclonal Antibody Generation

Means for preparing and characterizing antibodies are well known in the art (See, e.g., Antibodies: A Laboratory Manual, Cold Spring Harbor Laboratory, 1988; incorporated herein by reference).

The methods for generating monoclonal antibodies (mAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

mAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified ACC protein, polypeptide or peptide. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986, pp. 60–61), but mice are preferred, with the BALB/c mouse being most preferred as this is most routinely used and generally gives a higher percentage of stable fusions.

Following immunization, somatic cells with the potential for producing antibodies, specifically B lymphocytes (B cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65–66, 1986; Campbell, pp. 75–83, 1984). For example, where the immunized animal is a mouse, one may use P3-X63/Ag8, X63-Ag8.653, NS1/1.Ag 4 1, Sp210-Ag14, FO, NSO/IU, MPC-11, MPC11-X45-GTG 1.7 and S194/5XX0 Bul; for rats, one may use R210.RCY3, Y3-Ag 1.2.3, ER983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, (Gefter et al., 1977). The use of electrically induced fusion methods is also appropriate (Goding, 1986, pp. 71–74).

Fusion procedures usually produce viable hybrids at low frequencies, about $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

DESCRIPTION OF THE PREFERRED EMBODIMENT

A. Definitions

Figure 1:
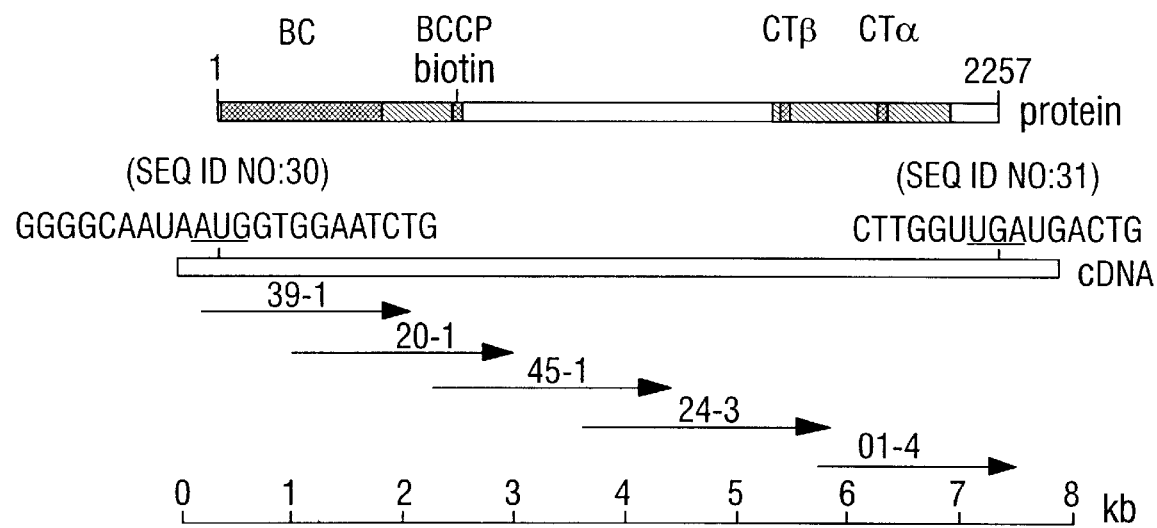
FIG. 1. The structure of wheat ACC deduced from cDNA sequence. The most conserved parts of the protein are marked in black. They include the core of the biotin carboxylase domain, a motif around the biotinylation site and two conserved motifs ($\alpha$ and $\beta$) identified previously in the $\alpha$ and $\beta$ subunits of *E. coli* CT (Li and Cronan, 1992). Parts of the protein well-conserved among eukaryotic ACCs are shown in dark gray and the least conserved parts in white. A set of overlapping cDNA fragments that were sequenced, with their relative orientation, is shown by arrows. Nucleotide sequence around the translation start and stop codons is also shown.

The following words and phrases have the meanings set forth below.

Expression: The combination of intracellular processes, including transcription and translation undergone by a coding DNA molecule such as a structural gene to produce a polypeptide.

Promoter: A recognition site on a DNA sequence or group of DNA sequences that provide an expression control element for a structural gene and to which RNA polymerase specifically binds and initiates RNA synthesis (transcription) of that gene.

Regeneration: The process of growing a plant from a plant cell (e.g., plant protoplast or explant).

Structural gene: A gene that is expressed to produce a polypeptide.

Transformation: A process of introducing an exogenous DNA sequence (e.g., a vector, a recombinant DNA molecule) into a cell or protoplast in which that exogenous DNA is incorporated into a chromosome or is capable of autonomous replication.

Transformed cell: A cell whose DNA has been altered by the introduction of an exogenous DNA molecule into that cell.

Transgenic cell: Any cell derived or regenerated from a transformed cell or derived from a transgenic cell. Exemplary transgenic cells include plant calli derived from a transformed plant cell and particular cells such as leaf, root, stem, e.g., somatic cells, or reproductive (germ) cells obtained from a transgenic plant.

Transgenic plant: A plant or progeny thereof derived from a transformed plant cell or protoplast, wherein the plant DNA contains an introduced exogenous DNA molecule not originally present in a native, non-transgenic plant of the same strain. The terms "transgenic plant" and "transformed plant" have sometimes been used in the art as synonymous terms to define a plant whose DNA contains an exogenous DNA molecule. However, it is thought more scientifically correct to refer to a regenerated plant or callus obtained from a transformed plant cell or protoplast as being a transgenic plant, and that usage will be followed herein.

Vector: A DNA molecule capable of replication in a host cell and/or to which another DNA segment can be operatively linked so as to bring about replication of the attached segment. A plasmid is an exemplary vector.

B. Polynucleotides

Amino acid sequences of biotin carboxylase (BC) from Anabaena and Synechococcus show great similarity with amino acid residue sequences from other ACC enzymes as well as with the amino acid residue sequences of other biotin-containing enzymes. Based on that homology, specific nucleotide sequences were chosen for the construction of primers for polymerase chain reaction amplification of a corresponding region of the gene for ACC from wheat. Those primers have the nucleotide sequences shown below:

Primer 15'-TCGAATTCGTNATNATHAARGC-3'(SEQ ID NO:13);

Primer 25'-GCTCTAGAGKRTGYTCNACYTG-3'(SEQ ID NO:14);

where N is A, C, G or T; H is A, C or T; R is A or G; Y is T or C and K is G or T. Primers 1 and 2 comprise a 14-nucleotide specific sequence based on a conserved amino acid sequence and an 8-nucleotide extension at the 5'-end of the primer to provide anchors for rounds of amplification after the first round and to provide convenient restriction sites for analysis and cloning.

In eukaryotic ACCs, a BCCP domain is located about 300 amino acids away from the end of the BC domain, on the C-terminal side. Therefore, it is possible to amplify the cDNA covering the interval between the BC and BCCP domains using primers from the C-terminal end of the BC domain and the conserved MKM region of the BCCP. The BC primer was based on the wheat cDNA sequence obtained as described above. Those primers, each with 6- or 8-base 5'-extensions, are shown below:

Primer 35'-GCTCTAGAATACTATTTCCTG-3'(SEQ ID NO:15)

Primer 45'-TCGAATTCWNCATYTTCATNRC-3'(SEQ ID NO:16)

N, R and Y are as defined above. W is A or T. The BC primer (primer 3) was based on the wheat cDNA sequence obtained as described above. The MKM primer (primer 4) was first checked by determining whether it would amplify the fabE gene coding BCCP from Anabaena DNA. This PCR™ was primed at the other end by using a primer based on the N-terminal amino acid residue sequence as determined on protein purified from Anabaena extracts by affinity chromatography. Those primers are shown below:

Primer 55α-GCTCTAGAYTTYAAYGARATHMG-3' (SEQ ID NO:17)

Primer 45'-TCGAATTCWNCATYTTCATNRC-3' (SEQ ID NO:18)

H, N, R, T, Y and W are as defined above. M is A or C. This amplification (using the conditions described above) yielded the correct fragment of the Anabaena fabE gene, which was used to identify cosmids that contained the entire fabE gene and flanking DNA. An about 4-kb XbaI fragment containing the gene was cloned into the vector pBluescriptKS® for sequencing. Primers 3 and 4 were then used to amplify the intervening sequence in wheat cDNA. Again, the product of the first PCR™ was eluted and reamplified by another round of PCR™, then cloned into the Invitrogen vector pCRII.

The amino acid sequence of the polypeptide predicted from the cDNA sequence for this entire fragment of wheat cDNA (1473 nucleotides) was compared with the amino acid sequences of other ACC enzymes and related enzymes from various sources. Rat, chicken and yeast are more closely related to each other than to the BC subunits of bacteria, and the BC domains of other enzymes such as pyruvate carboxylase of yeast and propionyl CoA carboxylase of rat. The amino acid identities between wheat ACC and other biotin-dependent enzymes, within the BC domain are no higher than 60%, and shown below in Table 2.

TABLE 2

|  | % identity with wheat ACC | # identity with rat ACC |
|---|---|---|
| rat ACC | 58 | (100) |
| chicken ACC | 57 |  |
| yeast ACC | 56 |  |
| Synechococcus ACC | 32 |  |
| Anabaena ACC | 30 |  |
| E. coli ACC | 33 |  |
| rat propionyl CoA carboxylase | 32 | 31 |
| yeast pyruvate carboxylase | 31 |  |

C. Probes and Primers

In another aspect, DNA sequence information provided by the invention allows for the preparation of relatively short DNA (or RNA) sequences having the ability to specifically hybridize to gene sequences of the selected polynucleotides disclosed herein. In these aspects, nucleic acid probes of an appropriate length are prepared based on a consideration of a selected ACC gene sequence, e.g., a sequence such as that shown in SEQ ED NO:9 or SEQ ID NO:19, or a selected gene sequence encoding a subunit of a cyanobacterial ACC, e.g., a sequence as that shown in SEQ ID NO:1, SEQ ID NO:3, SEQ ID NO:5, SEQ ID NO:7, or SEQ ID NO:11. The ability of such nucleic acid probes to specifically hybridize to an ACC gene sequence lend them particular utility in a variety of embodiments. Most importantly, the probes can be used in a variety of assays for detecting the presence of complementary sequences in a given sample.

In certain embodiments, it is advantageous to use oligonucleotide primers. The sequence of such primers is designed using a polynucleotide of the present invention for use in detecting, amplifying or mutating a defined segment of an ACC gene from a cyanobacterium or a plant using PCR™ technology. Segments of ACC genes from other organisms may also be amplified by PCR™ using such primers.

To provide certain of the advantages in accordance with the present invention, a preferred nucleic acid sequence employed for hybridization studies or assays includes sequences that are complementary to at least a 14 to 30 or so long nucleotide stretch of an ACC-encoding or ACC subunit-encoding sequence, such as that shown in SEQ ID NO:1, SEQ ID NO:3, SEQ ID NO:5, SEQ ID NO:7, SEQ ID NO:9, SEQ ID NO:11, or SEQ ID NO:19. A size of at least 14 nucleotides in length helps to ensure that the fragment will be of sufficient length to form a duplex molecule that is both stable and selective. Molecules having complementary sequences over stretches greater than 14 bases in length are generally preferred, though, in order to increase stability and selectivity of the hybrid, and thereby improve the quality and degree of specific hybrid molecules obtained. One will generally prefer to design nucleic acid molecules having gene-complementary stretches of 14 to 20 nucleotides, or even longer where desired. Such fragments may be readily prepared by, for example, directly synthesizing the fragment by chemical means, by application of nucleic acid reproduction technology, such as the PCR™ technology of U.S. Pat. Nos. 4,683,195, and 4,683,202, herein incorporated by reference, or by excising selected DNA fragments from recombinant plasmids containing appropriate inserts and suitable restriction sites.

Accordingly, a nucleotide sequence of the invention can be used for its ability to selectively form duplex molecules with complementary stretches of the gene. Depending on the application envisioned, one will desire to employ varying conditions of hybridization to achieve varying degree of selectivity of the probe toward the target sequence. For applications requiring a high degree of selectivity, one will typically desire to employ relatively stringent conditions to form the hybrids, for example, one will select relatively low salt and/or high temperature conditions, such as provided by about 0.02M to about 0.15M NaCl at temperatures of about 50° C. to about 70° C. These conditions are particularly selective, and tolerate little, if any, mismatch between the probe and the template or target strand.

Of course, for some applications, for example, where one desires to prepare mutants employing a mutant primer strand hybridized to an underlying template or where one seeks to isolate an ACC coding sequences for related species, functional equivalents, or the like, less stringent hybridization conditions will typically be needed in order to allow formation of the heteroduplex. In these circumstances, one may desire to employ conditions such as about 0.15M to about 0.9M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it is advantageous to employ a polynucleotide of the present invention in combination with an appropriate label for detecting hybrid formation. A wide variety of appropriate labels are known in the art, including radioactive, enzymatic or other ligands, such as avidin/biotin, which are capable of giving a detectable signal.

In general, it is envisioned that a hybridization probe described herein is useful both as a reagent in solution hybridization as well as in embodiments employing a solid phase. In embodiments involving a solid phase, the test DNA (or RNA) is adsorbed or otherwise affixed to a selected matrix or surface. This fixed nucleic acid is then subjected to specific hybridization with selected probes under desired conditions. The selected conditions depend as is well known in the art on the particular circumstances and criteria required (e.g., on the G+C content, type of target nucleic acid, source of nucleic acid, size of hybridization probe). Following washing of the matrix to remove nonspecifically bound probe molecules, specific hybridization is detected, or even quantitated, by means of the label.

D. Expression Vectors

The present invention contemplates an expression vector comprising a polynucleotide of the present invention. Thus, in one embodiment an expression vector is an isolated and purified DNA molecule comprising a promoter operatively linked to an coding region that encodes a polypeptide having the ability to catalyze the carboxylation of a biotin carboxyl carrier protein of a cyanobacterium, which coding region is operatively linked to a transcription-terminating region, whereby the promoter drives the transcription of the coding region.

As used herein, the term "operatively linked" means that a promoter is connected to a coding region in such a way that the transcription of that coding region is controlled and regulated by that promoter. Means for operatively linking a promoter to a coding region are well known in the art.

Where an expression vector of the present invention is to be used to transform a cyanobacterium, a promoter is selected that has the ability to drive and regulate expression in cyanobacteria. Promoters that function in bacteria are well known in the art. An exemplary and preferred promoter for the cyanobacterium Anabaena is the glnA gene promoter. An exemplary and preferred promoter for the cyanobacterium Synechococcus is the psbAI gene promoter. Alternatively, the cyanobacterial acc gene promoters themselves can be used.

Where an expression vector of the present invention is to be used to transform a plant, a promoter is selected that has the ability to drive expression in plants. Promoters that function in plants are also well known in the art. Useful in expressing the polypeptide in plants are promoters that are inducible, viral, synthetic, constitutive as described (Poszkowski et al., 1989; Odell et al., 1985), and temporally regulated, spatially regulated, and spatio-temporally regulated (Chau et al., 1989).

A promoter is also selected for its ability to direct the transformed plant cell's or transgenic plant's transcriptional activity to the coding region. Structural genes can be driven by a variety of promoters in plant tissues. Promoters can be near-constitutive, such as the CaMV 35S promoter, or tissue-specific or developmentally specific promoters affecting dicots or monocots.

Where the promoter is a near-constitutive promoter such as CaMV 35S, increases in polypeptide expression are found in a variety of transformed plant tissues (e.g., callus, leaf, seed and root). Alternatively, the effects of transformation can be directed to specific plant tissues by using plant integrating vectors containing a tissue-specific promoter.

An exemplary tissue-specific promoter is the lectin promoter, which is specific for seed tissue. The Lectin protein in soybean seeds is encoded by a single gene (Le1) that is only expressed during seed maturation and accounts for about 2 to about 5% of total seed mRNA. The lectin gene and seed-specific promoter have been fully characterized and used to direct seed specific expression in transgenic tobacco plants (Vodkin et al., 1983; Lindstrom et al., 1990.) An expression vector containing a coding region that encodes a polypeptide of interest is engineered to be under control of the lectin promoter and that vector is introduced into plants using, for example, a protoplast transformation method (Dhir et al., 1991). The expression of the polypeptide is directed specifically to the seeds of the transgenic plant.

A transgenic plant of the present invention produced from a plant cell transformed with a tissue specific promoter can be crossed with a second transgenic plant developed from a plant cell transformed with a different tissue specific promoter to produce a hybrid transgenic plant that shows the effects of transformation in more than one specific tissue.

Exemplary tissue-specific promoters are corn sucrose synthetase 1 (Yang et al., 1990), corn alcohol dehydrogenase 1 (Vogel et al., 1989), corn light harvesting complex (Simpson, 1986), corn heat shock protein (Odell et al., 1985), pea small subunit RuBP Carboxylase (Poulsen et al., 1986; Cashmore et al., 1983), Ti plasmid mannopine synthase (Langridge et al., 1989), Ti plasmid nopaline synthase (Langridge et al., 1989), petunia chalcone isomerase (Van Tunen et al., 1988), bean glycine rich protein 1 (Keller et al., 1989), CaMV 35s transcript (Odell et al., 1985) and Potato patatin (Wenzler et al., 1989). Preferred promoters are the cauliflower mosaic virus (CaMV 35S) promoter and the S-E9 small subunit RuBP carboxylase promoter.

The choice of which expression vector and ultimately to which promoter a polypeptide coding region is operatively linked depends directly on the functional properties desired, e.g., the location and timing of protein expression, and the host cell to be transformed. These are well known limitations inherent in the art of constructing recombinant DNA molecules. However, a vector useful in practicing the present invention is capable of directing the expression of the polypeptide coding region to which it is operatively linked.

Typical vectors useful for expression of genes in higher plants are well known in the art and include vectors derived from the tumor-inducing (Ti) plasmid of *Agrobacterium tumefaciens* described (Rogers et al., 1987). However, several other plant integrating vector systems are known to function in plants including pCaMVCN transfer control vector described (Fromm et al., 1985). Plasmid pCaMVCN (available from Pharmacia, Piscataway, N.J.) includes the cauliflower mosaic virus CaMV 35S promoter.

In preferred embodiments, the vector used to express the polypeptide includes a selection marker that is effective in a plant cell, preferably a drug resistance selection marker. One preferred drug resistance marker is the gene whose expression results in kanamycin resistance; i.e., the chimeric gene containing the nopaline synthase promoter, Tn5 neomycin phosphotransferase II and nopaline synthase 3' nontranslated region described (Rogers et al., 1988).

RNA polymerase transcribes a coding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA).

Means for preparing expression vectors are well known in the art. Expression (transformation vectors) used to transform plants and methods of making those vectors are described in U.S. Pat. Nos. 4,971,908, 4,940,835, 4,769,061 and 4,757,011, the disclosures of which are incorporated herein by reference. Those vectors can be modified to include a coding sequence in accordance with the present invention.

A variety of methods has been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

A coding region that encodes a polypeptide having the ability to catalyze the carboxylation of a biotin carboxyl carrier protein of a cyanobacterium is preferably a biotin carboxylase enzyme of a cyanobacterium, which enzyme is a subunit of acetyl-CoA carboxylase and participates in the carboxylation of acetyl-CoA. In a preferred embodiment, such a polypeptide has the amino acid residue sequence of SEQ ID NO:6 or SEQ ID NO:8, or a functional equivalent of those sequences. En accordance with such an embodiment, a coding region comprises the entire DNA sequence of SEQ ID NO:5 or the DNA sequence of SEQ ID NO:5 comprising the Anabaena accC gene. Alternatively, a coding region comprises the entire DNA sequence of SEQ ID NO:7 or the DNA sequence of SEQ ID NO:7 comprising the Synechococcus accC gene.

En another embodiment, an expression vector comprises a DNA segment that encodes a biotin carboxyl carrier protein of a cyanobacterium. That biotin carboxyl carrier protein preferably includes the amino acid residue sequence of SEQ ID NO:2 or SEQ ID NO:4, or functional equivalents thereof. In accordance with such an embodiment, a coding region comprises the entire DNA sequence of SEQ ED NO:1 or the DNA sequence of SEQ ID NO:1 comprising the Anabaena accB gene. Alternatively, a coding region comprises the entire DNA sequence of SEQ ED NO:3 or the DNA sequence of SEQ ID NO:3 comprising the Synechococcus accB gene.

In another embodiment, an expression vector comprises a DNA segment that encodes a carboxyltransferase protein of a cyanobacterium. That carboxyltransferase protein preferably includes a CTα or CTβ subunit, and preferably includes the amino acid residue sequence of SEQ ID NO:12, or a functional equivalent thereof. In accordance with such an embodiment, a coding region comprises the entire DNA sequence of SEQ ID NO:11 or the DNA sequence of SEQ ID NO:11 comprising the Synechococcus accA gene.

In still yet another embodiment, an expression vector comprises a coding region that encodes a plant polypeptide having the ability to catalyze the carboxylation of acetyl-CoA. Such a plant polypeptide is preferably a monocotyledonous or a dicotyledonous plant acetyl-CoA carboxylase enzyme. A preferred monocotyledonous plant polypeptide encoded by such a coding region is preferably wheat ACC, which ACC includes the amino acid residue sequence of SEQ ID NO:10 or a functional equivalent thereof. A preferred coding region includes the DNA sequence of SEQ ID NO:9. Alternatively, a preferred dicotyledonous plant ACC, such as canola ACC, is also preferred. Such an ACC enzyme is encoded by the DNA segment of SEQ ID NO:19 and has the amino acid sequence of SEQ ID NO:20.

E. Polypeptides

The present invention provides novel polypeptides that define a whole or a portion of an ACC of a cyanobacterium or a plant. In one embodiment, thus, the present invention provides an isolated polypeptide having the ability to catalyze the carboxylation of a biotin carboxyl carrier protein of a cyanobacterium such as Anabaena or Synechococcus. Preferably, a biotin carboxyl carrier protein from Anabaena includes the amino acid sequence of SEQ ID NO:2, with such amino acid sequence listing encoded by the DNA segment of SEQ ID NO:1. Preferably, a biotin carboxyl carrier protein from Synechococcus includes the amino acid sequence of SEQ ID NO:4, with such amino acid sequence listing encoded by the DNA segment of SEQ ID NO:2.

In another embodiment, the present invention provides an isolated polypeptide comprising a biotin carboxylase protein of a cyanobacterium such as Anabaena or Synechococcus. Preferably, a biotin carboxylase protein from Anabaena includes the amino acid sequence of SEQ ID NO:6, with such amino acid sequence listing encoded by the DNA segment of SEQ ID NO:5. Preferably, a biotin carboxylase protein from Synechococcus includes the amino acid sequence of SEQ ID NO:8, with such amino acid sequence listing encoded by the DNA segment of SEQ ID NO:7.

In another embodiment, the present invention provides an isolated polypeptide comprising a carboxyltransferase protein of a cyanobacterium such as Synechococcus. Preferably, a carboxyltransferase protein comprises a CTα or CTβ subunit and includes the amino acid sequence of SEQ ID NO:12, with such amino acid sequence listing encoded by the DNA segment of SEQ ID NO:11.

In another embodiment, the present invention contemplates an isolated and purified plant polypeptide having a molecular weight of about 220 kDa, dimers of which have the ability to catalyze the carboxylation of acetyl-CoA. Such a polypeptide preferably includes the amino acid residue sequence of SEQ ED NO:10, with such amino acid sequence listing encoded by the DNA segment of SEQ ID NO:9. Alternatively the present invention provides an isolated and purified plant polypeptide from canola which has the ability to catalyze the carboxylation of acetyl-CoA. Such a polypeptide preferably includes the amino acid residue sequence of SEQ ID NO:20, with such amino acid sequence listing encoded by the DNA segment of SEQ ID NO:19.

F. Transformed or Transgenic Cells or Plants

A cyanobacterium, a yeast cell, or a plant cell or a plant transformed with an expression vector of the present invention is also contemplated. A transgenic cyanobacterium, yeast cell, plant cell or plant derived from such a transformed or transgenic cell is also contemplated. Means for transforming cyanobacteria and yeast cells are well known in the art. Typically, means of transformation are similar to those well known means used to transform other bacteria or yeast such as *E. coli* or *Saccharomyces cerevisiae*. Synechococcus can be transformed simply by incubation of log-phase cells with DNA. (Golden et al., 1987).

Methods for DNA transformation of plant cells include Agrobacterium-mediated plant transformation, protoplast transformation, gene transfer into pollen, injection into reproductive organs, injection into immature embryos and particle bombardment. Each of these methods has distinct advantages and disadvantages. Thus, one particular method of introducing genes into a particular plant strain may not necessarily be the most effective for another plant strain, but it is well known which methods are useful for a particular plant strain.

There are many methods for introducing transforming DNA segments into cells, but not all are suitable for delivering DNA to plant cells. Suitable methods are believed to include virtually any method by which DNA can be introduced into a cell, such as by Agrobacterium infection, direct delivery of DNA such as, for example, by PEG-mediated transformation of protoplasts (Omirulleh et al., 1993), by desiccation/inhibition-mediated DNA uptake, by electroporation, by agitation with silicon carbide fibers, by acceleration of DNA coated particles, etc. In certain embodiments, acceleration methods are preferred and include, for example, microprojectile bombardment and the like.

Technology for introduction of DNA into cells is well-known to those of skill in the art. Four general methods for delivering a gene into cells have been described: (1) chemical methods (Graham and van der Eb, 1973; Zatloukal et al., 1992); (2) physical methods such as microinjection (Capecchi, 1980), electroporation (Wong and Neumann, 1982; (Fromm et al., 1985) and the gene gun (Johnston and Tang, 1994; Fynan et al., 1993); (3) viral vectors (Clapp, 1993; Lu et al., 1993; Eglitis and Anderson, 1988a; 1988b); and (4) receptor-mediated mechanisms (Curiel et al., 1991; 1992; Wagner et al., 1992).

1. Electroporation

The application of brief, high-voltage electric pulses to a variety of animal and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of clones genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

The introduction of DNA by means of electroporation, is well-known to those of skill in the art. In this method, certain cell wall-degrading enzymes, such as pectin-degrading enzymes, are employed to render the target recipient cells more susceptible to transformation by electroporation than untreated cells. Alternatively, recipient cells are made more susceptible to transformation, by mechanical wounding. To effect transformation by electroporation one may employ either friable tissues such as a suspension culture of cells, or embryogenic callus, or alternatively, one may transform immature embryos or other organized tissues directly. One would partially degrade the cell walls of the chosen cells by exposing them to pectin-degrading enzymes (pectolyases) or mechanically wounding in a controlled manner. Such cells would then be recipient to DNA transfer by electroporation, which may be carried out at this stage, and transformed cells then identified by a suitable selection or screening protocol dependent on the nature of the newly incorporated DNA.

2. Microprojectile Bombardment

A further advantageous method for delivering transforming DNA segments to plant cells is microprojectile bombardment. In this method, particles may be coated with nucleic acids and delivered into cells by a propelling force. Exemplary particles include those comprised of tungsten, gold, platinum, and the like.

An advantage of microprojectile bombardment, in addition to it being an effective means of reproducibly stably transforming monocots, is that neither the isolation of protoplasts (Cristou et al.. 1988) nor the susceptibility to Agrobacterium infection is required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with corn cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing damage inflicted on the recipient cells by projectiles that are too large.

For the bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus which express the exogenous gene product 48 hours post-bombardment often range from 1 to 10 and average 1 to 3.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

Accordingly, it is contemplated that one may wish to adjust various of the bombardment parameters in small scale studies to fully optimize the conditions. One may particularly wish to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated plant integrating vectors to introduce DNA into plant cells is well known in the art. See, for example, the methods described (Fraley et al., 1985; Rogers et al., 1987). Further, the integration of the Ti-DNA is a relatively precise process resulting in few rearrangements. The region of DNA to be transferred is defined by the border sequences, and intervening DNA is usually inserted into the plant genome as described (Spielmann et al., 1986; Jorgensen et al., 1987).

Modern Agrobacterium transformation vectors are capable of replication in *E. coli* as well as Agrobacterium, allowing for convenient manipulations as described (Klee et al., 1985). Moreover, recent technological advances in vectors for Agrobacterium-mediated gene transfer have improved the arrangement of genes and restriction sites in the vectors to facilitate construction of vectors capable of expressing various polypeptide coding genes. The vectors described (Rogers et al., 1987), have convenient multi-linker regions flanked by a promoter and a polyadenylation site for direct expression of inserted polypeptide coding genes and are suitable for present purposes. In addition, Agrobacterium containing both armed and disarmed Ti genes can be used for the transformations. In those plant strains where Agrobacterium-mediated transformation is efficient, it is the method of choice because of the facile and defined nature of the gene transfer.

Agrobacterium-mediated transformation of leaf disks and other tissues such as cotyledons and hypocotyls appears to be limited to plants that Agrobacterium naturally infects. Agrobacterium-mediated transformation is most efficient in dicotyledonous plants. Few monocots appear to be natural hosts for Agrobacterium, although transgenic plants have been produced in asparagus using Agrobacterium vectors as described (Bytebier et al., 1987). Therefore, commercially important cereal grains such as rice, corn, and wheat must usually be transformed using alternative methods. However, as mentioned above, the transformation of asparagus using Agrobacterium can also be achieved (see, for example, (Bytebier et al., 1987).

A transgenic plant formed using Agrobacterium transformation methods typically contains a single gene on one chromosome. Such transgenic plants can be referred to as being heterozygous for the added gene. However, inasmuch as use of the word "heterozygous" usually implies the presence of a complementary gene at the same locus of the second chromosome of a pair of chromosomes, and there is no such gene in a plant containing one added gene as here, it is believed that a more accurate name for such a plant is an independent segregant, because the added, exogenous gene segregates independently during mitosis and meiosis.

More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants produced for enhanced carboxylase activity relative to a control (native, non-transgenic) or an independent segregant transgenic plant.

It is to be understood that two different transgenic plants can also be mated to produce offspring that contain two independently segregating added, exogenous genes. Selfing of appropriate progeny can produce plants that are homozygous for both added, exogenous genes that encode a polypeptide of interest. Back-crossing to a parental plant and out-crossing with a non-transgenic plant are also contemplated.

Transformation of plant protoplasts can be achieved using methods based on calcium phosphate precipitation, polyethylene glycol treatment, electroporation, and combinations of these treatments (see, for example, Potrykus et al., 1985; Lorz et al., 1985; From et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts are described (Fujimura et al., 1985; Toriyama et al., 1986; Yamada et al., 1986; Abdullah et al., 1986).

To transform plant strains that cannot be successfully regenerated from protoplasts, other ways to introduce DNA into intact cells or tissues can be utilized. For example, regeneration of cereals from immature embryos or explants can be effected as described (Vasil, 1988). In addition, "particle gun" or high-velocity microprojectile technology can be utilized. (Vasil, 1992).

Using that latter technology, DNA is carried through the cell wall and into the cytoplasm on the surface of small metal particles as described (Klein et al., 1987; Klein et al., 1988; McCabe et al., 1988). The metal particles penetrate through several layers of cells and thus allow the transformation of cells within tissue explants.

Thus, the amount of a gene coding for a polypeptide of interest (i.e., a polypeptide having carboxylation activity) can be increased in monocotyledonous plants such as corn by transforming those plants using particle bombardment methods (Maddock et al., 1991). By way of example, an expression vector containing an coding region for a dicotyledonous ACC and an appropriate selectable marker is transformed into a suspension of embryonic maize (corn) cells using a particle gun to deliver the DNA coated on microprojectiles. Transgenic plants are regenerated from transformed embryonic calli that express ACC. Particle bombardment has been used to successfully transform wheat (Vasil et al., 1992).

DNA can also be introduced into plants by direct DNA transfer into pollen as described (Zhou et al., 1983; Hess, 1987; Luo et al., 1988). Expression of polypeptide coding genes can be obtained by injection of the DNA into reproductive organs of a plant as described (Pena et al., 1987). DNA can also be injected directly into the cells of immature embryos and the rehydration of desiccated embryos as described (Neuhaus et al., 1987; Benbrook et al., 1986).

The development or regeneration of plants from either single plant protoplasts or various explants is well known in the art (Weissbach and Weissbach, 1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a polypeptide of interest introduced by Agrobacterium from leaf explants can be achieved by methods well known in the art such as described (Horsch et al., 1985). In this procedure, transformants are cultured in the presence of a selection agent and in a medium that induces the regeneration of shoots in the plant strain being transformed as described (Fraley et al., 1983).

This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

Preferably, the regenerated plants are self-pollinated to provide homozygous transgenic plants, as discussed before. Otherwise, pollen obtained from the regenerated plants is crossed to seed-grown plants of agronomically important, preferably inbred lines. Conversely, pollen from plants of those important lines is used to pollinate regenerated plants.

A transgenic plant of the present invention containing a desired polypeptide is cultivated using methods well known to one skilled in the art. Any of the transgenic plants of the present invention can be cultivated to isolate the desired ACC or fatty acids which are the products of the series of reactions of which that catalyzed by ACC is the first.

A transgenic plant of this invention thus has an increased amount of an coding region (e.g., gene) that encodes a polypeptide of interest. A preferred transgenic plant is an independent segregant and can transmit that gene and its activity to its progeny. A more preferred transgenic plant is homozygous for that gene, and transmits that gene to all of its offspring on sexual mating.

Seed from a transgenic plant is grown in the field or greenhouse, and resulting sexually mature transgenic plants are self-pollinated to generate true breeding plants. The progeny from these plants become true breeding lines that are evaluated for, by way of example, herbicide resistance, preferably in the field, under a range of environmental conditions.

The commercial value of a transgenic plant with increased herbicide resistance or with altered fatty acid production is enhanced if many different hybrid combinations are available for sale. The user typically grows more than one kind of hybrid based on such differences as time to maturity, standability or other agronomic traits. Additionally, hybrids adapted to one part of a country are not necessarily adapted to another part because of differences in such traits as maturity, disease and herbicide resistance. Because of this, herbicide resistance is preferably bred into a large number of parental lines so that many hybrid combinations can be produced.

G. Process of Increasing Herbicide Resistance

Herbicides such as aryloxyphenoxypropionates and cyclohexane-1,3-dione derivatives inhibit the growth of monocotyledonous weeds by interfering with fatty acid biosynthesis of herbicide sensitive plants. ACC is the target enzyme for those herbicides. Dicotyledonous plants, other eukaryotic organisms and prokaryotic organisms are resistant to those compounds.

Thus, the resistance of sensitive monocotyledonous plants to herbicides can be increased by providing those plants with ACC that is not sensitive to herbicide inhibition. The present invention therefore provides a process of increasing the herbicide resistance of a monocotyledonous plant comprising transforming the plant with a DNA molecule comprising a promoter operatively linked to a coding region that encodes a herbicide resistant polypeptide having the ability to catalyze the carboxylation of acetyl-CoA, which coding region is operatively linked to a transcription-terminating region, whereby the promoter is capable of driving the transcription of the coding region in a monocotyledonous plant.

Preferably, a herbicide resistant polypeptide, a dicotyledonous plant polypeptide such as an acetyl-CoA carboxylase enzyme from soybean, rape, sunflower, tobacco, Arabidopsis, petunia, canola, pea, bean, tomato, potato, lettuce, spinach, alfalfa, cotton or carrot, or functional equivalent thereof. A promoter and a transcription-terminating region are preferably the same as set forth above.

Transformed monocotyledonous plants can be identified using herbicide resistance. A process for identifying a transformed monocotyledonous plant cell involves transforming the monocotyledonous plant cell with a DNA molecule that encodes a dicotyledonous acetyl-CoA carboxylase enzyme, and determining the resistance of the plant cell to a herbicide and thereby the identification of the transformed monocotyledonous plant cell. Means for transforming a monocotyledonous plant cell are the same as set forth above.

The resistance of a transformed plant cell to a herbicide is preferably determined by exposing such a cell to an effective herbicidal dose of a preselected herbicide and maintaining that cell for a period of time and under culture conditions sufficient for the herbicide to inhibit ACC, alter fatty acid biosynthesis or retard growth. The effects of the herbicide can be studied by measuring plant cell ACC activity, fatty acid synthesis or growth.

An effective herbicidal dose of a given herbicide is that amount of the herbicide that retards growth or kills plant cells not containing herbicide-resistant ACC or that amount of a herbicide known to inhibit plant growth. Means for determining an effective herbicidal dose of a given herbicide are well known in the art. Preferably, a herbicide used in such a process is an aryloxyphenoxypropionate or cyclohexanedione herbicide.

H. Process of Altering ACC Activity

ACC catalyzes the carboxylation of acetyl-CoA. Thus, the carboxylation of acetyl-CoA in a cyanobacterium or a plant can be altered by, for example, increasing an ACC gene copy number or changing the composition (e.g., nucleotide sequence) of an ACC gene. Changes in ACC gene composition may alter gene expression at either the transcriptional or translational level. Alternatively, changes in gene composition can alter ACC function (e.g., activity, binding) by changing primary, secondary or tertiary structure of the enzyme. By way of example, certain changes in ACC structure are associated with changes in the resistance of that altered ACC to herbicides. The copy number of such a gene can be increased by transforming a cyanobacterium or a plant cell with an appropriate expression vector comprising a DNA molecule that encodes ACC.

In one embodiment, therefore, the present invention contemplates a process of altering the carboxylation of acetyl-CoA in a cell comprising transforming the cell with a DNA molecule comprising a promoter operatively linked to a coding region that encodes a polypeptide having the ability to catalyze the carboxylation of acetyl-CoA, which coding region is operatively linked to a transcription-terminating region, whereby the promoter is capable of driving the transcription of the coding region in the cyanobacterium.

In a preferred embodiment, a cell is a cyanobacterium or a plant cell, a polypeptide is a cyanobacterial ACC or a plant ACC. Exemplary and preferred expression vectors for use in such a process are the same as set forth above.

I. Determining Herbicide Resistance Inheritability

In yet another aspect, the present invention provides a process for determining the inheritance of plant resistance to herbicides of the aryloxyphenoxypropionate or cyclohexanedione class. That process involves measuring resistance to herbicides of the aryloxyphenoxypropionate or cyclohexanedione class in a parental plant line and in progeny of the parental plant line and detecting the presence of a DNA segment encoding ACC in such plants.

The inheritability of phenotypic traits such as herbicide resistance can be determined using RFLP analysis. Restriction fragment length polymorphisms (RFLPs) are due to sequence differences detectable by lengths of DNA fragments generated by digestion with restriction enzymes and typically revealed by agarose gel electrophoresis. There are large numbers of restriction endonucleases available, characterized by their recognition sequences and source. From these studies, it is possible to correlate herbicide resistance with a particular DNA fragment and analyze the inheritance of such resistance in progeny plants.

In a preferred embodiment, the herbicide resistant variant of acetyl-CoA carboxylase is a dicotyledonous plant acetyl-CoA carboxylase enzyme or a portion thereof. In another preferred embodiment, the herbicide resistant variant of acetyl-CoA carboxylase is a mutated monocotyledonous plant acetyl-CoA carboxylase that confers herbicide resistance or a hybrid acetyl-CoA carboxylase comprising a portion of a dicotyledonous plant acetyl-CoA carboxylase, a portion of a monocotyledonous plant acetyl-CoA carboxylase or one or more domains of a cyanobacterial acetyl-CoA carboxylase.

Restriction fragment length polymorphism analyses are conducted, for example, by Native Plants Incorporated (NPI). This service is available to the public on a contractual basis. For this analysis, the genetic marker profile of the parental inbred lines is determined. If parental lines are essentially homozygous at all relevant loci (i.e., they should have only one allele at each locus), the diploid genetic marker profile of the hybrid offspring of the inbred parents should be the sum of those parents, e.g., if one parent had the allele A at a particular locus, and the other parent had B, the hybrid AB is by inference.

Probes capable of hybridizing to specific DNA segments under appropriate conditions are prepared using standard techniques well known to those skilled in the art. The probes are labelled with radioactive isotopes or fluorescent dyes for ease of detection. After restriction fragments are separated by size, they are identified by hybridization to the probe. Hybridization with a unique cloned sequence permits the identification of a specific chromosomal region (locus). Because all alleles at a locus are detectable, RFLP's are co-dominant alleles. They differ from some other types of markers, e.g., from isozymes, in that they reflect the primary DNA sequence, they are not products of transcription or translation.

J. Oil Content of Seeds

Manipulation of the oil content and quality of seeds may benefit from knowledge of this gene's structure and regulation. Understanding the basis of resistance to herbicides, on the other hand, will be useful for future attempts to construct transgenic grasses and to provide crop plants such as wheat with selective resistance.

Genes of the present invention may be introduced into plants, particularly monocotyledonous plants, particularly commercially important grains. A wide range of novel transgenic plants produced in this manner may be envisioned depending on the particular constructs introduced into the transgenic plants. The largest use of grain is for feed or food. Introduction of genes that alter the composition of the grain may greatly enhance the feed or food value.

The introduction of genes encoding ACC may alter the oil content of the grain, and thus may be of significant value. Increases in oil content may result in increases in metabolizable-energy-content and density of the seeds for uses in feed and food. The introduction of genes such as ACC which encode rate-limiting enzymes in fatty acid biosynthesis, or replacement of these genes through gene disruption or deletion mutagenesis could have significant impact on the quality and quantity of oil in such transgenic plants.

Likewise, the introduction of the ACC genes of the present invention may also alter the balance of fatty acids present in the oil providing a more healthful or nutritive feedstuff. Alternatively, oil properties may also be altered to improve its performance in the production and use of cooking oil, shortenings, lubricants or other oil-derived products or improvement of its health attributes when used in the food-related applications. Such changes in oil properties may be achieved by altering the type, level, or lipid arrangement of the fatty acids present in the oil. This in turn may be accomplished by the addition of genes that encode enzymes that catalyze the synthesis of novel fatty acids and the lipids possessing them or by increasing levels of native fatty acids while possibly reducing levels of precursors.

Alternatively, introduction of DNA segments which are complementary to the DNA segments disclosed herein into plant cells may bring about a decrease in ACC activity in vivo and lower the level of fatty acid biosynthesis in such transformed cells. Therefore, transgenic plants containing such novel constructs may be important due to their decreased oil content in such cells. Introduction of specific mutations in either the DNA segments disclosed, or in their complements, may result in transformed plants having intermediate ACC activity.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Cloning and Sequencing of the Anabaena acc Genes

1. Biotin Carboxylase (accC)

The gene for the BC subunit was cloned with a fragment of the *E. coli* fabG gene as a heterologous hybridization probe. Southern analysis of Anabaena sp. strain PCC 7120 DNA digested with various restriction enzymes, carried out at low stringency (57° C., 1M NaCl, GeneScreen Plus® membrane [DuPont]) in accordance with the manufacturer's protocol, with an SstII-PstI fragment consisting of ~90% of the coding region of the fabG gene from *E. coli* as a probe revealed, in each case, only one strongly hybridizing restriction fragment. The 3.1-kb HindIII fragment identified by this probe in the Anabaena sp. strain PCC 7120 DNA digest was purified by gel electrophoresis and then was digested with NheI, yielding a 1.6-kb NheI-HindIII fragment that hybridized with the same fabG probe. The 1.6-kb fragment was purified by gel electrophoresis and cloned into XbaI-HindIII-digested pUC18. The ends of the insert were sequenced.

A fragment of an open reading frame coding for a polypeptide with very high similarity to an internal sequence of *E. coli* BC was found at the NheI end of the insert. This result indicated that the 3.1-kb HindIII fragment contained the entire Anabaena sp. strain PCC 7120 BC gene. The 1.6-kb Anabaena sp strain PCC 7120 DNA fragment was then used as a probe to screen, at high stringency (65° C., 1M NaCl), a cosmid library of Anabaena sp. strain PCC 7120 DNA in the cosmid vector pWB79 (Charng et al., 1992), constructed by W. J. Buikema (University of Chicago) with a sized partial HindIII digest of chromosomal DNA. Five cosmids containing overlapping fragments of Anabaena sp. strain PCC 7120 DNA were found in the 1,920-member bank, all of which contained the same size HindIII and NheI fragments as those identified by the *E. coli* probe previously. From one of the cosmids, the 3.1-kb HindIII fragment was subcloned into pUC 18 and sequenced.

Nucleotide sequences of both strands were determined on double-stranded templates by the dideoxy chain termination method with Sequenase (United States Biochemicals). Sets of nested deletions generated with an Erase-a-Base kit (Promega) as well as specific primers were used for sequencing. The 3065-nucleotide DNA segment comprising the Anabaena accC gene is given in SEQ ID NO:5. The 477-amino acid translation of the accC gene encoding the Anabaena BC protein is given in SEQ ID NO:6.

2. Biotin Carboxyl Carrier Protein (accB)

A different approach had to be used to clone the Anabaena sp. strain PCC 7120 BCCP gene. An earlier attempt to clone the gene with a fragment of *E. coli* DNA containing the fabE gene as a heterologous hybridization probe failed. Furthermore, analysis of the sequence (~1.3-kb) located upstream of the Anabaena sp. strain PCC 7120 BC gene revealed no open reading frame corresponding to BCCP, in contrast to the *E. coli* gene organization in which the BCCP gene is located immediately upstream of the BC gene. The BCCP gene was cloned by PCR™ amplification.

The N-terminal amino acid sequence of BCCP was used to design an upstream PCR™ primer. The downstream primer was targeted to the conserved sequence encoding the biotinylation site. The primers had the following structure:

Amino acid sequence LDFNEIR (SEQ ID NO:22)
Primer 1 5'-GCTCTAGAYTTYAAYGARATHMG-3' (SEQ ID NO:23)
Amino acid sequence NMKMX (SEQ ID NO:24) (N=V or A)
Primer II 3'-CRNTACTTYTACNWCTTAAGCT-5' (SEQ ID NO:25)

where Y=T or C; R=A or G; M=C or A; H=A, C, or T; W=A or T; N=T, C, A, or G.

PCR™ was carried out as described in the GeneAmp® kit manual (Perkin-Elmer Cetus). All components of the PCR™ except the Taq DNA polymerase were incubated for 3 to 5 min at 95° C. The PCR™ was then initiated by the addition of polymerase. Amplification was for 45 cycles, each 1 min at 95° C., 1 min at 42 to 45° C., and 2 min at 72° C., with 0.5 to 1.0 μg of template DNA per ml and 50 μg of each primer per ml. The PCR™ amplification yielded a product ~450 bp in size (i.e., the correct size for the anticipated fragment of the Anabaena sp. strain PCC 7120 BCCP gene deduced from the *E. coli* sequence and allowing for a 60- to 90-nucleotide addition due to the polypeptide length difference). The PCR™ product was cloned into the Invitrogen vector pCR1000 with the A/T tail method and was sequenced to confirm its identity.

The fragment of the Anabaena sp. strain PCC 7120 BCCP gene was then used as a probe to identify cosmids that contain the entire gene and flanking DNA. Three such cosmids were detected in a 1,920-member library (same as described above). A 4.2-kb XbaI fragment containing the BCCP gene was subcloned into pBluescriptII®, and its HindIII-NheI fragment was sequenced with specific primers as described above. The 1458-nucleotide DNA segment comprising the Anabaena accB gene is given in SEQ ID NO:1. The 182-amino acid translation of the accB gene encoding the Anabaena BCCP is given in SEQ ID NO:2.

The amino acid sequence deduced from the DNA sequence of the BCCP gene exactly matches the N-terminal sequence obtained for purified protein. Likely translation initiation codons were identified by comparison with *E. coli*. For the BC gene, the AUG start codon is not preceded by an obvious ribosome-binding site. There is a stop codon in the same open reading frame one codon upstream from the AUG codon, excluding the possibility of additional amino acids at the N terminus. The GUG start codon for BCCP immediately precedes codons for the amino acids identified by protein sequencing of the N terminus of purified BCCP. A putative 5-nucleotide ribosome-binding site, GAGGU, is located 11 nucleotides upstream of the GUG codon. The open reading frame extends further upstream of the GUG codon (for about 60 codons), but there are no AUG or GUG codons that could serve as start sties from translation. This excludes the possibility that the purified BCCP polypeptide lacks more than one amino acid (Met) because of rapid proteolytic degradation.

Structural similarities deduced from the available amino acid sequences suggest strong evolutionary conservation among BCs (Al-Feel et al., 1992; Knowles, 1989; Lopez-Casillas et al., 1988; Samols et al., 1988; Takai et al., 1988). Comparison of the amino acid sequence of the BC domain defined as the part of the sequence between amino acids Lys-5 and Phe-432 of Anabaena sp. strain PCC 7120 BC, the two outermost amino acids present in all or all but one of the compared sequences, revealed that all highly conserved amino acid residues identified before are present in Anabaena sp. strain PCC 7120 BC, including the ATP binding site motif and the conserved sequence including Cys-230 as a part of the bicarbonate binding site. The identity between the amino acid sequence of the Anabaena sp. strain PCC 7120 BC domain (based on the best multiple alignment) and that of rat (Lopez-Casillas et al., 1988), chicken (Takai et al., 1988), yeast (Al-Feel et al., 1992), and wheat ACCs was no more than 32 to 37%. Mitochondrial enzymes, rat propionyl-CoA carboxylase (Browner et al., 1989) and yeast pyruvate carboxylase (Lim et al., 1988), are only 45 to 47% identical. Similarities with carbamoyl-phosphate synthetases observed for other BCs (Knowles, 1989; Li and Cronan, 1992; Lopez-Casillas et al., 1988; Samols et al., 1988; Takai et al., 1988) are also evident for Anabaena sp. strain PCC 7120 BC.

Anabaena sp. strain PCC 7120 BCCP is unique with its biotinylation site, the result of a single A-to-C base change resulting in a Met-to-Leu substitution. This base change explains the highly variable yield of the PCR™ amplification with primer II. The structure of this part of the BCCP gene was confirmed by sequencing the corresponding PCR™-cloned fragment of Anabaena sp. strain PCC 7120 DNA. The result is not entirely surprising, because in vitro analysis of mutants of the 1.3S subunit of transcarboxylase from *Propionibacterium shermanii*, in which the same Met-to-Leu change was introduced, showed that this methionine residue is not essential for efficient biotinylation of the apoprotein (Shenoy et al., 1992). Urea carboxylase contains Ala at this position. The conserved motif may be required for some other functions. Furthermore, it was suggested that the distance between the biotinylated lysine residue and the C terminus and the structure of the last two amino acids (hydrophobic one followed by acidic one) are important determinants for the modification of at least some BCCP apoproteins (Shenoy et al., 1992). Two amino acids with the same properties are also found at an analogous position (with respect to the distance from the biotinylation site) of large eukaryotic biotin-dependent carboxylases. Anabaena sp. strain PCC 7120 BCCP also contains those amino acids, but they are separated from the biotinylation site by two additional amino acids. Anabaena sp. strain PCC 7120 BCCP is about 30 amino acids longer than the *E. coli* protein, including a 21-amino-acid insertion near the N terminus. The moderate conservation of the amino acid sequence is reflected by rather low conservation at the nucleotide level (Table 3), which explains whey the *E. coli* BCCP specific probe failed to identify the Anabaena sp. strain PCC 7120 gene.

Comparison of the amino acid sequence encoded by the additional short open reading frame located upstream of the BCCP gene and transcribed in the same direction and sequences deposited in GenBank (release 75) revealed no similar proteins.

3. Northern analysis of the BCCP message

The size of Anabaena sp. strain PCC 7120 BCCP mRNA was established by Northern (RNA) analysis with the PCR-amplified fragment of the gene as a probe. The major hybridizing mRNA is 1.45-kb in size. The two minor species are 1.85 and 2.05-kb in size. All of these are long enough to include the BCCP coding region. The amount of all three mRNAs seems to be higher (about twofold) in cells grown in the absence of combined nitrogen. The 24-h induction time correlates with the onset of nitrogen fixation in heterocysts, differentiated cells that fix nitrogen and have a unique glycolipid envelope containing $C_{26}$ and $C_{28}$ fatty acids (Murata and Nishida, 1987). If the increase of the level of the BCCP mRNA is heterocyst specific, it must be significant because heterocysts in Anabaena sp. strain PCC 7120 filaments are formed only at ~10-cell intervals. This result suggests that ACC may be developmentally regulated in Anabaena sp. strain PCC 7120. Results of some recent experiments indicate that, in bacteria, modulation of ACC activity may indeed play an important role in the overall regulation of the biosynthesis of the cell lipids. It has been demonstrated that the level of transcription of the ACC genes is correlated in *E. coli* with the rate of cellular growth and nutritional upshifts and downshifts (Li and Cronan, 1993). Mutations in the *E. coli* fabGE operon which decrease the rate of phospholipid biosynthesis suppress a null mutation in the htrB gene by restoring the balance between phospholipid biosynthesis and cell growth (Karow et al., 1992). Northern analysis with the 1.6-kb NheI-HindIII fragment as a BC-specific probe repeatedly gave a smeared band pattern which could not be interpreted.

Unlike the BCCP and BC genes of *E. coli* where they are cotranscribed, the BCCP and BC genes of the present invention are separated by at least several kilobases (no overlapping cosmids were seen when the cosmid library was screened with probes specific for BCCP and BC).

EXAMPLE 2

Purification and Characterization of Anabaena BCCP

Western immunoblot analysis of Anabaena sp. strain PCC 7120 proteins with $^{35}$S-streptavidin revealed one biotinylated polypeptide ~25 kDa in size. Although the presence of other, much less abundant biotinylated proteins cannot be strictly ruled out, this result strongly suggests that ACC is the only biotin-dependent enzyme in Anabaena sp. strain PCC 7120, with the BCCP subunit of 19 kDa, the calculated size; 25 kDa as measured by sodium dodecyl sulfate-polyacrylamide gel electrophoresis (SDS-PAGE).

The polypeptide shows a slightly lower mobility than *E. coli* BCCP (22.5 kDa), suggesting that Anabaena sp. strain PCC 7120 BCCP is longer by 20 to 30 amino acids. However, the unusual electrophoretic properties of the *E. coli* protein (Li and Cronan, 1992) make an accurate prediction of the polypeptide length difficult. Separation of Anabaena sp. strain PCC 7120 proteins for Western analysis or sequencing) was by SDS-PAGE with 12.5% separating gels (Sambrook et al., 1989) followed by transfer onto polyvinylidene difluoride membrane (Immobilon-P®; Millipore) in 10 mM sodium 3-(cyclohexylamino)-1-propane-sulfonate buffer (pH 11)-10% methanol. Western blots were blocked with 3% bovine serum albumin solution in 10 mM Tris-HCl (pH 7.5) and 0.9% NaCl and then were incubated for 3 to 16 h with $^{35}$S-streptavidin (Amersham). The blots were washed at room temperature with 0.5% Nonidet P-40™ in 10 mM Tris-HCl (pH 7.5) and 0.9% NaCl.

TABLE 3

COMPARISON OF BC AND BCCP SUBUNITS FROM Anabaena AND *E. coli*

| ACC subunit[a] | No. of amino acids (mol wt)[b] | | % Identity (similarity) |
|---|---|---|---|
| | Anabaena sp. strain PCC 7120 | *E. coli*[c] | |
| BC | | | |
| Protein | 447 (49,076) | 449 | 57(74) |
| DNA[d] | | | 58 |
| BCCP | | | |
| Protein | 182 (19,126) | 156 | 39(65) |
| DNA[d] | | | 41 |

[a]The genes for the two subunits of ACC are unlinked in Anabaena sp. strain PCC 7120; in *E. coli* they are in one operon.
[b]Molecular weight was calculated from amino acid composition.
[c]From Li and Cronan, 1992.
[d]On the basis of amino acid alignment.

BCCP from Anabaena sp. strain PCC 7120 was purified starting with cells from a 3-liter culture grown on BG11 medium (Rippka et al., 1979). Cells were broken by sonication at 0° C. in 30 ml of 0.5 m NaCl-0.1M Tris-HCl (pH 7.5)-14 mM β-mercaptoethanol-0.2 mM phenylmethylsulfonyl fluoride. Insoluble material was removed by centrifugation at 31,000×g for 30 min, and the soluble protein fraction containing BCCP was precipitated by adding solid ammonium sulfate (50% saturation). The pellet was resuspended in 15 ml of 0.2M NaCl-50 mM Tris-HCl (pH 7.5)-10% glycerol-0.5% SDS and then mixed at room temperature for about 18 h with 0.5 ml of streptavidin-agarose suspension (GIBCO BRL). The mixture was loaded onto a column, was washed with about 30 ml of 0.25M NaCl-50 mM Tris-HCl (pH 7.5)-0.5 mM EDTA-0.2% SDS, and then was washed with 5 ml of water. Biotinylated peptides were eluted with 3 ml of 70% formic acid, dried under vacuum, and separated by SDS-PAGE. The N-terminal sequence of the biotin-containing ~25-kDa polypeptide was determined by Edman degradation after transfer to Immobilon-P® as described above. The sequence was PLDFNEIRQL (SEQ ID NO:21).

EXAMPLE 3

Cloning and Characterization of the Synechococcus acc Genes and Purification of the Synechococcus BCCP 1. Biotin Carboxylase (accC)

All carboxylases have a conserved amino acid motif that constitutes the ATP-binding site. A 1.2-kb SstII-PstI fragment (containing the ATP-binding motif) within the *E. coli* accC gene was used as a probe to examine the Synechococcus PCC 7942 genomic DNA by Southern hybridization at 58° C. A strongly hybridizing 0.8-kb BamHI-PstI fragment was detected and subsequently cloned by a two-stage size fractionation method.

Synechococcus PCC 7942 genomic DNA was first digested with BamHI and electrophoresed on an agarose gel. The gel region containing DNA of sizes between 1.6-kb and 3-kb was cut out and purified (using Geneclean II Kit from Bio101). The purified DNA was then digested with PstI and electrophoresed on an agarose gel. The gel region containing DNA of sizes between 0.5-kb and 2-kb was cut out and purified. DNA samples (from each step of purification) were electrophoresed, transferred onto a Genescreen Plus membrane, hybridized with the *E. coli* accC probe to confirm that the homologous DNA fragment was not lost during each purification step. A library of fragments between 0.5-kb and 2-kb was created by cloning the purified fraction of Synechococcus PCC 7942 DNA into vector pBluescript® KS. Ampicillin-resistant and white (i.e., with insert) colonies were selected by plating on LB plates containing ampicillin, X-Gal and IPTG.

A total of 287 ampicillin-resistant, white clones were screened; the plasmid DNA mixture (from pools of 5 white clones per pool) were prepared, doubly-digested with PstI and BamHI, electrophoresed, transferred onto a Genescreen Plus membrane, then hybridized with the *E. coli* accC probe at 58° C. Positive signals appeared on 8 pools. Twelve positive individual clones were identified at the second round of screening. Two (of the 12) positive clones, each with a single fragment inserted, had the inserts sequenced. Both clones had identical inserts. Sequence comparison indicated only about 60% identity at the nucleotide level between the *E. coli* accC gene and the cloned Synechococcus PstI-BamHI fragment. This cloned fragment was then used as a probe to screen a Synechococcus cosmid library. Hybridization of the cosmid library was performed at 65° C. One hybridizing clone was identified and a 2.4-kb BamHI-NheI fragment from this cosmid clone was isolated and sequenced.

The 1362-nucleotide DNA segment comprising the Synechococcus accC gene is given in SEQ ED NO:7. Only one significant open reading frame (ORF) was found. This ORF potentially encodes a protein of 453 amino acids. The complete translated amino acid sequence of the Synechococcus accC gene encoding BC is given in SEQ ID NO:8.

2. Biotin Carboxyl Carrier Protein (accB)

In Synechococcus PCC 7942, the accB gene is not immediately upstream of accC, as it is in *E. coli*. Gene-specific DNA probes from both *E. coli* and Anabaena PCC7120 accB failed to hybridize with the Synechococcus genomic DNA by Southern analysis. A different approach was necessary.

Since biotin carboxyl carrier protein is biotinylated and streptavidin has a strong specific affinity for biotin, streptavidin was used to identify the number of biotin-containing proteins in Synechococcus PCC 7942. The proteins (from a crude whole protein extract) of Synechococcus PCC 7942 were first separated by standard SDS-PAGE method, then transferred onto an Immobilon-P® transfer membrane, which was subsequently incubated with 35S-streptavidin. Only one radioactive band (corresponding to a protein of about 25 kDa) appeared on the autoradiogram. This result suggests that there is only one biotin-containing protein in Synechococcus and its mass is similar to the reported mass of E. coli biotin carboxyl carrier protein, 22,500 Da.

This biotin-containing protein was purified Synechococcus cells were first broken by sonication in a buffer containing NaCl, Tris, glycerol and SDS. The supernatant was separated from cell debris by centrifugation, then followed by a 50% $(NH_4)_2 SO_4$ precipitation. The precipitate was dissolved in the same buffer, and was allowed to bind to streptavidin agarose beads. The bound agarose beads were washed and the bound proteins were eluded with 70% formic acid. The formic acid-eluted portion was dried and washed with water before loading onto an acrylamide gel. After electrophoresis, the proteins were transferred from the gel to an Immobilon-P® transfer membrane. The membrane was stained briefly with Coomassie Brilliant blue dye, destained in a mixture of methanol and acetic acid, and soaked in water for na hour or so before air drying. The band corresponding to the streptavidin-bound protein was cut out and its N-terminal amino acid sequence was determined.

Based on the amino acid sequence from the N-terminus of the Synechococcus biotin-containing protein and the amino acid sequence around the biotinylation site in all other known BCCPs, degenerate oligonucleotide primers were designed for PCR™ amplification studies with Synechococcus genomic DNA. The pair of primers were:

primer LE85'-GCTCTAGACNCARYTNAAYTT-3' (SEQ ID NO:26)
primer LE73'-CRNTACTTYGACNWCTTAAGCT-5' (SEQ ID NO:27)

PCR™ was performed for 40 cycles (each with 1 minute at 95° C., 1 minute at 48° C., 2 minutes at 72° C.), with Cetus Taq polymerase, 0.5 mg/ml of template DNA, 5 mg/ml of primer LE8, 40 mg/ml of primer LE7 and with 1 mM $Mg^{2+}$ final concentration. Under these conditions, a specific PCR™ produce was identified. Sequence analysis of this cloned PCR™ product indicated that it encoded a region of conserved amino acids within accB of Synechococcus PCC 7942 (compared to the amino acid sequences of the biotin carboxyl carrier protein from Anabaena PCC 7120 and E. coli). Using this PCR™ fragment as a probe in Southern hybridization, a positive clone was identified from the Synechococcus cosmid library. A 1.6-kb PstI fragment from this positive cosmid clone was isolated and sequenced.

A 477-nucleotide DNA segment comprising the Synechococcus accB gene is given in SEQ ID NO:3. Only one significant ORF was found. The deduced amino acid sequence at the N-terminus of this ORF matches the earlier determined N-terminal amino acid sequence of the purified Synechococcus biotin-containing protein. The 158-amino acid sequence of the Synechococcus BCCP is given in SEQ ID NO:4. Sequence alignment indicated that the translational product of accB from Synechococcus PCC 7942 is closer to that from Anabaena PCC 7120 than that from E. coli (53% versus 31% amino acid identity).

3. Carboxyltransferase α Subunit (CTα, accA)

A 0.9-kb ClaI-MluI fragment of the E. coli accA gene used as a probe to examine the Synechococcus PCC 7942 genomic DNA by Southern hybridization at 60° C. A strongly hybridizing 1.6-kb PstI fragment was detected and subsequently cloned.

Synechococcus PCC 7942 genomic DNA was digested with PstI and electrophoresed on an agarose gel. The gel region containing DNA of sizes between 1.6 and 2.5-kb was cut out and purified. A size library between 1.6-kb and 2.5-kb was created by cloning the purified fraction of Synechococcus PCC 7942 DNA into vector pBR322. Tetracycline-resistant, but ampicillin-sensitive, colonies (i.e., with insert) were selected by first plating on LB plates containing tetracycline, then scored on plates containing ampicillin.

A total of 800 tetracycline-resistant, but ampicillin-sensitive, clones were screened: the plasmid DNA was prepared, digested (in pools of 5 clones per pool) with PstI, electrophoresed, transferred onto a Genescreen Plus membrane, then hybridized with the E. coli accA probe at 60° C. Positive signals appeared on 3 pools. One positive individual clone, with 2 fragments inserted, was identified at the second round of screening. The positive fragment was isolated and re-cloned. This cloned 1.6-kb PstI fragment was then used as a probe to screen the Synechococcus cosmid library where 9 positive clones were identified. A 5-kb BamHI fragment from one of these 9 clones was isolated and sequenced. DNA sequence analysis of the region indicated a cluster of three ORFs in the same orientation.

The 984-nucleotide DNA segment comprising the Synechococcus accA gene is given in SEQ ID NO:11. The first open reading frame encodes the α subunit of the carboxyltransferase. The 327-amino acid sequence of the Synechococcus ORF is 54% identical to that of the E. coli accA gene. The amino acid sequence of the Synechococcus accA gene encoding CTα is given in SEQ ID NO:12.

4. Carboxyltransferase β Subunit (CTβ, accD)

Oligonucleotide primers, for polymerase chain reaction (PCR™) amplification experiments with Synechococcus genomic DNA, were based on the sequence of ORF326 (which is a homolog of the E. coli accD) from a different cyanobacterium, Synechocystis PCC 6803. The pair of primers were:

LE395'-GAAGATCTTTATGGGCGGTAGTATG-3' (SEQ ID NO:28)
LE403'-GGTCGAAACGGTACAACCTAGGC-5' (SEQ ID NO:29)

PCR™ was run for 40 cycles (each with 1 minute at 95° C., 1 minute at 50° C., 2 minutes at 72° C.), with Boehringer-Mannheim Taq polymerase, 0.5 mg/ml of template DNA, 5 mg/ml of each primer and with 1M $Mg^{2+}$ final concentration. Under these conditions, a specific PCR™ product of 256 bp was identified. Sequence analysis of this cloned PCR™ fragment showed a significant similarity between the Synechococcus and Synechocystis genomic DNAs in the region between the primers. Using this cloned PCR™ product as a probe, 5 positive cosmid clones were identified from the Synechococcus cosmid library by Southern hybridization.

EXAMPLE 4

CLONING AND SEQUENCING OF Triticum aestivum ACC cDNA

A. MATERIALS AND METHODS
1. PCR™ Amplification

Degenerate PCR™ primers were based on the alignment of amino acid sequences of the following proteins (accession numbers in brackets): rat (J03808) and chicken (J03541) ACCs; E. coli (M80458, M79446, X14825, M32214), Anabaena 7120 (L14862, L14863) and Synechococcus 7942 BCs and BCCPs; rat (M22631) and human (X14608) propionylcoenzyme A carboxylase (α subunit); yeast (J03889) pyruvate carboxylase; *Propionibacterium shermanii*

(M111738) transcarboxylase (1.3S subunit) and *Klebsiella pneumonia* (J03885) oxaloacetate decarboxylase (a subunit). Each primer consisted of a 14-nucleotide specific sequence based on the amino acid sequence and a 6- or 8-nucleotide extension at the 5'-end.

Poly(A)+ RNA from 8-day old plants (*Triticum aestivum* var. Era) was used for the synthesis of the first strand of cDNA with random hexamers as primers for AMV reverse transcriptase (Haymerle et al., 1986). Reverse transcriptase was inactivated by incubation at 90° C. and low molecular weight material was removed by filtration. All components of the PCR™ (Cetus/Perkin-Elmer), except the Taq DNA polymerase, were incubated for 3–5 min at 95° C. The PCR™ was initiated by the addition of polymerase. Conditions were optimized by amplification of the BC gene from Anabaena 7120. Amplification was for 45 cycles, each 1 min at 95° C., 1 min at 42–46° C. and 2 min at 72° C. $MgCl_2$ concentration was 1.5 mM. Both the reactions using Anabaena DNA and the single-stranded wheat cDNA as template yielded the expected 440-bp products. The wheat product was separated by electrophoresis on LMP-agarose and reamplified using the same primers and a piece of the LMP-agarose slice as a source of the template. That product, also 440-bp, was cloned into the Invitrogen vector pCR1000 using their A/T tail method, and sequenced.

In eukaryotic ACCs, the BCCP domain is located about 300 amino acids downstream from the end of the BC domain. Therefore, it was possible to amplify the cDNA encoding that interval between the two domains using primers, one from the C-terminal end of the BC domain and the other from the conserved biotinylation site. The expected 1.1-kb product of the first low yield PCR™ with primers III and IV was separated by electrophoresis on LMP-agarose and reamplified by another round of PCR™, then cloned into the Invitrogen vector pCRII® and sequenced. The PCR™ conditions were the same as those described above.

2. Isolation and Analysis of ACC cDNA

A wheat cDNA library (*Triticum aestivum*, var. Tam 107, Hard Red Winter, 13-day light grown seedlings) was purchased from Clontech. This λgt11 library was prepared using both oligo(dT) and random primers. Colony Screen-Plus® (DuPont) membrane was used according to the manufacturers' protocol (hybridization at 65° C. in 1M NaCl and 10% dextran sulfate). The library was first screened with the 1.1-kb PCR™-amplified fragment of ACC-specific cDNA. Fragments of clones 39-1, 45-1 and 24-3 were used in subsequent rounds of screening. In each case, ~2.5×10⁶ plaques were tested. More than fifty clones containing ACC-specific cDNA fragments were purified, and EcoRI fragments of the longest cDNA inserts were subcloned into pBluescriptSK® for further analysis and sequencing. A subset of the clones was sequenced on both strands by the dideoxy chain termination method with Sequenase® (United States Biochemicals) or using the Perkin Elmer/ Applied Biosystems Taq DyeDeoxy Terminator cycle sequencing kit and an Applied Biosystems 373A DNA Sequencer.

3. RNA and DNA

Total RNA from 10-day old wheat plants was prepared as described in (Haymerle et al., 1986). RNA was separated on a glyoxal denaturing gel (Sambrook et al., 1989). Gene-Screen Plus® (DuPont) blots were hybridized in 1M NaCl and 10% dextran sulfate at 65° C. (wheat RNA and DNA) or 58–60° C. (soybean and canola DNA). All cloning, DNA manipulation and gel electrophoresis were as described (Sambrook et al., 1989).

B. RESULTS

A 440-bp cDNA fragment encoding a part of the biotin carboxylase domain of wheat ACC and a 1.1-kb cDNA fragment encoding the interval between the biotin carboxylase domain and the conserved biotinylation site were amplified. These fragments were cloned and sequenced. In fact, three different 1.1-kb products, corresponding to closely related sequences that differ from each other by 1.5%, were identified. The three products most likely represent transcription products of three different genes, the minimum number expected for hexaploid wheat. These two overlapping DNA fragments (total length of 1473 nucleotides) were used to screen a wheat cDNA library. The structure of the DNA region encoding wheat ACC is given in FIG. 1.

2. Isolation and Sequence Analysis of Wheat ACC cDNAs

A set of overlapping cDNA clones covering the entire ACC coding sequence was isolated and a subset of these clones has been sequenced. The nucleotide sequence within overlapped regions of clones 39-1, 20-1 and 45-1 differ at 1.1% of the nucleotides within the total of 2.3 kb of the overlaps. The sequence within the overlap of clones 45-1 and 24-3 is identical. The sequence contains a 2257-amino acid reading frame encoding a protein with a calculated molecular mass of 251 kDa. In wheat germ the active ACC has an apparent molecular mass of ~500 kDa and the individual polypeptides have an apparent molecular mass (measured by SDS-PAGE) of about 220 kDa (Gornicki and Haselkorn, 1993). The 220-kDa protein was also present in both total leaf protein and protein from intact chloroplasts. In fact, it was the major biotinylated polypeptide in the chloroplast protein. The cDNAs (total length 7.4 kb) include 158 bp of the 5'-untranslated and 427 bp of the 3'-untranslated sequence.

The 7360-nucleotide DNA segment comprising the wheat ACC cDNA is given in SEQ ID NO:9. The 2257-amino acid translated wheat ACC sequence is given in SEQ ID NO:10.

3. Northern Analysis of ACC mRNA

Figure 2:
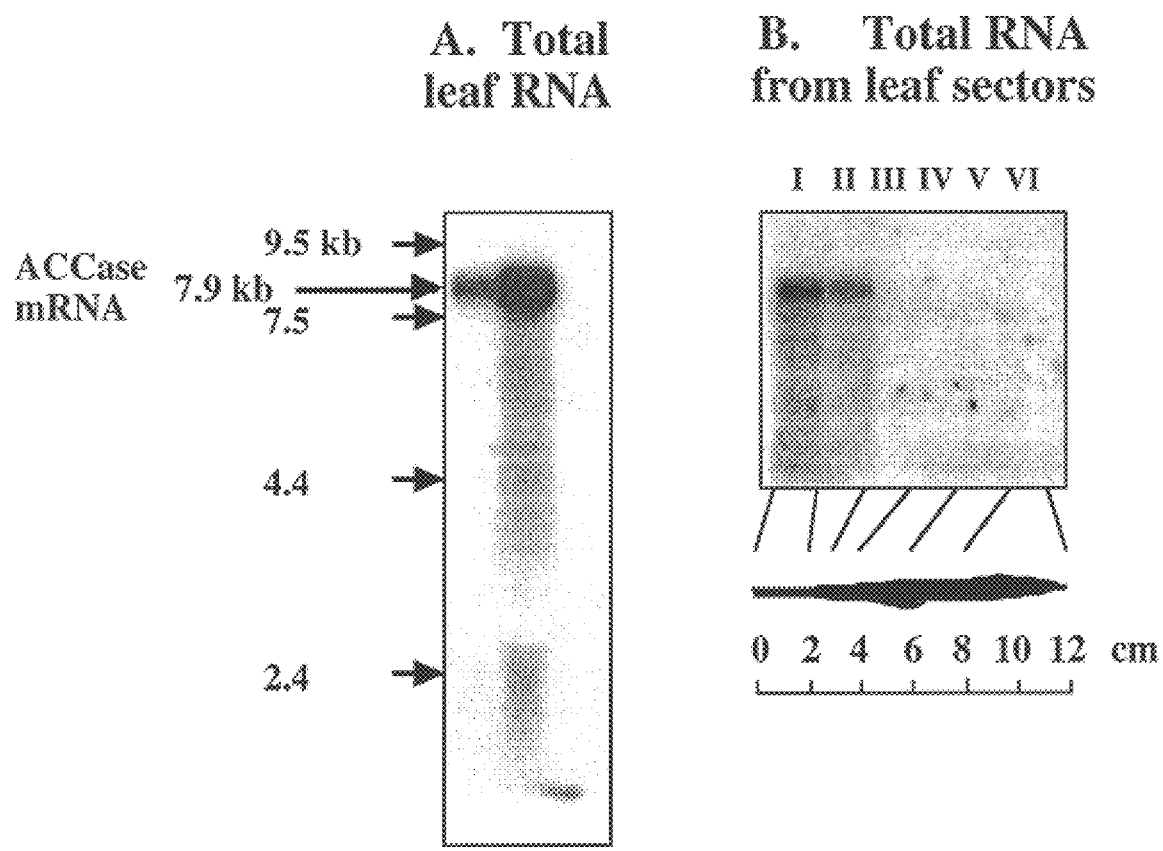
FIG. 2A. Northern analysis of ACC-specific mRNA in whole wheat leaves. 40 and 4 mg of total RNA were used to prepare the Northern blot. The results of hybridization with the 24-3 cDNA probe are shown. Positions of molecular weight markers are indicated by arrows.
FIG. 2B. Northern analysis of ACC-specific mRNA in wheat leaf sectors. 15 mg of total RNA from 10-day old plants were used in each lane. The results of hybridization with the 24-3 cDNA probe are shown.

Northern blots with total RNA from 10–14 day old wheat leaves were probed using different cDNA fragments (the 1.1-kb PCR™-amplified fragment and parts of clones 20-1, 24-3 and 01-4) (FIG. 2A, FIG. 2B). In each case the only hybridizing mRNA species was 7.9 kb in size. This result shows clearly that all the cDNA clones correspond to mRNA of large, eukaryotic ACC and that there are no other closely related biotin-dependent carboxylases, consisting of small subunits that are encoded by smaller mRNAs, in wheat.

Northern analysis of total RNA prepared from different sectors of 10-day old wheat seedlings indicates very high steady-state levels of ACC-specific mRNA in cells of leaf sectors I and II near the basal meristem (FIG. 2B). The ACC mRNA level is significantly higher in sectors I and II than in sectors III–VI (FIG. 2B). This cannot be explained by dilution of specific mRNA by increased levels of total RNA in older cells. Based on published results (Dean and Leech, 1982), the increase in total RNA between sectors I and VI is expected to be only about two-fold.

All cell division occurs in the basal meristem and cells in other sectors are in different stages of development. Differences between these young cells and the mature cells at the tip of the leaf include cell size, number of chloroplasts and amount of total RNA and protein per cell (Dean and Leech, 1982). Expression of some genes is correlated with the cell age (e.g., Lampa et al., 1985). It is not surprising that the level of ACC-specific mRNA is highest in dividing cells and in cells with increasing number of chloroplasts. The burst of ACC mRNA synthesis is necessary to supply enough ACC to meet the demand for malonyl-coenzyme A. The levels of ACC mRNA decrease significantly in older cells where the demand is much lower. The same differences in the level of ACC specific mRNA between cells in different sectors were found in plants grown in the dark and in plants illuminated for one day at the end of the dark period.

4. Southern Analysis of Plant DNA

Figure 3:
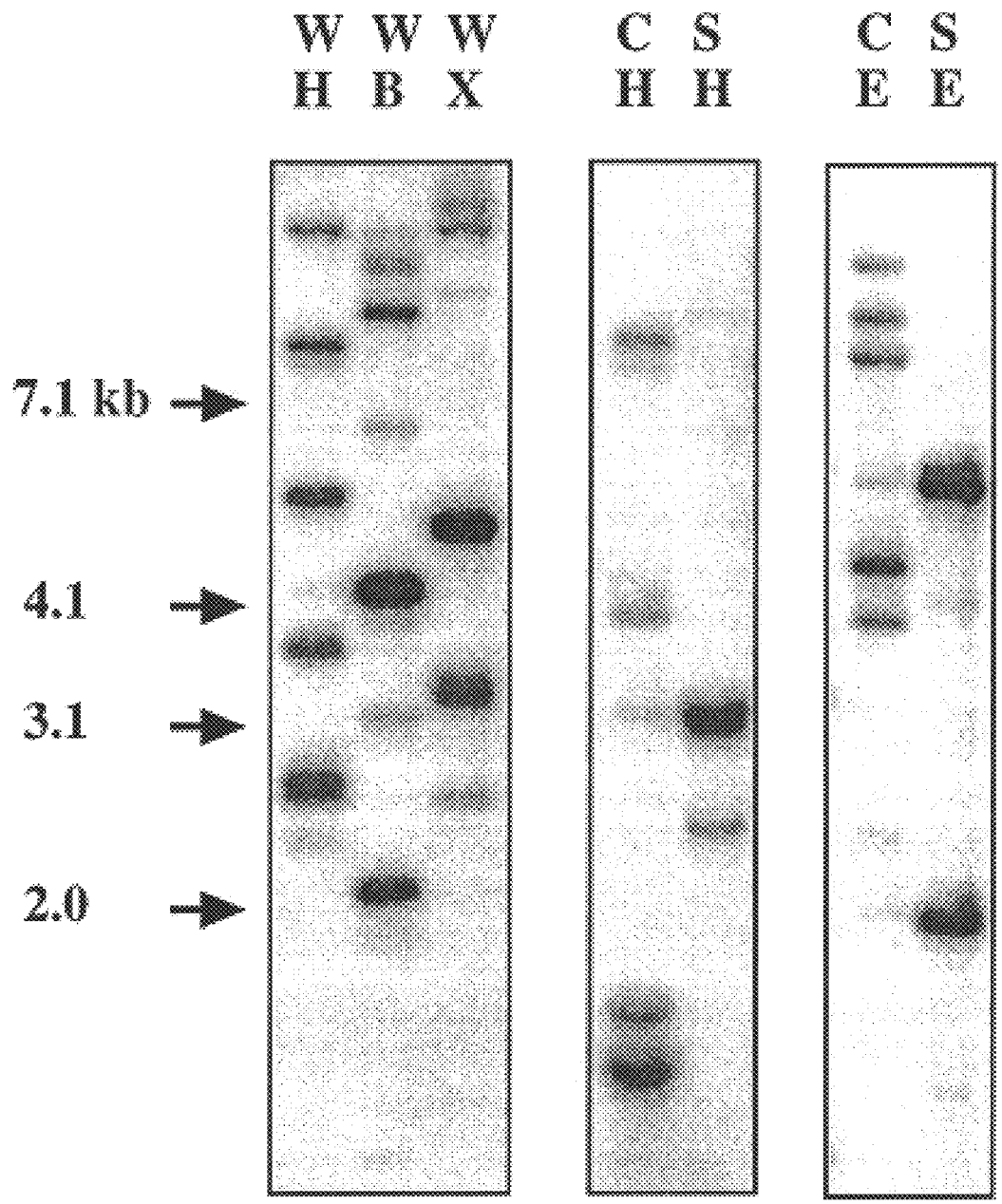
FIG. 3. Southern analysis of wheat (w), canola (c) and soybean (s) DNA using wheat ACC cDNA fragment 24-3 as a hybridization probe. Conditions used for canola and soybean hybridization were less stringent than that used for wheat. H, HindIII; B, BamHI; X, XbaI; E, EcoRI. 8–10 mg of DNA were run in each lane.

Hybridization, under stringent conditions, of wheat total DNA digests with wheat ACC cDNA probes revealed multiple bands (FIG. 3). This was expected due to the hexaploid nature of wheat (Triticum aestivum). Some of the wheat cDNA probes also hybridize with ACC-specific DNA from other plants (FIG. 3). The specificity of this hybridization was demonstrated by sequencing several fragments of canola genomic DNA isolated from a library using wheat cDNA probe 20-1 (FIG. 1) and by Northern blot of total canola RNA using one of the canola genomic clones as a probe. The Northern analysis revealed a large ACC-specific message in canola RNA similar in size to that found in wheat.

5. ACC mRNA

The putative translation start codon was assigned to the first methionine of the open reading frame. An in-frame stop codon is present 21 nucleotides up-stream from this AUG. The nucleotide sequence around this AUG fits quite well with the consensus for a monocot translation initiation site derived from the sequence of 93 genes, except for U at position +4 of the consensus which was found in only 3 of the 93 sequences. The ACC mRNA stop codon UGA is also the most frequently used stop codon found in monocot genes, and the surrounding sequence fits the consensus well.

6. Homologies with Other Carboxylases

A comparison of the wheat ACC amino acid sequence with other ACCs shows sequence conservation among these carboxylases. The sequence of the polypeptide predicted from the cDNA described above was compared with the amino acid sequences of other ACCs, and about 40% identity are with the ACC of rat, diatom and yeast (about 40%). Less extensive similarities are evident with subunits of bacterial ACCs. The amino acid sequence of the most highly conserved domain, corresponding to the biotin carboxylases of prokaryotes, is about 50% identical to the ACC of yeast, chicken, rat and diatom, but only about 27% identical to the biotin carboxylases of E. coli and Anabaena 7120. The biotin attachment site has the typical sequence of eukaryotic ACCs. Several conserved amino acids found in the carboxyltransferase domains previously identified (Li and Cronan, 1992) are also present in the wheat sequence. Surprisingly, none of the four conserved motifs containing serine residues, which correspond to phosphorylation sites in rat, chicken and human ACCs (Ha et al., 1994), is present at a similar position in the wheat polypeptide.

7. Lack of Targeting Sequence in Wheat ACC cDNA

The wheat cDNA does not encode an obvious chloroplast targeting sequence unless this is an extremely short peptide. There are only 12 amino acids preceding the first conserved amino acid found in all eukaryotic ACCs (a serine residue). The conserved core of the BC domain begins about 20 amino acids further down-stream. The apparent lack of a transit peptide poses the question of whether and how the ACC described in this paper is transported into chloroplasts. It was shown recently that the large ACC polypeptide purifies with chloroplasts of wheat and maize (Gornicki and Haselkorn, 1993; Egli et al., 1993). No obvious chloroplast transit peptide between the ER signal peptide and the mature protein was found in diatom ACC either (Roessler and Ohlrogge, 1993).

The number of ACC genes in wheat have been assessed by Southern analysis and by sequence analysis of the 5'- and 3'-untranslated portions of ACC cDNA representing transcripts of different genes. These EDNA fragments may be obtained by PCR™ amplification using the 5'- and 3'-RACE methodology. The genome structure of wheat (Triticum aestivum) suggests the presence of at least three copies of the ACC gene, i.e. one in each ancestral genome. Sequence analysis of the 5'-untranscribed parts of the gene may determine whether any familiar promoter and regulatory elements are present. The structure of introns within the control region and in the 5'-fragment of the coding sequence is also of interest.

The plant ACC genes are full of introns and their transcripts undergo alternative splicing. In some plant genes, introns have been found both within the sequence encoding the transit peptide, and at the junction between the transit peptide and the mature protein.

In plants, variant cytoplasmic and plastid isoenzymes could arise, for example, by alternative splicing or by transcription of two independent genes. This problem is especially intriguing as it was not possible to identify a transit peptide in the sequences of wheat ACC obtained so far. The two possibilities can be distinguished by sequence analysis of the appropriate fragment of the ACC genes (clones from genomic library) and mRNAs (as cDNA). The sequence of these 5'- and 3'-untranscribed and untranslated fragments of the gene are usually significantly different for different alleles so they may also be used as specific probes to follow expression of individual genes.

EXAMPLE 5

ISOLATION AND CHARACTERIZATION OF THE WHEAT ENZYME

Figure 4:
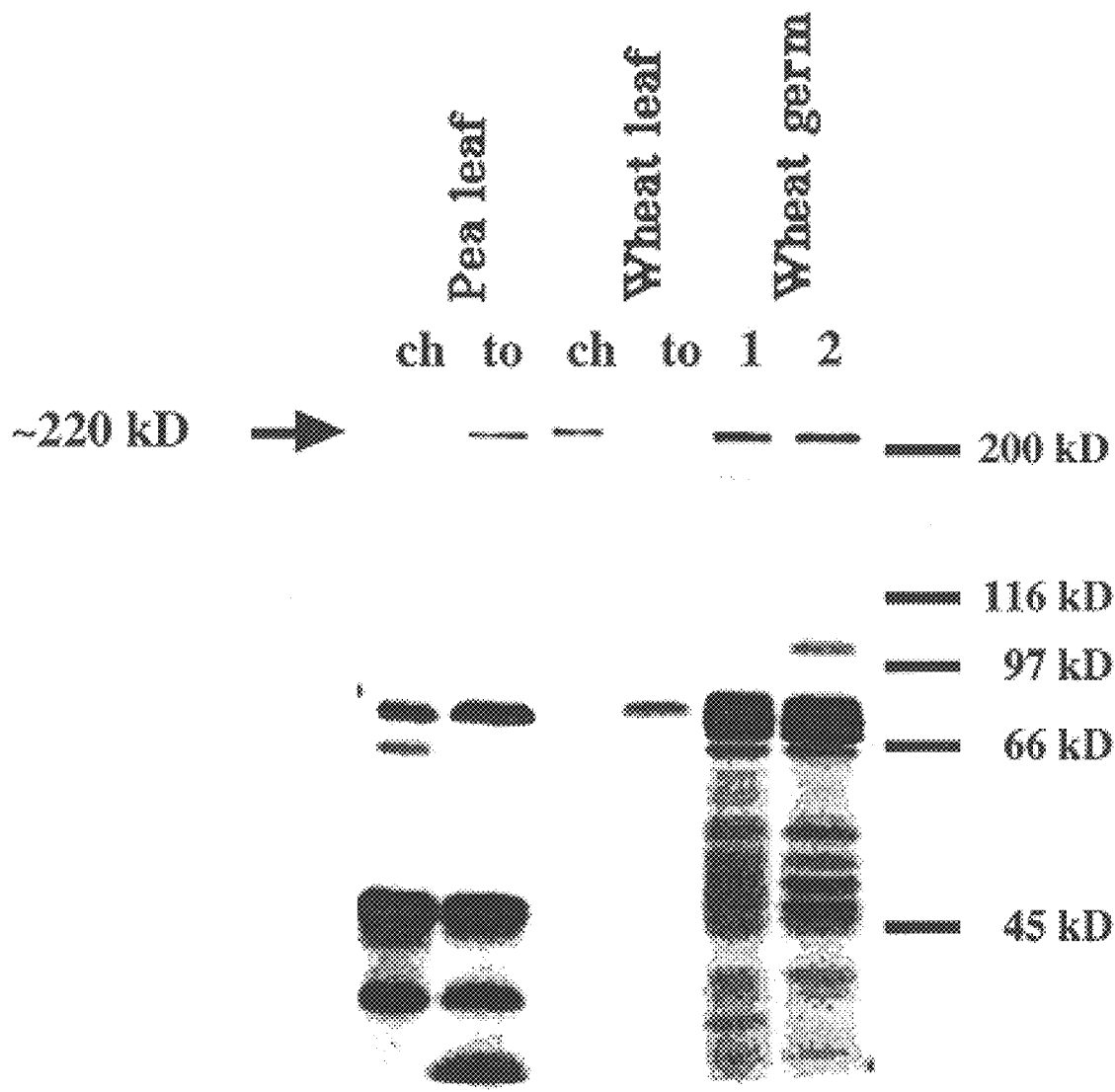
FIG. 4. Western analysis of biotinylated peptides in wheat and pea leaves (to, total leaf protein; ch, protein from gradient-purified intact chloroplasts), and in wheat germ (1, wheat germ extract purified through gel filtration on Sephadex G-100; 2, wheat germ extract purchased from Amersham). $^{14}$C-streptavidin was used to identify biotinylated polypeptides. Location of molecular weight markers is shown on the right.
Figure 5:
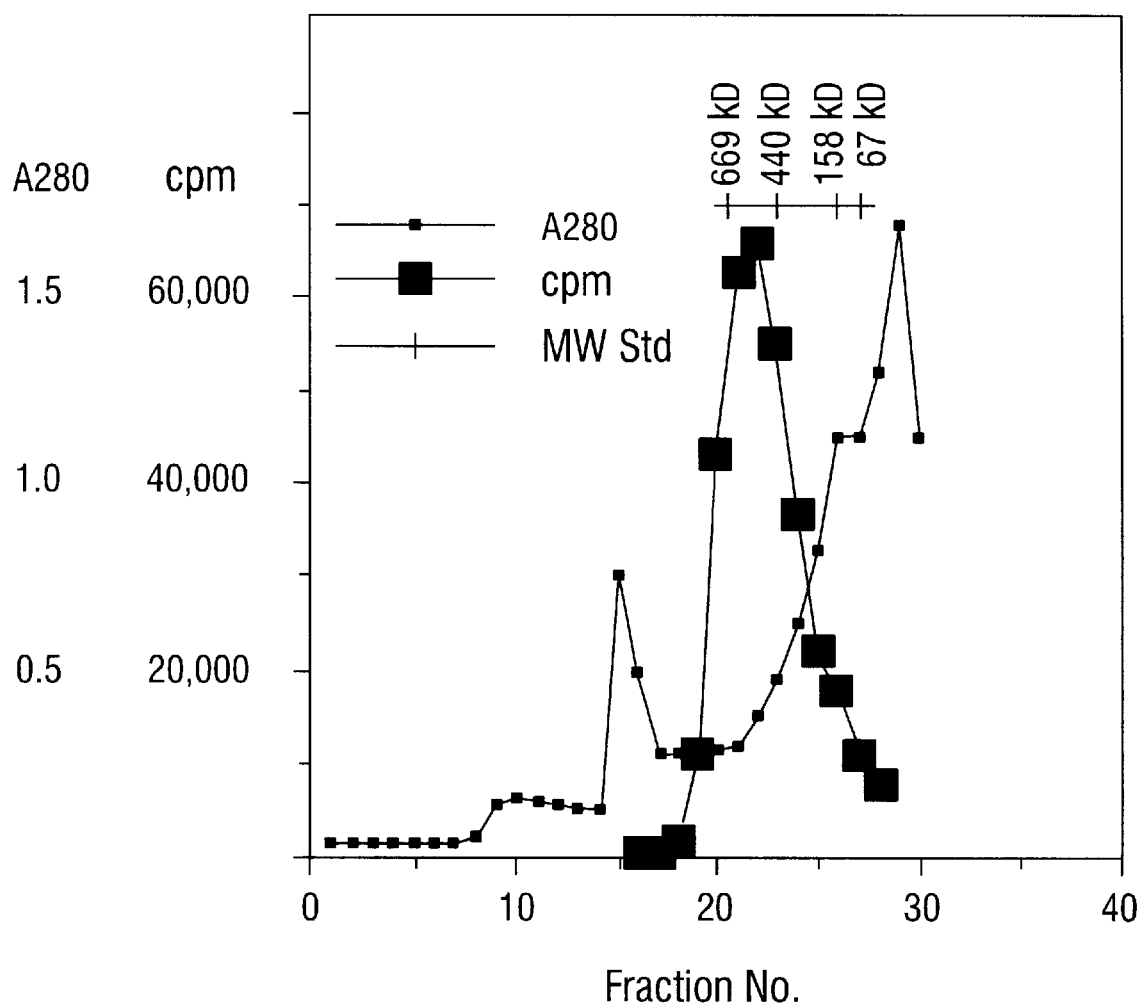
FIG. 5. Purification of ACC from wheat germ. A fraction partially purified by ammonium sulfate precipitation was run on G-100. The active fractions were pooled and run on DEAE-cellulose, and eluted with a step gradient of NaCl. The active fractions were pooled and separated by gel filtration on Superose as shown here. The peak of activity corresponds to a MW of 550,000.
Figure 6A:
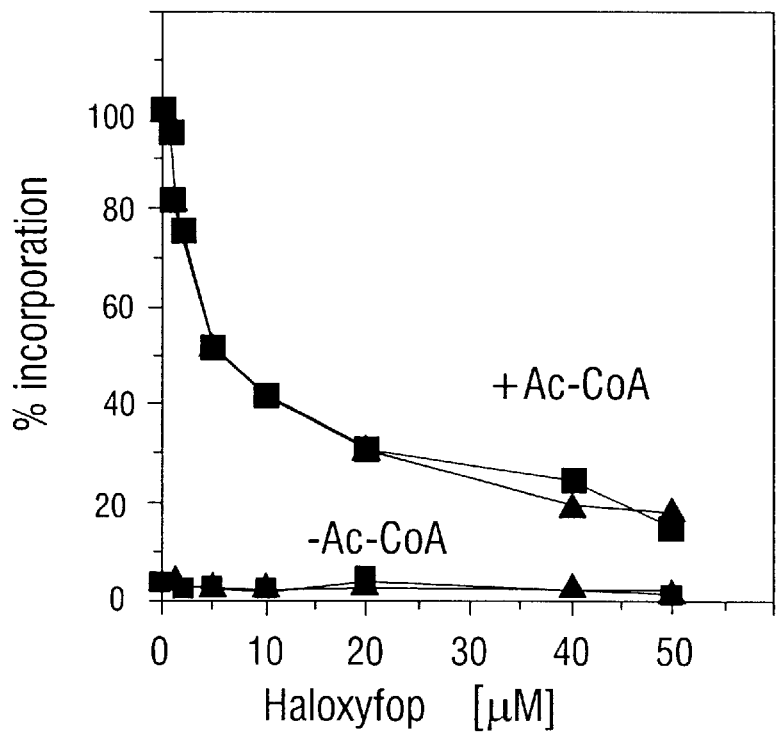
FIG. 6A. Effect of haloxyfop on wheat ACC activity. Incorporation of bicarbonate into malonate by wheat germ ACC (triangles, wheat germ extract partially purified throughout gel filtration on Sephadex G-100; squares, wheat germ extract purchased from Amersham) at different concentrations of haloxyfop.
Figure 6B:
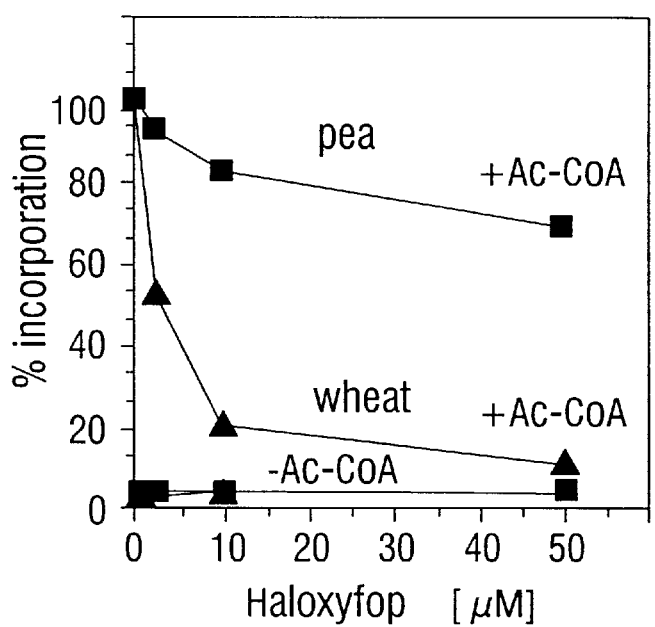
FIG. 6B. Effect of haloxyfop on wheat ACC activity. Incorporation of bicarbonate into malonate by ACC in protein from purified, intact wheat (triangles) and pea (squares) chloroplasts at different concentrations of haloxyfop.
Figure 6C:
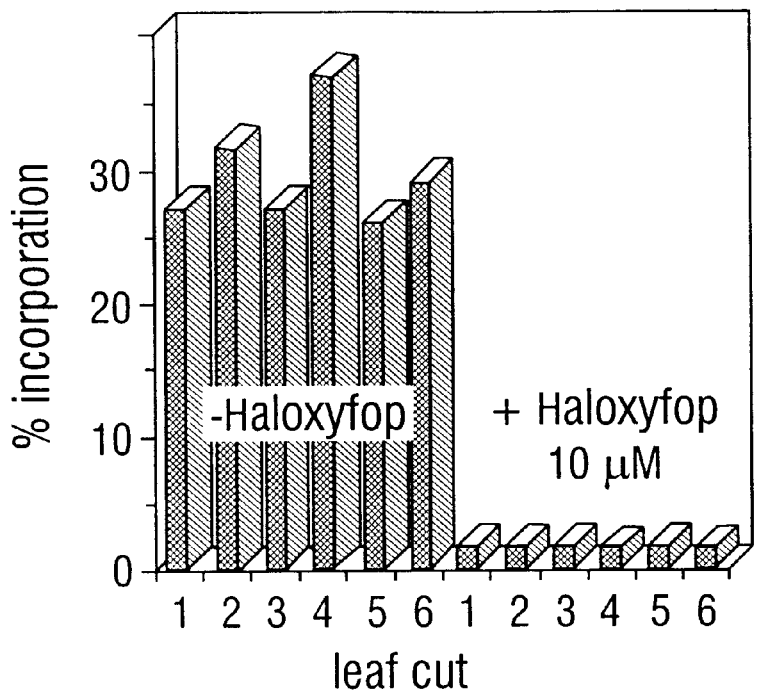
FIG. 6C. Effect of haloxyfop on wheat ACC activity. Incorporation of acetate into fatty acids in wheat leaves at 10 $\mu$M haloxyfop.
Figure 6D:
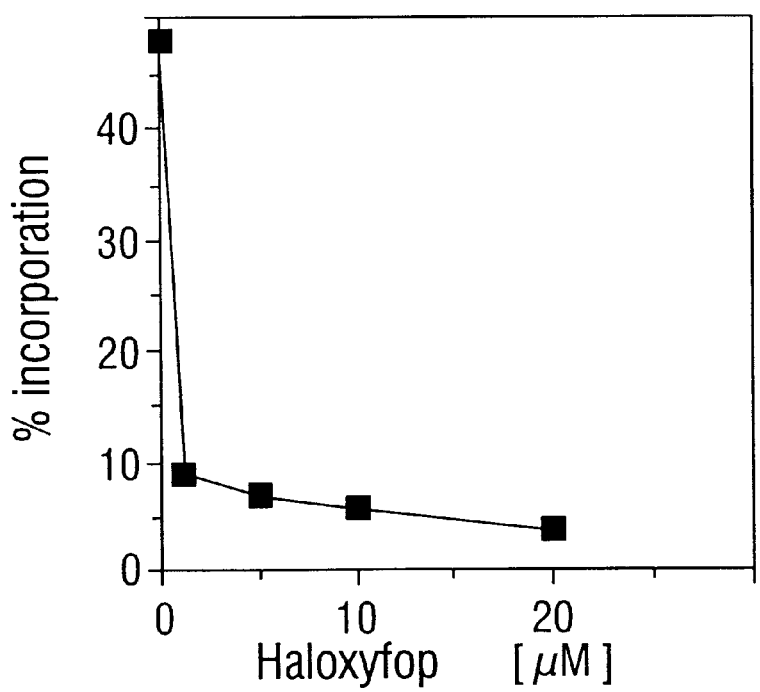
FIG. 6D. Effect of haloxyfop on wheat ACC activity. Incorporation of acetate into fatty acids in wheat leaves (average values of two independent measurements) at different concentrations of haloxyfop.

Biotin-containing (streptavidin-binding) proteins in extracts prepared from leaves of two-week old seedlings of wheat and pea, both total protein and protein from intact chloroplasts (prepared by centrifugation on Percoll gradients as described previously in Fernandez and Lamppa, 1991), and from wheat germ (Sephadex G-100 fraction prepared as described below) were analyzed by western blotting with $^{35}$S-Streptavidin (FIG. 4). Proteins were separated by SDS-PAGE using a 7.5% separating gel (Maniatis et al., 1982), and then were transferred onto a PVDF membrane (Immobilon-P®, Millipore) in 10 mM 3-(cyclohexylamino)-1-propanesulfonic acid buffer (pH 11), 10% methanol, at 4° C., 40 V, overnight. The blots were blocked with 3% BSA solution in 10 mM Tris-HCl pH 7.5 and 0.9% NaCl and then incubated for 3–16 h with $^{35}$S-Streptavidin (Amersham). The blots were washed at room temperature with 0.5% Nonidet-P40™ in 10 mM Tris-HCl pH 7.5 and 0.9% NaCl.

In wheat, the 220-kDa protein was present in both total and chloroplast protein. It was the major biotinylated polypeptide in the chloroplast protein (traces of smaller biotinylated polypeptides, most likely degradation products of the large one, could also be detected). ACC consisting of 220-kDa subunits is the most abundant biotin-dependent carboxylase present in wheat chloroplasts. In pea chloroplasts the biotinylated peptides are much smaller, probably due to greater degradation of the 220-kDa peptide, which could be detected only in trace amounts in some choroplast preparations. The amount of all biotinylated peptides, estimated from band intensities on western blots (amount of protein loaded was normalized for chlorophyll content). is much higher in pea than in wheat chloroplasts (FIG. 4).

Purification of wheat germ ACC was carried out at 4° C. or on ice. 200 g of wheat germ (Sigma) were homogenized (10 pulses, 10 s each) in a Waring blender with 300 ml of 100 mM Tris-HCl pH 7.5, 7 mM 2-mercaptoethanol. Two 0.3 ml aliquots of fresh 0.2M solution of phenylmethylsulfonyl fluoride (Sigma) in 100% ethanol were added immediately before and after homogenization. Soluble protein was recovered by centrifugation for 30 min at 12000 rpm. 1/33 volume of 10% poly(ethyleneimine) solution (pH 7.5) was added slowly and the mixture was stirred for 30 min (Egin-Buhler et al., 1980), followed by centrifugation for 30 min at 12000 RPM to remove the precipitate. ACC in the supernatant was precipitated by adding solid ammonium sulfate to 50% saturation.

The precipitate was collected by centrifugation for 30 min at 12000 rpm, dissolved in 200 ml of 100 mM KCl, 20 mM Tris-HCl pH 7.5, 20% glycerol, 7 mM 2-mercaptoethanol, mixed with 0.2 ml of phenylmethylsulfonyl fluoride solution (as above) and loaded on a 5 cm×50 cm Sephadex G-100 column equilibrated and eluted with the same buffer. Fractions containing ACC activity (assayed as described below using up to 20 µl aliquots of column fractions) were pooled and loaded immediately on a 2.5 cm×40 cm DEAE-cellulose column also equilibrated with the same buffer. The column was washed with 500, 250 and 250 ml of the same buffer containing 150, 200 and 250 mM KCl, respectively. Most of the ACC activity was eluted in the last wash. Protein present in this fraction was precipitated with ammonium sulfate (50% saturation), dissolved in a small volume of 100 mM KCl, 20 mM Tris-HCl pH 7.5, 5% glycerol, 7 mM 2-mercaptoethanol, and separated in several portions on two Superose columns connected in-line (Superose 6 and 12, Pharmacia). 1 ml fractions were collected at 0.4 ml/min flow rate. Molecular mass standards were thyroglobulin, 669-kDa; ferritin, 440-kDa; aldolase, 158-kDa; albumin, 67-kDa (Pharmacia). ACC-containing fractions were concentrated using Centricon-100 concentrators (Amicon) and the proteins were separated by SDS-PAGE as described above.

By gel filtration, active ACC had an apparent molecular mass of ~500-kDa and the individual polypeptides have a molecular mass of 220-kDa. The 220-kDa polypeptide was the major component of this preparation as revealed by Coomassie staining of proteins separated by SDS-PAGE. This preparation also contained several smaller biotin-containing peptides as revealed by western blotting with $^{35}$S-Streptavidin, most likely degradation products of the ca. 220-kDa peptide, which retained their ability to form the ~500-kDa complex and therefore co-purified with intact ACC. The ACC preparations were active only when they contained intact 220-kDa biotinylated polypeptide. It is not possible to estimate the recovery of the active ACC, due to continuous degradation of the 220-kDa peptide during purification and to increased recovery of ACC activity in more purified preparations, probably due to separation of the enzyme from inhibitors in the cruder extracts.

The 220-kDa wheat peptide isolated as a dimer according to the above protocol was finally purified by SDS-PAGE and transferred to Immobilon-P® for sequencing. The N-terminus of the peptide appeared to be blocked. A mixture of amino acids was detected only after the protein was cleaved chemically with CNBr. The 220-kDa protein was therefore purified on an SDS gel, cleaved with CNBr, and the resulting peptides were fractionated by gel electrophoresis basically as described (Jahnen-Dechent and Simpson, 1990), with the following modifications. A slice of gel containing about 20 µg of the 220-kDa polypeptide was dried under vacuum to about half of its original volume and then incubated overnight in 0.5 ml of 70% formic acid containing 25 mg of CNBr. The gel slice was dried again under vacuum to about half of its original volume and was equilibrated in 1 ml of 1M Tris-HCl (pH 8.0). The CNBr peptides were separated by inserting the gel piece directly into a well of a tricine gel (as described in Jahnen-Dechent and Simpson, 1990; but without a spacer gel). Gels used to separate peptides for sequencing were pre-run for 30 min with 0.1 mM thioglycolic acid in the cathode buffer. Peptides were transferred to Immobilon-P for sequencing by the Edman degradation method as described above.

Several bands of peptides, ranging in size from 4 to 16-kDa, with a well-resolved single band at about 14-kDa, were obtained. Attempts to sequence the smaller peptides failed, but the 14-kDa peptide yielded a clean results for residues 3–13.

EXAMPLE 6

EFFECTS OF THE HERBICIDE HALOXYFOP ON WHEAT ACC

The effect of haloxyfop, one of the aryloxyphenoxypropionate herbicides has been tested, on the activity of ACC from wheat germ and from wheat seedling leaves (FIG. 6A, FIG. 6B, FIG. 6C, FIG. 6D). For the in vitro assay of ACC activity, 1–8 µl aliquots of ACC preparations were incubated for 45 min at 37° C. with 20 µl of 100–200 mM KCl, 200 mM Tris-HCl pH 8.0, 10 mM MgCl$_2$, 2 mM ATP, 2 mM DTT, 2 mM $^{14}$C-NaCHCO$_3$, and where indicated 1 mM Ac-CoA, in a final volume of 40 µl. The reaction was stopped by adding 4 µl of concentrated HCl 30–40 µl aliquots of the reaction mixture were spotted on filter paper and dried, and acid-stable radioactivity was measured using scintillation cocktail. Haloxyfop was added as the Tris salt of the acid, generously supplied by J. Secor of Dow-Elanco.

For the in vivo assay of ACC activity, 2-week old seedlings of wheat (*Triticum aestivum* cv. Era) were cut about 1 cm below the first leaf and transferred to a 1.5 ml micro tube containing $^4$C-sodium acetate and haloxyfop (Tris salt) for 4–6 h. The leaves were then cut into small pieces and treated with 0.5 ml of 40% KOH for 1 h at 70° C., and then with 0.3 ml of H$_2$SO$_4$ and 20 µl of 30% TCA on ice. Fatty acids were extracted with three 0.5 ml aliquots of petroleum ether. The organic phase was washed with 1 ml of water. Incorporation of $^{14}$C-acetate into fatty acids is expressed as the percentage of the total radioactivity taken up by the seedlings, present in the organic phase.

As expected, the enzyme from wheat germ or from wheat chloroplasts was sensitive to the herbicide at very low levels. 50% inhibition occurs at about 5 and 2 µM haloxyfop, respectively. For comparison, the enzyme from pea chloroplasts is relatively resistant (50% inhibition occurs at >50 µM haloxyfop). Finally, the in vivo incorporation of $^{14}$C-acetate into fatty acids in freshly cut wheat seedling leaves is even more sensitive to the herbicide (50% inhibition occurs at <1 µM haloxyfop), which provides a convenient assay for both ACC and haloxyfop.

EXAMPLE 7

DEVELOPMENTAL ANALYSIS OF ACC GENES

Methods have been developed for analyzing the regulation of ACC gene expression on several levels. With the cDNA clones in hand, the first may be obtained by preparing total RNA from various tissues at different developmental stages e.g., from different segments of young wheat plants, then probing Northern blots to determine the steady-state level of ACC mRNA in each case. cDNA probes encoding conserved fragments of ACC may be used to measure total ACC mRNA level and gene specific probes to determine which gene is functioning in which tissue.

In parallel, the steady-state level of ACC protein (by western analysis using ACC-specific antibodies and/or using labeled streptavidin to detect biotinylated peptides) and its enzymatic activity may be measured to identify the most important stages of synthesis and reveal mechanisms involved in its regulation. One such study evaluates ACC expression in fast growing leaves (from seedlings at different age to mature plants), in the presence and in the absence of light.

EXAMPLE 8

ISOLATION OF HERBICIDE RESISTANT MUTANTS

Development of herbicide-resistant plants is an important aspect of the present invention. The availability of the wheat cDNA sequence facilitates such a process. By insertion of the complete ACC cDNA sequence into a suitable yeast vector in place of the yeast ACC coding region, it is possible to complement a FAS3 mutation in yeast using procedures well-known to those of skill in the art (see e.g., Haslacher et al., 1993). Analysis of the function of the wheat gene in yeast depends first on tetrad analysis, since the FAS3 mutation is lethal in homozygotes.

Observation of four viable spores from FAS3 tetrads containing the wheat ACC gene may confirm that the wheat gene functions in yeast, and extracts of the complemented FAS3 mutant may be prepared and assayed for ACC activity. These assays may indicate the range of herbicide sensitivity, and in these studies, haloxyfop acid and clethodim may be used as well as other related herbicide compounds.

Given that the enzyme expressed in yeast is herbicide-sensitive, the present invention may be used in the isolation of herbicide-resistant mutants. If spontaneous mutation to resistance is too infrequent, chemical mutagenesis with DES or EMS may be used to increase such frequency. Protocols involving chemical mutagenesis are well-known to those of skill in the art. Resistant mutants, i.e., strains capable of growth in the presence of herbicide, may be assayed for enzyme activity in vitro to verify that the mutation to resistance is within the ACC coding region.

Starting with one or more such verified mutants, several routes may lead to the identification of the mutated site that confers resistance. Using the available restriction map for the wild-type cDNA, chimeric molecules may be constructed containing half, quarter and eighth fragments, etc. from each mutant, then checked by transformation and tetrad analysis whether a particular chimera confers resistance or not.

Alternatively a series of fragments of the mutant DNA may be prepared, end-labeled, and annealed with the corresponding wild-type fragments in excess, so that all mutant fragments are in heterozygous molecules. Brief S1 or mung bean nuclease digestion cuts the heterozygous molecules at the position of the mismatched base pair. Electrophoresis and autoradiography is used to locate the position of the mismatch within a few tens of base pairs. Then oligo-primed sequencing of the mutant DNA is used to identify the mutation. Finally, the mutation may be inserted into the wild-type sequence by oligo-directed mutagenesis to confirm that it is sufficient to confer the resistant phenotype.

Having identified one or more mutations in this manner, the corresponding parts of several dicot ACC genes may be sequenced (using the physical maps and partial sequences as guides) to determine their structures in the corresponding region, in the expectation that they are now herbicide resistant.

EXAMPLE 9

ISOLATION AND SEQUENCE ANALYSIS OF CANOLA ACC cDNA

Wheat ACC cDNA probes were used to detect DNA encoding canola ACC. Southern analysis indicated that a wheat probe hybridizes quite strongly and cleanly with only a few restriction fragments that were later used to screen canola cDNA and genomic libraries (both libraries provided by Pioneer HiBred Co [Johnson City, Iowa]). About a dozen positive clones were isolated from each library.

Sequence analysis was performed for several of these genomic clones. Fragments containing both introns and exons were identified. One exon sequence encodes a polypeptide which is 75% identical to a fragment of wheat ACC. This is very high conservation especially for this fragment of the ACC sequence which is not very conserved in other eukaryotes. The 398-nucleotide DNA segment comprising a portion of the canola ACC gene is given in SEQ ID NO:19. The 132-amino acid translated sequence comprising a portion of the canola ACC polypeptide is given in SEQ ID NO:20.

One of the other genomic clones (6.5 kb in size) contains the 5' half of the canola gene, and additional screening of the genomic library may produce other clones which contain the promoter and other potential regulatory elements.

EXAMPLE 10

METHODS FOR OBTAINING ACC MUTANTS

In *E. coli,* only conditional mutations can be isolated in the acc genes. The reason is that although the bacteria can replace the fatty acids in triglycerides with exogenously provided ones, they also have an essential wall component called lipid A, whose β-hydroxy myristic acid can not be supplied externally.

One aspect of the present invention is the isolation of Anacystis mutants in which the BC gene is interrupted by an antibiotic resistance cassette. Such techniques are well-known to those of skill in the art (Golden et al., 1987). Briefly, the method involves replacing the cyanobacterial ACC with wheat ACC, so it is not absolutely necessary to be able to maintain the mutants without ACC. The wheat ACC clone may be introduced first and then the endogenous gene can be inactivated without loss of viability.

By replacing the endogenous herbicide resistant ACC in cyanobacteria with the wheat cDNA, resulting cells are sensitive to the herbicides haloxyfop and clethodim, whose target is known to be ACC. Subsequently, one may isolate mutants resistant to those herbicides. These methods are known to those of skill in the art (Golden et al., 1987).

The transformation system in Anacystis makes it possible to pinpoint a very small DNA fragment that is capable of conferring herbicide resistance. DNA sequencing of wild type and resistant mutants then reveals the basis of resistance.

Alternatively, gene replacement may be used to study wheat ACC activity and herbicide inhibition in yeast. Mutants may be selected which overcome the normal sensitivity to herbicides such as haloxyfop. This will yield a variant(s) of wheat ACC that are tolerant/resistant to the herbicides. The mutated gene (cDNA) present on the plasmid can be recovered and analyzed further to define the sites that confer herbicide resistance. As for the herbicide selection, there is a possibility that the herbicide may be inactivated before it can inhibit ACCase activity or that it may not be transported into yeast. There are general schemes for treatment of yeast with permeabilizing antibiotics at sublethal concentrations, which are known to those of skill in the art. Such treatments allow otherwise impermeable drugs to be used effectively. For these studies haloxyfop acid and clethodim may be used.

Characterization of the site(s) conferring herbicide resistance generally involves assaying extracts of the complemented ACC1 mutant for ACCase activity. Both spontaneous mutation and chemical mutagenesis with DES or EMS, may be used to obtain resistant mutants, i.e., strains capable of growth in the presence of herbicide. These may be assayed for enzyme activity in vitro to verify that the mutation to resistance is within the ACCase coding region. Starting with one or more such verified mutants, the mutated site that confers resistance may be analyzed. Using the available restriction map for the wild-type cDNA, chimeric molecules may be constructed which containing half, quarter and eighth fragments, etc., from each mutant, and then checked by transformation and tetrad analysis to determine whether a particular chimera confers resistance or not.

An alternative method involves preparing a series of fragments of the mutant DNA, end-labeling, and annealing with the corresponding wild-type fragments in excess, so that all mutant fragments are in heterozygous molecules. Brief S1 or mung bean nuclease digestion cuts the heterozygous molecules at the position of the mismatch within a few tens of base pairs. Then oligo-primed sequencing of the mutant DNA is used to identify the mutation. Finally, the mutation can be inserted into the wild-type sequence by oligo-directed mutagenesis to confirm that it is sufficient to confer the resistant phenotype. Having identified one or more mutations in this manner, the corresponding parts of several dicot ACCase genes to determine their structures in the corresponding region, in the expectation that they would be "resistant".

Another method for the selection of wheat ACCase mutants tolerant or resistant to different herbicides involves the phage display technique. Briefly, in the phage display technique, foreign peptides can be expressed as fusions to a capsid protein of filamentous phage. Generally short (6 to 18 amino acids), variable amino acid sequences are displayed on the surface of a bacteriophage virion (a population of phage clones makes an epitope library). However, filamentous bacteriophages have also been used to construct libraries of larger proteins such as the human growth hormone, alkaline phosphatase (Scott, 1992) or a 50-kDa antibody Fab domain (Kang et al., 1991). In those cases, the foreign inserts were spliced into the major coat protein pVIII of the M13 phagemid. A complementary helper phage supplying wild-type pVIII has to be cotransferred together with the phagemid. Such "fusion phages" retained full infectivity and the fused proteins were recognized by monoclonal antibodies. These results demonstrate that foreign domains displayed by phage can retain at least partial native folding and activity.

Phage libraries displaying wild-type fragments of the wheat ACCase of 250 to 300 amino acids in size may be constructed without "panning" for phage purification. The mechanism of purifying phages by panning involves reaction with biotinylated monoclonal antibodies, then the complexes are diluted, immobilized on streptavidin-coated plates, washed extensively and eluted. Generally, a few rounds of panning are recommended.

Instead, fragments bearing the ATP-binding site may be obtained by using Blue Sepharose CL-6B affinity chromatography, which was shown to bind plant ACCs (Betty et al., 1992; Egin-Buhler et al., 1980). Herbicides bound to Sepharose serve for capturing those phages which display amino acid fragments involved in herbicide binding. Such herbicide affinity resins may also be employed. After identifying peptide fragments that bind herbicides, ATP or acetyl-CoA, the phages bearing those peptides may be subjected to random mutagenesis, again using phage display and binding to the appropriate support to select the interesting variants. Sequence analysis then is used to identify the critical residues of the protein required for binding.

EXAMPLE 11

PREPARATION OF ACC-SPECIFIC ANTIBODIES

Another aspect of the present invention is the preparation of antibodies reactive against plant ACC for use in immunoprecipitation, affinity chromatography, and immunoelectron microscopy. The antisera may be prepared in rabbits, using methods that are well-known to those of skill in the art (see e.g., Schneider and Haselkorn, 1988).

Briefly, the procedure encompasses the following aspects. Gel-purified protein is electroeluted, dialyzed, mixed with complete Freund's adjuvant and injected in the footpad at several locations. Subsequent boosters are given with incomplete adjuvant and finally with protein alone. Antibodies are partially purified by precipitating lipoproteins from the serum with 0.25% sodium dextran sulfate and 80 mM $CaCl_2$. Immunoglobulins are precipitated with 50% saturating ammonium sulfate, suspended in phosphate-buffered saline at 50 mg/ml and stored frozen. The antisera prepared as described may be used in Western blots of protein extracts from wheat, pea, soybean, canola and sunflower chloroplasts as well as total protein.

EXAMPLE 12

PROTEIN FUSIONS AND TRANSGENIC PLANTS AND MODIFICATIONS OF ACC AFFECTING TRANSPORT

Analysis of promoter and control elements with respect to their structure as well as tissue specific expression, timing etc., is performed using promoter fusions (e.g. with the GUS gene) and appropriate in situ assays. Constructs may be made which are useful in the preparation of transgenic plants.

For identifying transport of ACC, model substrates containing different length N-terminal fragments of ACC may be prepared by their expression (and labeling) in E. coli or by in vitro transcription with T7 RNA polymerase and translation (and labeling) in a reticulocyte lysate. Some of the model substrates will include the functional biotinylation site (located ~800 amino acids from the N-terminus of the mature protein; the minimum biotinylation substrate will be defined in parallel) or native ACC epitope(s) for which antibodies will be generated as described above. Adding an antibody tag at the C-terminus will also be very helpful. These substrates will be purified by affinity chromatography (with antibodies or streptavidin) and used for in vitro assays.

For modification of ACC protein transport, model substrates consisting of a transit peptide (or any other chloroplast targeting signals) to facilitate import into chloroplasts, fused to different ACC domains that are potential targets for modification, may be used. Modified polypeptides from cytoplasmic and/or chloroplast fractions will be analyzed for modification. For example, protein phosphorylation (with $^{32}$P) can be followed by immunoprecipitation or by PAGE. Antibodies to individual domains of ACC may then be employed. The same experimental set-up may be employed to study the possible regulation of plant ACC by phosphorylation (e.g., Witters and Kemp, 1992). Biotinylation may be followed by Western analysis using $^{35}$S-streptavidin for detection or by PAGE when radioactive biotin is used as a substrate.

EXAMPLE 3

EXPRESSION SYSTEMS FOR THE PREPARATION OF LARGE-SCALE QUANTITIES OF ACC POLYPEPTIDES

The entire plant ACC cDNA and its fragments, and BC, BCCP and the CT gene clones from cyanobacteria may be used to prepare large amounts of the corresponding proteins in *E. coli*. This is most readily accomplished using the T7 expression system. As designed by Studier, this expression system consists of an *E. coli* strain carrying the gene for T7 lysozyme and for T7 RNA polymerase, the latter controlled by a lac inducible promoter. The expression vector with which this strain can be transformed contains a promoter recognized by T7 RNA polymerase, followed by a multiple cloning site into which the desired gene can be inserted (Ashton et al., 1994).

Prior to induction, the strain grows well, because the few molecules of RNA polymerase made by basal transcription from the lac promoter are complexed with T7 lysozyme. When the inducer IPTG is added, the polymerase is made in excess and the plasmid-borne gene of interest is transcribed abundantly from the late T7 promoter. This system easily makes 20% of the cell protein the product of the desired gene. A benefit of this system is that the desired protein is often sequestered in inclusion bodies that are impossible to dissolve after the cells are lysed. This is an advantage in the present invention, because biological activity of these polypeptides is not required for purposes of raising antisera. Moreover, other expression systems are also available (Ausubel et al., 1989).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below and all references cited herein are incorporated herein by reference to the extent that they supplement, explain, provide a background for, or teach methodology, techniques, and/or compositions employed herein.

Abdullah et al., *Biotechnology*, 4:1087, 1986.

Al-feel et al., "Cloning of the yeast FAS3 gene and primary structure of yeast acetyl-CoA carboxylase," *Proc. Natl. Acad. Sci. USA*, 89:4534–4538, 1992.

Alban et al., "Purification and characterization of 3-methylcrotonyl-coenzyme A carboxylase from higher plant mitochondria," *Plant. Physiol.*, 102:957–965, 1993.

Alix, "A rapid procedure for cloning genes from 1 libraries by complementation of *E. coli* defective mutants: application to the fabE region of the *E. coli* chromosome," DNA, 8:779–789, 1989.

Ashton et al., *Plant Mol. Biol.*, 24:35–49, 1994.

Ausubel, F. M. et al., "Current Protocols in Molecular Biology," John Wiley & Sons, New York, 1989.

Benbrook et al., In: *Proceedings Bio Expo 1986*, Butterworth, Stoneham, Mass., pp. 27–54, 1986.

Berry-Lowe et al., "Chloroplast protein Transport," *Cell Culture and Somatic Cell Genetics of Plants*, Vol. 7A, pp 257–302, Academic Press, New York, 1991.

Best and Knauf, "Organization and nucleotide sequence of the genes encoding the biotin carboxyl carrier protein and biotin carboxylase protein of *Pseudomonas aeruginosa* acetyl coenzyme A carboxylase," *J. Bacteriol.*, 175:6881–6889, 1993.

Betty et al., "Purification and characterization of acetyl-CoA carboxylase from developing pea embryos," *J. Plant. Physiol.*, 140:513–520, 1992.

Bowness et al., *Eur. J. Immunol.*, 23:1417, 1993.

Brichard et al., *J. Exp. Med.*, 178:489, 1993.

Brock et al., "Biology of Microorganisms" 7th Edition, Prentice Hall, Inc., Englewood Cliffs, N.J., 1994.

Browner et al., "Sequence analysis, biogenesis and mitochondrial import of the alpha-subunit of rat liver propionyl-Co-A carboxylase," *J. Biol. Chem.*, 264:12680–12685, 1989.

Bytebier et al., *Proc. Natl. Acad. Sci. USA*, 84:5345, 1987.

Callis et al., *Genes and Development*, 1:1183, 1987.

Campbell, "Monoclonal Antibody Technology, Laboratory Techniques in Biochemistry and Molecular Biology," Vol. 13, Burden and Von Knippenberg, Eds. pp. 75–83, Elsevier, Amsterdam, 1984.

Capecchi, M. R., "High efficiency transformation by direct microinjection of DNA into cultured mammalian cells," *Cell* 22(2):479–488, 1980.

Cashmore et al., *Gen. Eng. of Plants*, Plenum Press, New York, 29–38, 1983.

Cavener and Ray, *Nucleic Acids Res.*, 19:3185–3192, 1991.

Charng et al., "Molecular cloning and expression of the gene encoding ADP-glucose pyrophosphorylase from the cyanobacterium Anabaena sp. strain PCC 7120," *Plant Mol. Biol.*, 20:37–47, 1992.

Chau et al., *Science*, 244:174–181, 1989.

Chen et al., "Purification and characterization of 3-methylcrotonyl-CoA carboxylase from somatic embryos of *Dacus carota*," *Arch. Biochem. Biophys.*, 305:103–109, 1993.

Chirala, "Coordinated regulation and inositol-mediated and fatty acid-mediated repression of fatty acid synthase genes in Saccharomyces cerevisiae," *Proc Natl Acad Sci USA*, 89:10232–10236, 1992.

Chirgwin et al., *Biochemistry*, 18:5294–5304, 1979.

Clapp, D. W., "Somatic gene therapy into hematopoietic cells. Current status and future implications," *Clin. Perinatol.* 20(1):155–168, 1993.

Clark and Lamppa, "Processing of the precursor for the light-harvesting chlorophyll-binding proteins of photosystem II and photosystem I during import in an organelle-free assay," *Plant Physiol.*, 98:595–601, 1992.

Cristou et al., *Plant Physiol,* 87:671–674, 1988.

Curiel, D. T., Agarwal, S., Wagner, E., and Cotten, M., "Adenovirus enhancement of transferrin-polylysine-mediated gene delivery," *Proc. Natl. Acad. Sci. USA* 88(19):8850–8854, 1991.

Curiel, D. T., Wagner, E., and Cotten, M., Birnstiel, M. L., Agarwal, S., Li, C. M., Loechel, S., and Hu, P. C. "high-efficiency gene transfer mediated by adenovirus coupled to DNA-polylysine complexes," *Hum. Gen. Ther.* 3(2):147–154, 1992.

Dean and Leech, *Plant Physiol.,* 69:904–910, 1982.

Dhir et al., *Plant Cell Reports,* 10:97, 1991.

Dibrino et al., *J. Immunol.,* 152:620, 1994.

Egin-Buhler et al., "Comparison of acetyl-CoA carboxylase from parsley cell culture and from wheat germ," *Arch. Biochem. Biophys.,* 203:90–100, 1980.

Egin-Buhler et al., "Improved purification and further characterization of ACC from culture cells of parsley," *Eur. J. Biochem.,* 133:335–339, 1983.

Egli et al., "Characterization of maize acetyl-coenzyme A carboxylase," *Plant. Physiol.,* 101:499–506, 1993.

Eglitis, M. A., and Anderson, W. F., "Retroviral vectors for introduction of genes into mammalian cells," *Biotechniques* 6(7):608–614, 1988.

Eglitis, M. A., Kantoff, P. W., Kohn, D. B., Karson, E., Moen, R. C., Lothrop, C. D., Blaese, R. M., and Anderson, W. F., "Retroviral-mediated gene transfer into hemopoietic cells," *Adv. Exp. Med. Biol.* 241:19–27, 1988.

Elborough et al., "Studies on wheat acetyl CoA carboxylase and the cloning of a partial cDNA," *Plant Mol. Biol.,* 24:21–34, 1994.

Feel et al., "Cloning of the yeast FAS3 gene and primary structure of yeast acetyl-CoA carboxylase," *Proc Natl Acad, Sci USA,* 89:4534–4538, 1992.

Fernandez and Lamppa, "Acyl carrier protein import into chloroplasts," *J. Biol. Chem.,* 266:7220–7226, 1991.

Fraley et al., *Biotechnology,* 3:629, 1985.

Fraley et al., *Proc. Natl. Acad. Sci. USA,* 80:4803, 1983.

From et al., *Nature,* 319:791, 1986.

Fromm, M., Taylor, L. P., and Walbot, V., "Expression of genes transferred into monocot and dicot plant cells by electroporation," *Proc. Natl. Acad. Sci. USA* 82(17):5824–5828, 1985.

Fujimura et al., *Plant Tissue Culture Letters,* 2:74, 1985.

Fynan, E. F., Webster, E. G., Fuller, D. H., Haynes, J. R., Santoro, J. C., and Robinson, H. L., "DNA vaccines: protective immunizations by parenteral, mucosal, and gene gun inoculations," *Proc. Natl. Acad. Sci. USA* 90(24):11478–11482, 1993.

Gefter et al., *Somatic Cell Genet.* 3:231–236, 1977.

Gendler et al., *J. Biol. Chem.,* 263:12820, 1988.

Goding, "Monoclonal Antibodies: Principles and Practice," pp. 60–74. 2nd Edition, Academic Press, Orlando, Fla., 1986.

Golden et al., "Genetic engineering of the cyanobacterial chromosome," *Methods Enzymol.,* 153:215–231, 1987.

Goodal et al., "Analysis of pre-mRNA in transfected plant protoplasts," *Methods Enzymol.,* 181:148–161, 1990.

Gordon-Kamm et al., *The Plant Cell,* 2:603–618, 1990.

Gornicki and Haselkorn, "Wheat acetyl-CoA carboxylase," *Plant Mol. Biol.,* 22:547–552, 1993.

Gornicki et al., "Genes for two subunits of acetyl-CoA carboxylase of Anabaena sp. strain PCC 7120: biotin carboxylase and biotin carboxyl carrier protein," *J. Bacteriol.,* 175:5268–5272, 1993.

Gornicki et al., *J. Bacteriol.,* 175:5268–5272, 1993.

Graham, F. L., and van der Eb, A. J., "Transformation of rat cells by DNA of human adenovirus 5," Virology 54(2):536–539, 1973.

Grimm et al., *J. Exp. Med.,* 155:1823, 1982.

Guan and Dixon, "Eukaryotic proteins expressed in *Escherichia coli*: an improved thrombin cleavage and purification procedure of fusion proteins with glutathione S-transferase", *Anal. Biochem.* 192:262–267, 1991.

Ha et al., "Critical phosphorylation sites for acetyl-CoA carboxylase activity," *J. Biol. Chem.,* 269:22162–22168, 1994.

Ha et al., *Eur. J. Biochem.,* 219:297–306, 1994.

Hardie et al., "The AMP-activated protein kinase: a multi-substrate regulator of lipid metabolism," *Trends in Biochem. Sci.,* 14:20–23, 1989.

Harlow, E. and Lane, D. "Antibodies: A Laboratory Manual," Cold Spring Harbor Laboratory, Cold Spring Harbor, N.Y., 1988.

Harwood, "Fatty acid metabolism," *Ann. Rev. Physiol. Plant Mol. Biol.,* 39:101–138, 1988.

Haslacher et al., "Acetyl-CoA carboxylase from yeast is an essential enzyme and is regulated by factors that control phospholipid metabolism," *J. Biol. Chem.,* 268:10946–10952, 1993.

Haymerle et al., "Efficient construction of cDNA libraries in plasmid expression vectors using an adaptor strategy," *Nucl. Acids Res.,* 14:8615–8629, 1986.

Hess, *Intern Rev. Cytol.,* 107:367, 1987.

Hilber, U. W., Bodmer, M., Smith, F. D., and Koller, W., "Biolistic transformation of conidia of *Botryotinia fuckeliana*," *Curr. Genet.* 25(2):124–127, 1994.

Hill et al., *Nature,* 360:434, 1992.

Hogquist et al., "Peptide variants reveal how antibodies recognize major histocompatibility complex class I," *Eur. J. Immunol.,* 23:3028–3036, 1993.

Holt et al., "Mechanisms and agronomic aspects of herbicide resistance," *Annu. Rev. Plant. Physiol. Plant Mol. Biol.,* 44:203–229, 1993.

Horsch et al., *Science,* 227:1229–1231, 1985.

Hu et al., *J. Exp. Med.,* 177:1681, 1993.

Jacobson et al., *J. Virol.,* 63:1756, 1989.

Jahnen-Dechent and Simpson, "A method for preparing proteins and peptides for microsequencing," *Plant Mol. Biol. Rep.,* 8:92–103, 1990.

Jameson and Wolf, *Compu. Appl. Biosci.,* 4(1):181–6, 1988.

Jerome et al., *Cancer Res.,* 51:2908, 1991.

Jerome et al., *J. Immunol.,* 151:1654, 1993.

Johnston, S. A., and Tang, D. C., "Gene gun transfection of animal cells and genetic immunization," *Methods Cell. Biol.* 43(A):353–365, 1994.

Jorgensen et al., *Mol. Gen. Genet.,* 207:471, 1987.

Kaiser and Kezdy, "Amphiphilic secondary structure: Design of peptide hormones," *Science,* 223:249–255, 1984.

Kang et al., "Linkage of recognition and replication functions by assembling combinatorial antibody Fab libraries along phage surfaces," *Proc. Natl. Acad. Sci. USA,* 88:4363–4366, 1991.

Karow et al., "The lethal phenotype caused by null mutations in the *Escherichia coli* htrB gene is suppressed by mutations in the accBC operon, encoding two subunits of acetyl coenzyme A carboxylase," *J. Bacteriol.,* 174:7407–7418, 1992.

Keller et al., *EMBO J.,* 8:1309–14, 1989.

Klee et al., *In: Plant DNA Infectious Agents,* T. Hohn and J. Schell, eds., Springer-Verlag, New York pp. 179–203, 1985.

Klein et al., *Nature,* 327:70, 1987.
Klein et al., *Plant Physiol.,* 91:440–444, 1989.
Klein et al., *Proc. Natl. Acad. Sci. USA,* 85:8502–8505, 1988.
Knowles, "The mechanism of biotin-dependent enzymes," *Annu. Rev. Biochem.,* 58:195–221, 1989.
Kohler and Milstein, *Eur. J. Immunol.* 6:511–519, 1976.
Kohler and Milstein, *Nature* 256:495–497, 1975.
Kondo et al., "Acetyl-CoA carboxylase from *E. coli:* gene organization and nucleotide sequence of the biotin carboxylase subunit," *Proc Natl Acad Sci USA,* 88:9730–9733, 1991.
Kos and Müllbacher, *Eur. J. Immunol.,* 22:3183, 1992.
Krzyzek, R. A., "Genetic transformation of maize cells by electroporation of cells pretreated with pectin degrading enzymes," U.S. Pat. No. 5,384,253, Jan 1, 1995.
Kyte and Doolittle, *J. Mol. Biol.,* 157:105–132, 1982.
Lamppa et al., "Structure and developmental regulation of a wheat gene encoding the major chlorophyll a/b-binding polypeptide," *Mol. Cell Biol.,* 5:1370–1378, 1985.
Langridge et al., *Proc. Natl. Acad. Sci. USA,* 86:3219–3223, 1989.
Letessier et al., *Cancer Res.,* 51:3891, 1991.
Li and Cronan, "Growth rate regulation of *Escherichia coli* acetyl coenzyme A carboxylase, which catalyzes the first committed step of lipid biosynthesis," *J. Bacteriol.,* 175:332–340, 1993.
Li and Cronan, "Putative zinc finger protein encoded by a conserved chloroplast gene is very likely a subunit of a biotin-dependent carboxylase," *Plant Mol. Biol.,* 20:759–761, 1992.
Li and Cronan, "The gene encoding the biotin carboxylase subunit of *Escherichia coli* acetyl-CoA carboxylase," *J. Biol. Chem.,* 267:855, 1992.
Lichtenthaler, "Mode of action of herbicides affecting acetyl-CoA carboxylase and fatty acid biosynthesis," *Z. Naturforsch.,* 45c:521–528, 1990.
Lim et al., "Sequence and domain structure of yeast pyruvate carboxylase," *J. Biol. Chem.,* 263:11493–11497, 1988.
Lindstrom et al., *Developmental Genetics,* 11:160, 1990.
Liu and Roizman, "The Herpes Simplex Virus 1 gene encoding a protease also contains within its coding domain the gene encoding the more abundant substrate," *J. Virol.,* 65:5149–5156, 1991.
Lopez-Casillas et al., "Structure of the coding sequence and primary amino acid sequence of rat Acetyl-coenzyme A carboxylase," *Proc. Natl. Acad. Sci. USA,* 85:5784–5788, 1988.
Lorz et al., *Mol. Gen. Genet.,* 199:178, 1985.
Lu, L., Xiao, M., Clapp, D. W., Li, Z. H., and Broxmeyer, H. E., "High efficiency retroviral mediated gene transduction into single isolated immature and replatable CD34(3+) hematopoietic stem/progenitor cells from human umbilical cord blood," *J. Exp. Med.* 178(6): 2089–2096, 1993.
Lundquist, R. C.,Walters, D. A., and Kirihara, J. A., "Fertile transgenic *Zea mays* plants—comprising recombinant DNA encoding seed storage protein," WO/9110725 Jul. 25, 1991.
Luo et al., *Plant Mol. Biol. Reporter,* 6:165, 1988.
Luo et al., "Structural features of acetyl-CoA carboxylase gene: mechanism for the generation of mRNAs with 5'-end heterogeneity," *Proc. Natl. Acad. Sci. USA,* 86:4042–4046, 1989.
Maddock et al., *Third International Congress of Plant Molecular Biology,* Abstract 372, 1991.
Maniatis et al., "Molecular Cloning: A Laboratory Manual," Cold Spring Harbor Laboratory, Cold Spring Harbor, N.Y., 1982.
Maloy, S. R., "Experimental Techniques in Bacterial Genetics" Jones and Bartlett Publishers, Boston, Mass., 1990.
Maloy et al., "Microbial Genetics" 2nd Edition. Jones and Barlett Publishers, Boston, Mass., 1994.
Marcotte et al., *Nature,* 335:454, 1988.
Marincola et al., *Cancer Res.,* 83:932, 1991.
Marshall et al., "Allelic mutations in acetyl-coenzyme A carboxylase confer herbicide tolerance in maize," *Theor. Appl. Genet.,* 83:435–442, 1992.
McCabe et al., *Biotechnology,* 6:923, 1988.
*Methods for Plant Molecular Biology,* A. Weissbach and H. Weissbach, eds., Academic Press, Inc., San Diego, Calif., 1988.
Mullis, K., U.S. Pat. No. 4,683,202, Jul. 28, 1987.
Mullis, K. et al., U.S. Pat. No. 4,683,195, Jul. 28, 1987.
Muramatsu and Mizuno, "Nucleotide sequence of the fabE gene and flanking regions containing a bent DNA sequence of Escherichia coli," *Nucleic Acids Res.,* 17:3982, 1989.
Murata and Nishida, In: P. K. Stumpf (ed.), *The Biochemistry of Plants,* Academic Press, Inc., New York, 9:315–347, 1987.
Neuhaus et al., *Theor. Appl. Genet.,* 75:30, 1987.
Odell et al., *Nature,* 313:810, 1985.
Ohno, *Proc. Natl. Acad. Sci. USA,* 88:3065, 1991.
Omirulleh et al., *Plant Molecular Biology,* 21:415–428, 1993.
Pecker et al., "A single polypeptide catalyzing the conversion of phytoene to z-carotene is transcriptionally regulated during tomato fruit ripening," *Proc Natl Acad Sci USA,* 89:4962–4666, 1992.
Pena et al., *Nature,* 325:274, 1987.
Poszkowski et al., *EMBO J.,* 3:2719, 1989.
Potrykus et al., *Mol. Gen. Genet.,* 199:183, 1985.
Poulsen et al., *Mol. Gen. Genet.,* 205:193–200, 1986.
Ratner and Clark, *J. Immunol.,* 150:4303, 1993.
Rawn, J. D. *"Biochemistry"* Harper & Row Publishers, New York, 1983.
Rippka et al., "Genetic assignments, strain histories and properties of pure cultures of cyanobacteria," *J. Gen. Microbiol.,* 170:4136–4140, 1979.
Roessler and Ohlrogge, "Cloning and characterization of the gene that encodes acetylcoenzyme A carboxylase in the alga *Cyclotella cryptica,"* *J. Biol. Chem.,* 268:19254–19259, 1993.
Rogers et al., *In: Methods For Plant Molecular Biology,* A. Weissbach and H. Weissbach, eds., Academic Press Inc., San Diego, Calif. 1988.
Rogers et al., *Meth. in Enzymol.,* 153:253–277, 1987.
Sambrook et al., "Molecular Cloning: A Laboratory Manual," Cold Spring Harbor Laboratory, Cold Spring Harbor, N.Y., 1989.
Samols et al., "Evolutionary conservation among biotin enzymes," *J. Biol. Chem.,* 263:6461–6464, 1988.
Sasaki et al., "Chloroplast-encoded protein as a subunit of acetyl-CoA carboxylase in pea plant," *J. Biol. Chem.,* 268:25118–25123, 1993.
Schneider and Haselkorn, "RNA polymerase subunit homology among cyanobacteria, other eubacteria and archaebacteria," *J. Bacteriol.* 170:4136–4140, 1988.
Scoble et al., "Mass spectrometric strategies for structural characterization of proteins," *In: A practical guide to protein and peptide purification for microsequencing,* P. Matsudaira, ed., pp 125–153, Academic Press, New York, 1993.

Scott, "Discovering peptide ligands using epitope libraries," *TIBS*, 17:241–245, 1992.

Segal, I. H., "Biochemical Calculations" 2nd Edition. John Wiley & Sons, New York, 1976.

Sheen, "Metabolic repression of transcription in higher plants," *Plant Cell*, 21027–1038, 1990.

Shenoy et al., "The importance of methionine residues for the catalysis of the biotin enzyme, transcarboxylase," *J. Biol. Chem.*, 267:18407–18412, 1992.

Sherman et al.; *J. Exp. Med.*, 175:1221, 1992.

Simpson, *Science*, 233:34, 1986.

Slabas and Fawcett, "The biochemistry and molecular biology of plant lipid biosynthesis," *Plant Mol. Biol.*, 19:169–191, 1992.

Slabas and Hellyer, "Rapid purification of a high molecular weight subunit polypeptide form of rape seed acetyl-CoA carboxylase," *Plant Sci.* 39:177–182, 1985.

Somers et al., "Expression of the Acc1 gene-encoded acetyl-coenzyme A carboxylase in developing maize (*Zea mays* L.) kernels," *Plant Physiol.*, 101:1097–1101, 1993.

Somerville and Browse, "Plant lipids: metabolism, mutants, and membranes," *Science*, 252:80–87, 1991.

Spielmann et al., *Mol. Gen. Genet.*, 205:34, 1986.

Steinman, *Annu. Rev. Immunol.*, 9:271, 1991.

Suhrbier et al., *J. Immunol.*, 150:2169, 1993.

Takai et al., "Primary structure of chicken liver acetyl-coenzyme A carboxylase deduced from cDNA sequence," *J. Biol. Chem.*, 263:2651–2657, 1988.

Toh et al., "Molecular evolution of biotin-dependent carboxylases," *Eur. J. Biochem.*, 215:687–696, 1993.

Tomes et al., *Plant Mol. Biol.*, 14:261–268, 1990.

Toriyama et al., *Theor Appl. Genet.*, 73:16, 1986.

Uchimiya et al., *Mol. Gen. Genet.*, 204:204, 1986.

Van Tunen et al., *EMBO J.*, 7:1257, 1988.

Vasil, *Biotechnology*, 6:397, 1988.

Vasil et al., "Herbicide-resistant fertile transgenic wheat plants obtained by microprojectile bombardment of regenerable embryogenic callus," *Biotechnology*, 10:667–674, 1992.

Vodkin et al., *Cell*, 34:1023, 1983.

Vogel et al., *J. Cell Biochem.*, supplement 131D:312, 1989.

Wagner, E., Zatloukal, K., Cotten, M., Kirlappos, H., Mechtler, K., Curiel, D. T., and Birnstiel, M. L., "Coupling of adenovirus to transferrin-polylysine/DNA complexes greatly enhances receptor-mediated gene delivery and expression of transfected genes," *Proc. Natl. Acad. Sci. USA* 89(13):6099–6103, 1992.

Weissbach and Weissbach, *Methods for Plant Molecular Biology*, (eds.), Academic Press, Inc., San Diego, Calif., 1988.

Wenzler et al., *Plant Mol. Biol.*, 12:41–50, 1989.

Winter et al., *J. Immunol.*, 146:3508, 1991.

Witters and Kemp, "Insulin activation of acetyl-CoA carboxylase by inhibition of the 5'-AMP-activated protein kinase," *J. Biol. Chem.*, 267:2864–2867, 1992.

Wolf et al., *Compu. Appl. Biosci.*, 4(1):187–91 1988.

Wolfel et al., *Int. J. Cancer*, 54:636, 1993.

Wong, T. E., and Neumann, E., "Electric field mediated gene transfer," *Biochim. Biophys. Res. Commun.* 107(2): 584–587, 1982.

Wood, R. A., "Metabolism," In Manual of Methods for General Bacteriology, (Gerhardt, Murray, Costilow, Nester, Wood, Krieg, and Phillips, Eds.) American Society for Microbiology, Washington, D.C., 1981.

Wurtele and Nikolau, "Differential accumulation of biotin enzymes during carrot somatic embryogenesis," *Plant. Physiol.*, 99:1699–1703, 1992.

Wurtele and Nikolau, "Plants contain multiple biotin enzymes: discovery of 3-methylcrotonyl-CoA carboxylase, propionyl-CoA carboxylase and pyruvate carboxylase in the plant kingdom," *Arch. Biochem. Biophys.*, 278:179–186, 1990.

Yamada et al., *Plant Cell Rep.*, 4:85, 1986.

Yang et al., *Proc. Natl. Acad. Sci. USA*, 87:4144–48, 1990.

Young and Davis, "Efficient Isolation of Genes by Using Antibody Probes," *Proc. Natl. Acad. Sci. USA*, 80:1194–1198, 1983.

Zatloukal, L., Wagner, E., Cotten, M., Phillips, S., Plank, C., Steinlein, P., Curiel, D. T., and Birnstiel, M. L., "Transferrinfection: a highly efficient way to express gene constructs in eukaryotic cells," *Ann. N.Y. Acad. Sci.* 660:136–153, 1992.

Zhou et al., *Methods in Enzymology*, 101:433, 1983.

---

What is claimed is:

1. An isolated nucleic acid segment comprising a gene that encodes a polypeptide comprising the sequence of SEQ ID NO:2. SEQ ID NO:4, SEQ ID NO:6, SEQ ID NO:8, SEQ ID NO:10 SEQ ID NO:12. or SEQ ID NO:20.

2. The nucleic acid segment of claim 1, wherein said gene comprises the nucleic acid sequence of SEQ ID NO:1, SEQ ID NO:3, SEQ ID NO:5, SEQ ID NO:7, SEQ ID NO:9, SEQ ID NO:11, or SEQ ID NO:19.

3. The nucleic acid segment of claim 2, wherein said gene comprises the nucleotide sequence of SEQ ID NO:9, SEQ ID NO:11 or SEQ ID NO:19.

4. The nucleic acid segment of claim 2, wherein said gene comprises the nucleotide sequence of SEQ ID NO:1, SEQ ID NO:3, SEQ ID NO:5, or SEQ ID NO:7.

5. The nucleic acid segment of claim 1, operably linked to at least a first promoter said promoter expressing said gene.

6. The nucleic acid segment of claim 1, wherein said segment is up to about 10,000 basepairs in length.

7. The nucleic acid segment of claim 6, wherein said segment is up to about 5,000 basepairs in length.

8. The nucleic acid segment of claim 7, wherein said segment is up to about 4,000 basepairs in length.

9. The nucleic acid segment of claim 8, wherein said segment is up to about 3,000 basepairs in length.

10. The nucleic acid segment of claim 9, wherein said segment is up to about 2,000 basepairs in length.

11. The nucleic acid segment of claim 10, wherein said segment is up to about 1,000 basepairs in length.

12. The nucleic acid segment of claim 1, further defined as RNA or DNA.

13. The nucleic acid segment of claim 1, wherein said gene is operably linked to a plant-expressible promoter.

14. A host cell comprising the nucleic acid segment of claim 1.

15. The host cell of claim 14, wherein said cell is a prokaryotic cell.

16. The host cell of claim 15, wherein said cell is a bacterial or cyanobacterial host cell.

17. The host cell of claim 16, wherein said bacterial cell is an E. coli or salmonella cell.

18. The host cell of claim 16, wherein said cyanobacterial cell is a Synechococcus spp. or Anabaena spp. cell.

19. The host cell of claim 14, wherein said cell is an eukaryotic cell.

20. The host cell of claim 19, wherein said cell is a yeast cell or a plant cell.

21. The host cell of claim 20, wherein said cell is a monocotyledonous or dicotyledonous plant cell.

22. The host cell of claim 21, wherein said dicotyledonous plant cell is selected from the group consisting of soybean, rape, sunflower, tobacco, Aradidopsis, petunia, canola, pea, bean, tomato, potato, lettuce, spinach, carrot, alfalfa, and cotton.

23. The host cell of claim 21, wherein said monocotyledonous plant cell is selected from the group consisting of wheat, rice, maize, barley, rye, oats, and timothy grass.

24. The host cell of claim 14, comprising at least a first vector that comprises said nucleic acid segment.

25. The host cell of claim 14, wherein said host cell expresses said nucleic acid segment to produce the encoded polypeptide.

26. The host cell of claim 25, wherein said polypeptide comprises the amino acid sequence of SEQ ID NO:2; SEQ ID NO:4; SEQ ID NO: 6; SEQ ID NO: 8; SEQ ID NO: 10; SEQ ID NO: 12; or SEQ ID NO: 20.

27. A polynucleotide comprising a sequence region that encodes a polypeptide comprising at least 19 contiguous amino acids from SEQ ID NO:2, SEQ ID NO:4, SEQ ID NO:6, SEQ ID NO:8, SEQ ID NO:10, SEQ ID NO:12, or SEQ ID NO:20.

28. The polynucleotide of claim 27, comprising a sequence region that encodes a polypeptide comprising at least 21 contiguous amino acids from SEQ ID NO:2, SEQ ID NO:4, SEQ ID NO:6, SEQ ID NO:8, SEQ ID NO:10, SEQ ID NO:12, or SEQ ID NO:20.

29. The polynucleotide of claim 28, comprising a sequence region that encodes a polypeptide comprising at least 23 contiguous amino acids from SEQ ID NO:2, SEQ ID NO:4, SEQ ID NO:6, SEQ ID NO:8, SEQ ID NO:10, SEQ ID NO:12, SEQ ID NO:20.

30. The polynucleotide of claim 29, comprising a sequence region that encodes a polypeptide comprising at least 25 contiguous amino acids from SEQ ID NO:2, SEQ ID NO:4, SEQ ID NO:6, SEQ ID NO:8, SEQ ID NO:10, SEQ ID NO:12, or SEQ ID NO:20.

31. The polynucleotide of claim 27, further defined as DNA or RNA.

32. A vector comprising the polynucleotide of claim 27.

33. A nucleic acid segment comprising an isolated gene encoding a contiguous amino acid sequence from a canola acetyl-CoA carboxylase or a subunit of cyanobacterial acetyl-CoA carboxylase functionally linked to a contiguous amino acid sequence from a monocotyledonous acetyl-CoA carboxylase.

34. An isolated nucleic acid segment, comprising a sequence region of at least 25 contiguous nucleotides from SEQ ID NO: 1; or at least 19 contiguous nucleotides from SEQ ID NO:3; or at least 21 contiguous nucleotides from SEQ ID NO:5; or at least 17 contiguous nucleotides from SEQ ID NO:7; or at least least 21 contiguous nucleotides from SEQ ID NO:9; or at least 20 contiguous nucleotides from SEQ ID NO:11; or at least 18 contiguous nucleotides from SEQ ID NO:19, or a complement thereof.

35. An isolated nucleic acid segment, comprising a sequence region of at least 25 contiguous nucleotides from SEQ ID NO:1; or at least 19 contiguous nucleotides from SEQ ID NO:3, or a complement thereof.

36. An isolated nucleic acid segment, comprising a sequence region of at least 21 contiguous nucleotides from SEQ ID NO:5 or SEQ ID NO:9, or a complement thereof.

37. An isolated nucleic acid segment, comprising a sequence region of at least 17 contiguous nucleotides from SEQ ID NO:7, or a complement thereof.

38. An isolated nucleic acid segment, comprising a sequence region of at least 20 contiguous nucleotides from SEQ ID NO:11; or at least 18 contiguous nucleotides from SEQ ID NO:19, or a complement thereof.

39. An isolated nucleic acid segment, comprising a gene that encodes a polypeptide comprising at least 14 contiguous residues from SEQ ID NO:2, SEQ ID NO:4, SEQ ID NO:12 or SEQ ID NO:20.

40. An isolated nucleic acid segment, comprising a gene that encodes a polypeptide comprising at least 16 contiguous residues from SEQ ID NO:6 or SEQ ID NO:10.

41. An isolated nucleic acid segment, comprising a gene that encodes a polypeptide comprising at least 19 contiguous residues from SEQ ID NO:8.

42. A method of preparing a polypeptide, comprising the steps of:
  (a) obtaining a vector that comprises the nucleic acid segment of claim 1, wherein said gene is positioned under the control of a promoter;
  (b) introducing said vector into a host cell;
  (c) culturing the host cell under conditions effective to allow expression of the encoded polypeptide; and
  (d) collecting said expressed polypeptide.

43. A monocotyledonous plant having incorporated into its genome at least a first transgene that encodes a polypeptide comprising the amino acid sequence of SEQ ID NO:2, SEQ ID NO:4, SEQ ID NO:6, SEQ ID NO:8, SEQ ID NO:12, or SEQ ID NO:20.

44. The monocotyledonous plant of claim 43, selected from the group consisting of wheat, rice, maize, barley, rye, oats, and timothy grass.

45. A seed or progeny from the plant of claim 43, wherein said seed or progeny has said transgene incorporated into its genome.

46. A monocotyledonous plant having incorporated into its genome at least a first transgene comprising the nucleic acid sequence of SEQ ID NO:1, SEQ ID NO:3, SEQ ID NO:5, SEQ ID NO:7, SEQ ID NO:11 or SEQ ID NO:19.

47. A dicotyledonous plant having incorporated into its genome at least a first transgene encoding a polypeptide that comprises the amino acid sequence of SEQ ID NO:2, SEQ ID NO:4, SEQ ID NO:6, SEQ ID NO:8, SEQ ID NO:10, or SEQ ID NO:12.

48. The dicotyledonous plant of claim 47, wherein said transgene comprises the nucleic acid sequence of SEQ ID NO:1, SEQ ID NO:3, SEQ ID NO:5, SEQ ID NO:7, SEQ ID NO:9, or SEQ ID NO:11.

49. A seed or progeny from the plant of claim 46, wherein said seed or progeny has said transgene incorporated into its genome.

50. A process for increasing the acetyl CoA carboxylase activity in a monocotyledonous cell comprising introducing into said cell a vector comprising a gene encoding a dicotyledonous acetyl CoA carboxylase polypeptide comprising a sequence region of at least 14 contiguous amino acids from SEQ ID NO:20, and culturing said transformed cell under conditions effective to express said gene and to produce said acetyl-CoA carboxylase polypeptide.

51. The process according to claim 50, wherein said acetyl-CoA carboxylase polypeptide comprises the amino acid sequence of SEQ ID NO:20.

52. The process according to claim 51, wherein said plant acetyl-CoA carboxylase polypeptide is encoded by a nucleic acid segment comprising the nucleic acid sequence of SEQ ID NO:19.

* * * * *

UNITED STATES PATENT AND TRADEMARK OFFICE
CERTIFICATE OF CORRECTION

PATENT NO. : 5,910,626

DATED : June 8, 1999

INVENTOR(S) : Haselkorn et al.

It is certified that error appears in the above-identified patent and that said Letters Patent is hereby corrected as shown below:

Claim 49, col. 113, ln. 3, delete "46" and insert --47-- therefor.

Signed and Sealed this

Ninth Day of November, 1999

Attest:

Q. TODD DICKINSON

Attesting Officer

Acting Commissioner of Patents and Trademarks

SEQUENCE LISTING (1) GENERAL INFORMATION:

(iii) NUMBER OF SEQUENCES: 31

(2) INFORMATION FOR SEQ ID NO:1:

(i) SEQUENCE CHARACTERISTICS:
      (A) LENGTH: 1458 base pairs
      (B) TYPE: nucleic acid
      (C) STRANDEDNESS: single
      (D) TOPOLOGY: linear (xi) SEQUENCE DESCRIPTION: SEQ ID NO:1:

```
AAGCTTCATG ATTTCTAGTA ACGATTTTCG ACCTGGTGTA TCCATTGTCT TAGATGGGTC      60

TGTATGGCGA GTGATAGATT TCCTTCACGT TAAGCCAGGT AAGGGTTCTG CCTTTGTACG     120

GACAACTCTG AAGAACGTCC AAAGCGGCAA AGTTTTAGAA AAAACCTTCC GGGCTGGGGA     180

AACTGTTCCA CAAGCTACTT TAGAAAAAAT TACAATGCAG CATACCTATA AAGAGGGCGA     240

TGAGTTCGTC TTTATGGATA TGGAAAGCTA TGAAGAAGGA CGACTCAGCG CCGCACAAAT     300
```

```
TGGCGATCGC GTCAAATACC TCAAGGAAGG TATGGAAGTG AACGTCATTC GTTGGGGTGA      360

GCAAGTGCTA GAGGTGGAAC TGGCTAATTC TGTAGTCTTG GAAGTTATAC AAACTGATCC      420

AGGTGTCAAG GGTGACACGG CTACAGGTGG CACGAAACCA GCAATTGTCG AAACTGGTGC      480

AACTGTGATG GTTCCTTTGT TTATTTCTCA AGGAGAGCGA ATTAAAATTG ATACCCGTGA      540

TGATAAATAC TTAGGCAGGG AATAGGTTTT ATCTCATCCG AGAACAAATC CCGATTTCAA      600

TCCCTATTTC AGGGATTAAA TCCCTGCCAC ACTTAGGCCA ATTCAAAATT CAAAATTCAA      660

AAAACTGGAT TCCCTTAAGG TTTCTGAGTC TCAATGGTAG ATGGATTTTG GAGAGTTGGT      720

ATGAAAAATT CTTTATTTAC GGACTGGTCG AGGTAATAAA AACTGTGCCA TTGGACTTTA      780

ATGAAATCCG TCAACTGCTG ACAACTATTG CACAAACAGA TATCGCGGAA GTAACGCTCA      840

AAAGTGATGA TTTTGAACTA ACGGTGCGTA AAGCTGTTGG TGTGAATAAT AGTGTTGTGC      900

CGGTTGTGAC AGCACCCTTG AGTGGTGTGG TAGGTTCGGG ATTGCCATCG GCTATACCGA      960

TTGTAGCCCA TGCTGCCCCA TCTCCATCTC CAGAGCCGGG AACAAGCCGT GCTGCTGATC     1020

ATGCTGTCAC GAGTTCTGGC TCACAGCCAG GAGCAAAAAT CATTGACCAA AAATTAGCAG     1080

AAGTGGCTTC CCCAATGGTG GGAACATTTT ACCGCGCTCC TGCACCAGGT GAAGCGGTAT     1140

TTGTGGAAGT CGGCGATCGC ATCCGTCAAG GTCAAACCGT CTGCATCATC GAAGCAATGA     1200

AGCTGATGAA TGAAATTGAG GCTGATGTTT CTGGGCAAGT GATCGAAATT CTCGTCCAAA     1260

ACGGCGAACC TGTAGAATAT AATCAACCTT TGATGAGAAT TAAACCAGAT TAAGTATTAA     1320

TGTATATAGG TGAGTCATTA CTAACTCAAG TTGCTAGTTA TGTTTGGTAA TTGGTAACTG     1380

GTGATTGCTA ATTGGTAATT GAGAAAAATT TTACTCATTA CCCATCACCC ATTACCAGTT     1440

CTTAAATTGA TAGCTAGC                                                   1458
```

(2) INFORMATION FOR SEQ ID NO:2:

(i) SEQUENCE CHARACTERISTICS:
        (A) LENGTH: 182 amino acids
        (B) TYPE: amino acid
        (C) STRANDEDNESS:
        (D) TOPOLOGY: linear (xi) SEQUENCE DESCRIPTION: SEQ ID NO:2:

```
Met Pro Leu Asp Phe Asn Glu Ile Arg Gln Leu Leu Thr Thr Ile Ala
 1               5                  10                  15

Gln Thr Asp Ile Ala Glu Val Thr Leu Lys Ser Asp Asp Phe Glu Leu
            20                  25                  30

Thr Val Arg Lys Ala Val Gly Val Asn Asn Ser Val Val Pro Val Val
        35                  40                  45

Thr Ala Pro Leu Ser Gly Val Gly Ser Gly Leu Pro Ser Ala Ile
    50                  55                  60

Pro Ile Val Ala His Ala Ala Pro Ser Pro Ser Pro Glu Pro Gly Thr
65                  70                  75                  80

Ser Arg Ala Ala Asp His Ala Val Thr Ser Ser Gly Ser Gln Pro Gly
                85                  90                  95

Ala Lys Ile Ile Asp Gln Lys Leu Ala Glu Val Ala Ser Pro Met Val
            100                 105                 110

Gly Thr Phe Tyr Arg Ala Pro Ala Pro Gly Glu Ala Val Phe Val Glu
        115                 120                 125

Val Gly Asp Arg Ile Arg Gln Gly Gln Thr Val Cys Ile Ile Glu Ala
    130                 135                 140

Met Lys Leu Met Asn Glu Ile Glu Ala Asp Val Ser Gly Gln Val Ile
145                 150                 155                 160
```

```
       Glu Ile Leu Val Gln Asn Gly Glu Pro Val Glu Tyr Asn Gln Pro Leu
                       165                 170                 175

Met Arg Ile Lys Pro Asp
                       180

(2) INFORMATION FOR SEQ ID NO:3:

(i) SEQUENCE CHARACTERISTICS:
         (A) LENGTH: 477 base pairs
         (B) TYPE: nucleic acid
         (C) STRANDEDNESS: single
         (D) TOPOLOGY: linear (xi) SEQUENCE DESCRIPTION: SEQ ID NO:3:

GTGCAACTGA ACTTCAGCCA ACTGCAAGAG CTGCTGACCG TGCTGAGTGA CTCAGACATC         60

GCTGAGTTTG ACCTCAAAGG TACGGATTTT GAGTTGCACG TGAAGCGCGG CTCGACCGGC        120

GACCCGATCG TCATTGCGGC TCCCACCACG CCCGTTGCTG TCGCTCCCGT GCCCGCTCCC        180

TTACCCGCTC CAACCCCTGC GGCAGCACCG CCTGCTGGAC CTCTGGGTGG CGAGAAGTTC        240

CTTGAGATTA CGGCGCCGAT GGTGGGCACC TTCTATCGCG CTCCAGCACC GGAAGAACCG        300

CCCTTCGTCA ATGTTGGCGA TCGCATTCAG GTGGGACAGA CCGTCTGCAT CCTCGAAGCG        360

ATGAAGCTGA TGAACGAGTT GGAGTCGGAG GTGACGGGGG AAGTCGTCGA GATTCTGGTC        420

CAGAACGGCG AACCGGTGGA GTTTAATCAG CCCCTGTTCC GGTTGCGGCC TCTCTGA           477

(2) INFORMATION FOR SEQ ID NO:4:

(i) SEQUENCE CHARACTERISTICS:
         (A) LENGTH: 158 amino acids
         (B) TYPE: amino acid
         (C) STRANDEDNESS:
         (D) TOPOLOGY: linear (xi) SEQUENCE DESCRIPTION: SEQ ID NO:4:

Met Gln Leu Asn Phe Ser Gln Leu Gln Glu Leu Leu Thr Val Leu Ser
       1               5                   10                  15

Asp Ser Asp Ile Ala Glu Phe Asp Leu Lys Gly Thr Asp Phe Glu Leu
                       20                  25                  30

His Val Lys Arg Gly Ser Thr Gly Asp Pro Ile Val Ile Ala Ala Pro
                       35                  40                  45

Thr Thr Pro Val Ala Val Ala Pro Val Pro Ala Pro Leu Pro Ala Pro
                       50                  55                  60

Thr Pro Ala Ala Ala Pro Pro Ala Gly Pro Leu Gly Gly Glu Lys Phe
       65                  70                  75                  80

Leu Glu Ile Thr Ala Pro Met Val Gly Thr Phe Tyr Arg Ala Pro Ala
                       85                  90                  95

Pro Glu Glu Pro Pro Phe Val Asn Val Gly Asp Arg Ile Gln Val Gly
                       100                 105                 110

Gln Thr Val Cys Ile Leu Glu Ala Met Lys Leu Met Asn Glu Leu Glu
                       115                 120                 125

Ser Glu Val Thr Gly Glu Val Val Glu Ile Leu Val Gln Asn Gly Glu
                       130                 135                 140

Pro Val Glu Phe Asn Gln Pro Leu Phe Arg Leu Arg Pro Leu
       145                 150                 155

(2) INFORMATION FOR SEQ ID NO:5:

(i) SEQUENCE CHARACTERISTICS:
         (A) LENGTH: 3065 base pairs
```

(B) TYPE: nucleic acid
(C) STRANDEDNESS: single
(D) TOPOLOGY: linear (xi) SEQUENCE DESCRIPTION: SEQ ID NO:5:

```
AAGCTTTTAT ATTTTGCCAT TTCTAGAACT TAGCTGCATC GGCCCCAAGT ATTTTGTCAA      60
ATATGGCGAA AAGACTTCAT AAATCAAGGT TAAAGGTTGA CCGTGATGCC AAAACAGGTA     120
ATGGCGACCC CAGAAAGGCC CATCCACGCC AAAACCTAAT TGCAAGGCCT CTGAATTTCC     180
GTAATAAATA CCCCGCACAT CCCGATACAA CTCCGTGCGA AGACGAGCTA GACTTGCCCA     240
AATTGGTAAT GAACGGTTTT GCAAATACTC GTCTACATGG CTGGCTTCCC ACCATGAGGT     300
TGCATAGGCG AGTCGTTGGC CAGAGCGTGT ACGTAGCCAT ACCTGTCGCC GCAGTCTTGG     360
CGCTGGAACA GATTGGATTA AATCCGGCGC ACTATCTAAA TCCAAACCAA TCAATGACAT     420
ATCAATGACA TCGACTTCTG TTGGCTCACC AGTAAGTAAT TCTAAATGCC TTGTGGGTGA     480
GCCATCACCT AAGAGTAGTA GTTGCCACGC TGGAGCCAGC TGAGTGTGAG GCAAACTATG     540
TTTAATTACT TCTTCCCCAC CTTGCCAAAT AGGAGTGAGG CGATGCCATC CGGCTGGCAG     600
TGTTGAGTTG TTGCTTGGAG TAAAAGTGGC AGTCAATGTT CTTTACAAAA GTTCACCTAT     660
TTATATCAAA GCATAAAAAA TTAATTAGTT GTCAGTTGTC ATTGGTTATT CTTCTTTGCT     720
CCCCCTGCCC CCTACTTCCC TCCTCTGCCC AATAATTAGA AAGGTCAGGA GTCAAAAACT     780
TATCACTTTT GACCACTGAC CTTTCACAAT TGACTATAGT CACTAAAAAA TGCGGATGGC     840
GAGACTCGAA CTCGCAAGGC AAAGCCACAC GCACCTCAAG CGTGCGCGTA TACCAATTCC     900
GCCACATCCG CACGGGTTGT ACAAGAAGAT ATACTAGCAC AAAAAAATTG CATAAAACAA     960
GGTAAAACTA TATTTGCCAA ACTTTATGGA AAATTTATCT TGCTAAATAT ACAAATTTCC    1020
CGAAGAGGAT ACGAGACTAA CAGAAATGTA GTATCGCCAC AAGTGATATT AAAGGGGGTA    1080
TGGGGGTTTT CTTCCCTTAC ACCCTTAAAC CCTCACACCC CACCTCCATG AAAAATCTTG    1140
TTGGTAAGTC CGTTTCCTGC AATTTATTTA AAGATGAGCC TGGGGTATCT CCTGTCATAA    1200
TTTGAGATGA AGCGATGCCT AAGGCGGCTA CGCTACGCGC TAAAAGCAAC TTGGATGGGA    1260
GACAATTTCT ATCTGCTGGT ACTGATACTG ATATCGAAAA CTAGAAAATG AAGTTTGACA    1320
AAATATTAAT TGCCAATCGG GGAGAAATAG CGCTGCGCAT TCTCCGCGCC TGTGAGGAAA    1380
TGGGGATTGC GACGATCGCA GTTCATTCGA CTGTTGACCG GAATGCTCTT CATGTCCAAC    1440
TTGCTGACGA AGCGGTTTGT ATTGGCGAAC CTGCTAGCGC TAAAAGTTAT TTGAATATTC    1500
CCAATATTAT TGCTGCGGCT TTAACGCGCA ATGCCAGTGC TATTCATCCT GGGTATGGCT    1560
TTTTATCTGA AAATGCCAAA TTTGCGGAAA TCTGTGCTGA CCATCACATT GCATTCATTG    1620
GCCCCACCCC AGAAGCTATC CGCCTCATGG GGGACAAATC CACTGCCAAG GAAACCATGC    1680
AAAAAGCTGG TGTACCGACA GTACCGGGTA GTGAAGGTTT GGTAGAGACA GAGCAAGAAG    1740
GATTAGAACT GGCGAAAGAT ATTGGCTACC CAGTGATGAT CAAAGCCACG GCTGGTGGTG    1800
GCGGCCGGGG TATGCGACTG GTGCGATCGC CAGATGAATT TGTCAAACTG TTCTTAGCCG    1860
CCCAAGGTGA AGCTGGTGCA GCCTTTGGTA ATGCTGGCGT TTATATAGAA AAATTTATTG    1920
AACGTCCGCG CCACATTGAA TTTCAAATTT TGGCTGATAA TTACGGCAAT GTGATTCACT    1980
TGGGTGAGAG GGATTGCTCA ATTCAGCGTC GTAACCAAAA GTTACTAGAA GAAGCCCCCA    2040
GCCCAGCCTT GGACTCAGAC CTAAGGGAAA AAATGGGACA AGCGGCGGTG AAAGCGGCTC    2100
AGTTTATCAA TTACGCCGGG GCAGGTACTA TCGAGTTTTT GCTAGATAGA TCCGGTCAGT    2160
TTTACTTTAT GGAGATGAAC ACCCGGATTC AAGTAGAACA TCCCGTAACT GAGATGGTTA    2220
```

```
CTGGAGTGGA TTTATTGGTT GAGCAAATCA GAATTGCCCA AGGGGAAAGA CTTAGACTAA    2280

CTCAAGACCA AGTAGTTTTA CGCGGTCATG CGATCGAATG TCGCATCAAT GCCGAAGACC    2340

CAGACCACGA TTTCCGCCCA GCACCCGGAC GCATTAGCGG TTATCTTCCC CCTGGCGGCC    2400

CTGGCGTGCG GATTGACTCC CACGTTTACA CGGATTACCA AATTCCGCCC TACTACGATT    2460

CCTTAATTGG TAAATTGATC GTTTGGGGCC CTGATCGCGC TACTGCTATT AACCGCATGA    2520

AACGCGCCCT CAGGGAATGC GCCATCACTG GATTACCTAC AACCATTGGG TTTCATCAAA    2580

GAATTATGGA AAATCCCCAA TTTTTACAAG GTAATGTGTC TACTAGTTTT GTGCAGGAGA    2640

TGAATAAATA GGGTAATGGG TAATGGGTAA TGGGTAATAG AGTTTCAATC ACCAATTACC    2700

AATTCCCTAA CTCATCCGTG CCAACATCGT CAGTAATCCT TGCTGGCCTA GAAGAACTTC    2760

TCGCAACAGG CTAAAAATAC CAACACACAC AATGGGGGTG ATATCAACAC CACCTATTGG    2820

TGGGATGATT TTTCGCAAGG GAATGAGAAA TGGTTCAGTC GGCCAAGCAA TTAAGTTGAA    2880

GGGCAAACGG TTCAGATCGA CTTGCGGATA CCAGGTCAGA ATGATACGGA AAATAAACAG    2940

AAATGTCATC ACTCCCAATA CAGGGCCAAG AATCCAAACG CTCAGGTTAA CACCAGTCAT    3000

CGATCTAAGC TACTATTTTG TGAATTTACA AAAAACTGCA AGCAAAAGCT GAAAATTTTA    3060

AGCTT                                                                3065
```

(2) INFORMATION FOR SEQ ID NO:6:

(i) SEQUENCE CHARACTERISTICS:
        (A) LENGTH: 447 amino acids
        (B) TYPE: amino acid
        (C) STRANDEDNESS:
        (D) TOPOLOGY: linear (xi) SEQUENCE DESCRIPTION: SEQ ID NO:6:

```
Met Lys Phe Asp Lys Ile Leu Ile Ala Asn Arg Gly Glu Ile Ala Leu
 1               5                  10                  15

Arg Ile Leu Arg Ala Cys Glu Glu Met Gly Ile Ala Thr Ile Ala Val
                20                  25                  30

His Ser Thr Val Asp Arg Asn Ala Leu His Val Gln Leu Ala Asp Glu
            35                  40                  45

Ala Val Cys Ile Gly Glu Pro Ala Ser Ala Lys Ser Tyr Leu Asn Ile
        50                  55                  60

Pro Asn Ile Ile Ala Ala Leu Thr Arg Asn Ala Ser Ala Ile His
65                  70                  75                  80

Pro Gly Tyr Gly Phe Leu Ser Glu Asn Ala Lys Phe Ala Glu Ile Cys
                85                  90                  95

Ala Asp His His Ile Ala Phe Ile Gly Pro Thr Pro Glu Ala Ile Arg
            100                 105                 110

Leu Met Gly Asp Lys Ser Thr Ala Lys Glu Thr Met Gln Lys Ala Gly
        115                 120                 125

Val Pro Thr Val Pro Gly Ser Glu Gly Leu Val Glu Thr Glu Gln Glu
    130                 135                 140

Gly Leu Glu Leu Ala Lys Asp Ile Gly Tyr Pro Val Met Ile Lys Ala
145                 150                 155                 160

Thr Ala Gly Gly Gly Gly Arg Gly Met Arg Leu Val Arg Ser Pro Asp
                165                 170                 175

Glu Phe Val Lys Leu Phe Leu Ala Ala Gln Gly Glu Ala Gly Ala Ala
            180                 185                 190

Phe Gly Asn Ala Gly Val Tyr Ile Glu Lys Phe Ile Glu Arg Pro Arg
        195                 200                 205
```

```
        His Ile Glu Phe Gln Ile Leu Ala Asp Asn Tyr Gly Asn Val Ile His
            210                 215                 220

Leu Gly Glu Arg Asp Cys Ser Ile Gln Arg Arg Asn Gln Lys Leu Leu
        225                 230                 235                 240

Glu Glu Ala Pro Ser Pro Ala Leu Asp Ser Asp Leu Arg Glu Lys Met
                        245                 250                 255

Gly Gln Ala Ala Val Lys Ala Ala Gln Phe Ile Asn Tyr Thr Gly Ala
                        260                 265                 270

Gly Thr Ile Glu Phe Leu Leu Asp Arg Ser Gly Gln Phe Tyr Phe Met
                    275                 280                 285

Glu Met Asn Thr Arg Ile Gln Val Glu His Pro Val Thr Glu Met Val
        290                 295                 300

Thr Gly Val Asp Leu Leu Val Glu Gln Ile Arg Ile Ala Gln Gly Glu
        305                 310                 315                 320

Arg Leu Arg Leu Thr Gln Asp Gln Val Val Leu Arg Gly His Ala Ile
                        325                 330                 335

Glu Cys Arg Ile Asn Ala Glu Asp Pro Asp His Asp Phe Arg Pro Ala
                        340                 345                 350

Pro Gly Arg Ile Ser Gly Tyr Leu Pro Pro Gly Gly Pro Gly Val Arg
                    355                 360                 365

Ile Asp Ser His Val Tyr Thr Asp Tyr Gln Ile Pro Pro Tyr Tyr Asp
            370                 375                 380

Ser Leu Ile Gly Lys Leu Ile Val Trp Gly Pro Asp Arg Ala Thr Ala
        385                 390                 395                 400

Ile Asn Arg Met Lys Arg Ala Leu Arg Glu Cys Ala Ile Thr Gly Leu
                        405                 410                 415

Pro Thr Thr Ile Gly Phe His Gln Arg Ile Met Glu Asn Pro Gln Phe
                    420                 425                 430

Leu Gln Gly Asn Val Ser Thr Ser Phe Val Gln Glu Met Asn Lys
                435                 440                 445

(2) INFORMATION FOR SEQ ID NO:7:

(i) SEQUENCE CHARACTERISTICS:
        (A) LENGTH: 1362 base pairs
        (B) TYPE: nucleic acid
        (C) STRANDEDNESS: single
        (D) TOPOLOGY: linear (xi) SEQUENCE DESCRIPTION: SEQ ID NO:7:

ATGCGTTTCA CAAGATCCT GATCGCCAAT CGCGGCGAAA TCGCCCTGCG CATTCTCCGC      60

ACTTGTGAAG AACTCGGGAT CGGCACGATC GCCGTTCACT CCACTGTGGA TCGCAACGCG    120

CTCCATGTGC AGTTAGCGGA CGAAGCGGTC TGTATTGGCG AAGCGGCCAG CAGCAAAAGC    180

TATCTCAATA TCCCCAACAT CATTGCGGCG CCCCTGACCC GTAATGCCAG CGCCATTCAC    240

CCCGGCTATG GCTTCTTGGC GGAGAATGCC CGCTTTGCAG AAATCTGCGC CGATCACCAT    300

CTCACCTTTA TTGGCCCCAG CCCCGATTCG ATTCGAGCCA TGGGCGATAA ATCCACCGCT    360

AAGGAAACAA TGCAGCGGGT CGGCGTTCCG ACGATTCCGG CAGTGACGG TCTGCTGACG     420

GATGTTGATT CGGCTGCCAA AGTTGCTGCC GAGATCGGCT ATCCCGTCAT GATCAAAGCG    480

ACGGCGGGGG GCGGTGGTCG CGGTATGCGG CTGGTGCGTG AGCCTGCAGA TCTGGAAAAA    540

CTGTTCCTTG CTGCCCAAGG AGAAGCCGAG GCAGCTTTTG GAATCCAGG ACTGTATCTC     600

GAAAAATTTA TCGATCGCCC ACGCCACGTT GAATTTCAGA TCTTGGCCGA TGCCTACGGC    660

AATGTAGTGC ATCTAGGCGA GCGCGATTGC TCCATTCAAC GTCGTCACCA AAAGCTGCTC    720
```

-continued

```
GAAGAAGCCC CCAGTCCGGC GCTATCGGCA GACCTGCGGC AGAAAATGGG CGATGCCGCC     780

GTCAAAGTCG CTCAAGCGAT CGGCTACATC GGTGCCGGCA CCGTGGAGTT TCTGGTCGAT     840

GCGACCGGCA ACTTCTACTT CATGGAGATG AATACCCGCA TCCAAGTCGA GCATCCAGTC     900

ACAGAAATGA TTACGGGACT GGACTTGATT GCGGAGCAGA TTCGGATTGC CCAAGGCGAA     960

GCGCTGCGCT TCCGGCAAGC CGATATTCAA CTGCGCGGCC ATGCGATCGA ATGCCGTATC    1020

AATGCGGAAG ATCCGGAATA CAATTTCCGG CCGAATCCTG GCCGCATTAC AGGCTATTTA    1080

CCGCCCGGCG GCCCCGGCGT TCGTGTCGAT TCCCATGTTT ATACCGACTA CGAAATTCCG    1140

CCCTATTACG ATTCGCTGAT TGGCAAATTG ATTGTCTGGG GTGCAACACG GGAAGAGGCG    1200

ATCGCGCGGA TGCAGCGTGC TCTGCGGGAA TGCGCCATCA CCGGCTTGCC GACGACCCTT    1260

AGTTTCCATC AGCTGATGTT GCAGATGCCT GAGTTCCTGC GCGGGAACT CTATACCAAC     1320

TTTGTTGAGC AGGTGATGCT ACCTCGGATC CTCAAGTCCT AG                       1362
```

(2) INFORMATION FOR SEQ ID NO:8:

(i) SEQUENCE CHARACTERISTICS:
        (A) LENGTH: 453 amino acids
        (B) TYPE: amino acid
        (C) STRANDEDNESS:
        (D) TOPOLOGY: linear (xi) SEQUENCE DESCRIPTION: SEQ ID NO:8:

```
Met Arg Phe Asn Lys Ile Leu Ile Ala Asn Arg Gly Glu Ile Ala Leu
 1               5                  10                  15

Arg Ile Leu Arg Thr Cys Glu Glu Leu Gly Ile Gly Thr Ile Ala Val
            20                  25                  30

His Ser Thr Val Asp Arg Asn Ala Leu His Val Gln Leu Ala Asp Glu
        35                  40                  45

Ala Val Cys Ile Gly Glu Ala Ala Ser Ser Lys Ser Tyr Leu Asn Ile
    50                  55                  60

Pro Asn Ile Ile Ala Ala Leu Thr Arg Asn Ala Ser Ala Ile His
65                  70                  75                  80

Pro Gly Tyr Gly Phe Leu Ala Glu Asn Ala Arg Phe Ala Glu Ile Cys
                85                  90                  95

Ala Asp His His Leu Thr Phe Ile Gly Pro Ser Pro Asp Ser Ile Arg
            100                 105                 110

Ala Met Gly Asp Lys Ser Thr Ala Lys Glu Thr Met Gln Arg Val Gly
        115                 120                 125

Val Pro Thr Ile Pro Gly Ser Asp Gly Leu Leu Thr Asp Val Asp Ser
    130                 135                 140

Ala Ala Lys Val Ala Ala Glu Ile Gly Tyr Pro Val Met Ile Lys Ala
145                 150                 155                 160

Thr Ala Gly Gly Gly Gly Arg Gly Met Arg Leu Val Arg Glu Pro Ala
                165                 170                 175

Asp Leu Glu Lys Leu Phe Leu Ala Ala Gln Gly Glu Ala Glu Ala Ala
            180                 185                 190

Phe Gly Asn Pro Gly Leu Tyr Leu Glu Lys Phe Ile Asp Arg Pro Arg
        195                 200                 205

His Val Glu Phe Gln Ile Leu Ala Asp Ala Tyr Gly Asn Val Val His
    210                 215                 220

Leu Gly Glu Arg Asp Cys Ser Ile Gln Arg His Gln Lys Leu Leu
225                 230                 235                 240

Glu Glu Ala Pro Ser Pro Ala Leu Ser Ala Asp Leu Arg Gln Lys Met
                245                 250                 255
```

```
        Gly Asp Ala Ala Val Lys Val Ala Gln Ala Ile Gly Tyr Ile Gly Ala
                        260                 265                 270

Gly Thr Val Glu Phe Leu Val Asp Ala Thr Gly Asn Phe Tyr Phe Met
                    275                 280                 285

Glu Met Asn Thr Arg Ile Gln Val Glu His Pro Val Thr Glu Met Ile
                290                 295                 300

Thr Gly Leu Asp Leu Ile Ala Glu Gln Ile Arg Ile Ala Gln Gly Glu
        305                 310                 315                 320

Ala Leu Arg Phe Arg Gln Ala Asp Ile Gln Leu Arg Gly His Ala Ile
                        325                 330                 335

Glu Cys Arg Ile Asn Ala Glu Asp Pro Glu Tyr Asn Phe Arg Pro Asn
                    340                 345                 350

Pro Gly Arg Ile Thr Gly Tyr Leu Pro Pro Gly Gly Pro Gly Val Arg
                355                 360                 365

Val Asp Ser His Val Tyr Thr Asp Tyr Glu Ile Pro Pro Tyr Tyr Asp
                370                 375                 380

Ser Leu Ile Gly Lys Leu Ile Val Trp Gly Ala Thr Arg Glu Glu Ala
        385                 390                 395                 400

Ile Ala Arg Met Gln Arg Ala Leu Arg Glu Cys Ala Ile Thr Gly Leu
                        405                 410                 415

Pro Thr Thr Leu Ser Phe His Gln Leu Met Leu Gln Met Pro Glu Phe
                    420                 425                 430

Leu Arg Gly Glu Leu Tyr Thr Asn Phe Val Glu Gln Val Met Leu Pro
                435                 440                 445

Arg Ile Leu Lys Ser
                450

(2) INFORMATION FOR SEQ ID NO:9:

(i) SEQUENCE CHARACTERISTICS:
        (A) LENGTH: 7360 base pairs
        (B) TYPE: nucleic acid
        (C) STRANDEDNESS: single
        (D) TOPOLOGY: linear (xi) SEQUENCE DESCRIPTION: SEQ ID NO:9:

ATCTCTTTCA ACTTGGATAC CAGGCCGTTG CCTCCGCCGC CGCCGCCTGC CTGCCTCTCC       60

TGGATCTCCA TCTCTCCTTC GCGGCGCGGC ATTCCGTCGA ACGCCTCCGC GGCGCGCCTC      120

CGGGCGGACT CACGTGCTGA AGGTTGGAGG GGGCAATAAT GGTGGAATCT GACCAGATAA      180

ACGGGAGGAT GTCCTCGGTC GACGAGTTCT GTAAAGCGCT CGGGGGCGAC TCGCCGATAC      240

ACAGCGTGCT GGTTGCCAAC AATGGGATGG CTGCGGTCAA GTTCATGCGC AGCATCCGCA      300

CCTGGGCCTT GGAGACCTTT GGGAACGAGA AGGCCATTCT CTTGGTGGCT ATGGCAACTC      360

CAGAGGACCT CAGGATTAAT GCGGAGCACA TAAGAATCGC CGACCAGTTC TTAGAAGTTC      420

CTGGTGGGAC GAATAACAAC AACTATGCAA ATGTACAGCT CATAGTGGAG ATAGCAGAGA      480

GAACTCGGGT TTCTGCAGTT TGGCCTGGCT GGGGTCATGC TTCTGAGAAC CCAGAACTTC      540

CAGACGCGCT CATGGAAAAG GGAATCATTT TTCTTGGGCC ACCATCAGCC GCGATGGGGG      600

CACTAGGCGA TAAGATTGGT TCTTCTCTTA TTGCACAAGC AGCAGGAGTT CCAACTCTTC      660

CATGGAGCGG GTCACATGTG AAAGTTCCGC AAGAAACCTG CCACTCAATA CCTGAGGAGA      720

TCTATAAGAA CGCTTGTGTT TCAACTACAG ACGAAGCAGT CGCTAGTTGT CAGGTGGTGG      780

GGTATCCTGC AATGATCAAG GCATCATGGG GTGGGGGTGG TAAAGGAATA AGGAAGGTAC      840

ACAATGATGA TGAGGTCAGA GCATTGTTTA AGCAAGTGCA AGGAGAGGTC CCCGGATCGC      900
```

```
CTATATTTAT TATGAAGGTG GCATCTCAGA GCCGACATCT AGAGGTTCAG TTGCTCTGTG      960

ACAAGCATGG CAACGTGGCA GCACTGCACA GTCGAGACTG TAGTGTTCAA AGAAGGCACC     1020

AAAAGATCAT TGAGGAGGGA CCAATTACAG TTGCTCCTCC AGAAACAATT AAAGAGCTTG     1080

AGCAGGCGGC AAGGCGACTA GCTAAATGTG TGCAATATCA GGGTGCTGCT ACAGTGGAAT     1140

ATCTGTACAG CATGGAAACA GGCGAATACT ATTTCCTGGA GCTTAATCCA AGGTTGCAGG     1200

TAGAACACCC TGTGACCGAA TGGATTGCTG AAATTAACTT ACCTGCATCT CAAGTTGTAG     1260

TAGGAATGGG CATACCACTC TACAATATTC CAGAGATCAG ACGCTTTTAT GGAATAGAAC     1320

ATGGAGGTGG CTATCACGCT TGGAAGGAAA TATCAGCTGT AGCAACTAAA TTTGATTTGG     1380

ACAAAGCACA GTCTGTAAAG CCAAAGGGTC ATTGTGTAGC AGTTAGAGTT ACTAGCGAGG     1440

ATCCAGATGA TGGGTTTAAG CCTACCAGTG GAAGAGTGGA AGAGCTGAAC TTTAAAAGCA     1500

AACCCAATGT TTGGGCCTAC TTCTCCGTTA AGTCCGGAGG TGCAATTCAT GAGTTCTCTG     1560

ATTCCCAGTT TGGTCATGTT TTTGCTTTTG GGAATCTAG GTCATTGGCA ATAGCCAATA     1620

TGGTACTTGG GTTAAAAGAG ATCCAAATTC GTGGAGAGAT ACGCACTAAT GTTGACTACA     1680

CTGTGGATCT CTTGAATGCT GCAGAGTACC GAGAAAATAA GATTCACACT GGTTGGCTAG     1740

ACAGCAGAAT AGCTATGCGT GTTAGAGCAG AGAGGCCCCC ATGGTACCTT TCAGTTGTTG     1800

GTGGAGCTCT ATATGAAGCA TCAAGCAGGA GCTCGAGCGT TGTAACCGAT TATGTTGGTT     1860

ATCTCAGTAA AGGTCAAATA CCACCAAAGC ACATCTCTCT TGTCAATTTG ACTGTGACAC     1920

TGAATATAGA TGGGGGCAAA TATACGATTG AGACAGTACG AGGTGGACCC CGTAGCTACA     1980

AATTAAGAAT TAATGAATCA GAGGTTGAAG CAGAGATACA TTCTCTGCGA GATGGCGGAC     2040

TCTTAATGCA GTTGGATGGA AACAGTCATG TAATTTACGC CGAGACAGAA GCTGCTGGCA     2100

CGCGCCTTCT AATCAATGGG AGAACATGCT TATTACAGAA AGAGCATGAT CCTTCCAGGT     2160

TGTTGGCTGA TACACCGTGC AAACTTCTTC GGTTTTTGGT CGCGGATGGT TCTCATGTGG     2220

TTGCTGATAC GCCATATGCT GAGGTGGAGG TTATGAAAAT GTGCATGCCA CTGTTACTAC     2280

CGGCCTCTGG TGTCATTCAC TTTGTCATGC CTGAGGGTCA GGCCATGCAG GCAAGTGATC     2340

TGATAGCAAG GTTGGATCTT GATGACCCAT CTTCTGTGAG AAGAGCTGAA CCATTTCATG     2400

GCACCTTTCC AAAACTTGGA CCTCCTACTG CTATTTCTGG CAAAGTTCAC CAAAAGTTTG     2460

CTGCAAGTGT GAATTCTGCC CACATGATCC TTGCAGGATA TGAACATAAC ATCAATCATG     2520

TTGTACAAGA TTTGCTAAAC TGCCTAGACA GCCCTGAGCT CCCTTTCCTA CAGTGGCAAG     2580

AACTCATGTC CGTTTTGGCA ACCCGACTCC CGAAAGATCT TAGGAATGAG TTGGATGCTA     2640

AGTACAAGGA GTATGAGTTG AATGCTGACT TCCGGAAGAG CAAGGATTTC CCTGCCAAGT     2700

TGCTAAGGGG AGTCATTGAG GCTAATCTTG CATACTGTTC CGAGAAGGAT AGGGTTACTA     2760

GTGAGAGGCT TGTAGAGCCA CTTATGAGCC TGGTCAAGTC ATATGAGGGT GGAAGAGAAA     2820

GCCATGCTCG TGCGGTTGTC AAGTCTCTGT TTGAGGAGTA TTTATCTGTT GAAGAACTCT     2880

TCAGCGATGA CATTCAGTCT GATGTGATAG AACGTCTACG ACTTCAACAT GCAAAAGACC     2940

TTGAGAAGGT CGTATATATT GTGTTCTCCC ACCAGGGCGT GAAAAGTAAA AATAAATTAA     3000

TACTTCGGCT TATGGAAGCA TTGGTCTATC CAAATCCATC TGCGTACAGG GACCAGTTGA     3060

TTCGCTTTTC TGCCCTTAAC CATACAGCAT ACTCTGGGCT GGCGCTTAAA GCAAGCCAAC     3120

TTCTTGAGCA CACTAAATTG AGTGAACTCC GCACAAGCAT AGCAAGAAGC CTTTCAGAGC     3180

TGGAGATGTT TACTGAGGAA GGAGAGCGGA TTTCAACACC TAGGAGGAAG ATGGCTATCA     3240

ATGAAAGGAT GGAAGATTTA GTATGTGCCC CGGTTGCAGT TGAAGACGCC CTTGTGGCTT     3300
```

```
TGTTTGATCA CAGTGATCCT ACTCTTCAGC GGAGAGTTGT TGAGACATAC ATACGCAGAT    3360

TGTATCAGCA TTATCTTGTA AGGGGCAGTG TCCGGATGCA ATGGCACAGG TCTGGTCTAA    3420

TTGCTTTATG GGAATTCTCT GAGGAACATA TTGAACAAAG AAATGGGCAA TCTGCGTCAC    3480

TTCTAAAGCC ACAAGTAGAG GATCCAATTG GCAGGCGATG GGGTGTAATG GTTGTAATCA    3540

AGTCTCTTCA GCTTCTGTCA ACTGCAATTG AAGCTGCATT AAAGGAGACT TCACATTACG    3600

GAGCAGGTGT TGGAGGTGTC TCAAATGGTA ATCCTATAAA TTCTAACAGT AGCAATATGC    3660

TGCATATTGC TTTGGTTGGT ATCAACAATC AGATGAGCAC TCTTCAAGAC AGTGGTGATG    3720

AGGATCAAGC GCAAGAAAGG ATCAACAAAC TCTCCAAGAT TTTGAAGGAT AACACTATAA    3780

CATCACATCT CAATGGTGCT GGTGTTAGGG TTGTCAGCTG CATTATCCAA AGAGATGAAG    3840

GGCGTTCACC AATGCGCCAC TCCTTCAAAT GGTCATCTGA CAAGTTATAT TATGAGGAGG    3900

ACCCGATGCT CCGCCATGTG GAACCTCCTT TGTCCACCTT CCTTGAATTG ACAAAGTGA     3960

ATTTAGAAGG TTACAATGAC GCGAAATACA CCCCATCACG TGATCGCCAG TGGCACATGT    4020

ACACACTAGT AAAGAACAAG AAAGATCCGA GATCAAATGA CCAAAGGATG TTTCTTCGTA    4080

CCATAGTCAG ACAGCCAAGT GTGACCAATG GGTTTTTGTT TGGAAGTATT GATAATGAAG    4140

TTCAAGCCTC ATCATCATTC ACATCTAACA GCATACTCAG ATCATTGATG GCAGCGCTAG    4200

AAGAAATAGA GTTGCGCGCT CACAGTGAGA CTGGGATGTC AGGCCACTCC CACATGTATC    4260

TGTGCATAAT GAGAGAACAG CGGTTGTTTG ATCTAATTCC ATCTTCAAGG ATGACGAATG    4320

AAGTTGGTCA AGATGAGAAG ACAGCATGCA CATTATTGAA GCATATGGGT ATGATATATA    4380

TGAGCATGTG GTGTCAGGAT GCATCGCTTT CTGTGTGCCA GTGGGAAGTG AAGCTATGGT    4440

TGGATTGTGA TGGGCAGGCT AATGGTGCTT GGAGAGTTGT TGTTACCAGT GTAACTGGGC    4500

ATACCTGCAC TGTTGATATT TACCGAGAAG TGGAGGACCC CAATACACAT CAGCTTTTCT    4560

ACCGCTCTGC CACACCCACA GCTGGTCCTT TGCATGGCAT TGCATTGCAT GAGCCATACA    4620

AACCTTTGGA TGCTATTGAC CTGAAACGTG CCGCTGCTAG GAAAAATGAA ACCACATACT    4680

GCTATGATTT CCCATTGGCA TTTGAAACAG CATTGAAGAA GTCATGGGAA TCTGGTATTT    4740

CACATGTTGC AGAATCTAAC GAGCATAACC AGCGGTATGC TGAAGTGACA GAGCTTATAT    4800

TTGCTGATTC AACTGGATCA TGGGGTACTC CTTTGGTTCC AGTTGAGCGT CCTCCAGGTA    4860

GCAACAATTT TGGTGTTGTT GCTTGGAACA TGAAGCTCTC CACACCAGAA TTTCCAGGCG    4920

GCCGGGAGAT TATAGTTGTT GCAAATGATG TGACATTTAA AGCTGGGTCT TTTGGTCCTA    4980

GAGAAGATGC ATTCTTTGAT GCTGTCACCA ATCTTGCTTG TGAGAGGAAA ATTCCTCTAA    5040

TTTACTTGTC AGCAACTGCT GGTGCTAGGC TCGGTGTAGC AGAGGAAATA AAGGCGTGCT    5100

TCCATGTTGG ATGGTCTGAT GACCAGAGCC CTGAACGTGG TTTTCACTAC ATTTACCTCA    5160

CTGAACAAGA TTATTCACGT CTAAGCTCTT CAGTTATAGC CCATGAGCTA AAAGTACCGG    5220

AAAGCGGAGA AACCAGATGG GTTGTTGATA CCATTGTTGG GAAAGAGGAC GGACTTGGTT    5280

GTGAGAATCT ACATGGAAGT GGTGCCATTG CCAGTGCCTA CTCTAAGGCA TACAGAGAGA    5340

CCTTTACTCT GACATTTGTG ACTGGGCGAG CTATTGGAAT TGGGGCTTAT CTTGCTCGGT    5400

TAGGAATGCG GTGTATACAA CGTCTTGATC AACCAATTAT TTTGACTGGG TATTCTGCAC    5460

TGAACAAGCT CCTGGGGCGC GAGGTGTATA GCTCTCAGAT GCAACTGGGT GGCCCCAAAA    5520

TCATGGCTAC AAATGGAGTT GTCCATCTCA CTGTGTCAGA TGATCTTGAA GGTGTTTCTG    5580

CTATCTTGAA ATGGCTCAGC TATGTTCCTC CCTATGTTGG CGGTCCTCTT CCTATTGTGA    5640

AATCTCTTGA TCCACCAGAG AGAGCTGTAA CATATTTCCC AGAGAATTCA TGTGATGCCC    5700
```

```
GTGCCGCCAT CTGTGGCATC CAGGACACTC AAGGAGGCAA GTGGTTGGAT GGTATGTTTG    5760

ACAGAGAAAG CTTTGTGGAA ACATTAGAAG GATGGGCCAA AACTGTTATT ACTGGAAGGG    5820

CAAAGCTAGG TGGGATTCCA GTTGGTATCA TAGCTGTGGA AACCGAGACA GTGATGCAAG    5880

TAATCCCTGC TGACCCTGGT CAGCTTGATT CTGCCGAGCG TGTAGTCCCT CAAGCTGGAC    5940

AGGTGTGGTT CCCAGATTCG GCCGCAAAAA CGGGCCAGGC ACTGCTGGAT TTCAACCGTG    6000

AAGAGCTCCC ATTGTTCATA CTTGCTAACT GGAGAGGCTT TTCTGGTGGG CAAAGGGATC    6060

TGTTTGAAGG AATCCTTCAG GCTGGCTCTA TGATTGTTGA GAATCTGAGG ACGTATAAGC    6120

AGCCTGCTTT TGTGTACATA CCAAAGGCTG GAGAGCTGCG TGGAGGTGCA TGGGTTGTGG    6180

TGGACAGCAA GATCAATCCT GAGCACATTG AGATGTATGC CGAGAGGACT GCGAGAGGGA    6240

ATGTCCTTGA GGCACCAGGA CTCATTGAGA TCAAGTTCAA GCCAAATGAA CTGGAAGAGA    6300

GTATGCTAAG GCTGACCCT GAGTTGATCA GCCTCAATGC CAAACTCCTC AAAGAAACTA    6360

GTGCTAGCCC TAGTCCTTGG GAAACGGCGG CGGCGGCGGA GACCATCAGG AGGAGCATGG    6420

CTGCTCGGAG GAAGCAGCTG ATGCCCATAT ATACTCAGGT TGCCACCCGG TTTGCTGAGT    6480

TGCACGACAC CTCTGCGAGA ATGGCTGCCA AAGGCGTGAT CAGTAAGGTG GTGGACTGGG    6540

AGGAGTCCCG AGCCTTCTTC TACAGGAGAC TGCGAAGGAG GCTTGCCGAG GACTCGCTCG    6600

CCAAACAAGT CAGAGAAGCC GCCGGCGAGC AGCAGATGCC CACTCACAGA TCGGCCTTGG    6660

AATGCATCAA GAAATGGTAC CTGGCCTCTC AGGGAGGAGA CGGCGAGAAG TGGGGAGACG    6720

ATGAAGCCTT CTTCGCCTGG AAAGATGATC CTGACAAGTA TGGCAAGTAT CTTGAGGAGC    6780

TGAAAGCCGA GAGAGCGTCT ACACTGCTGT CGCATCTCGC TGAAACCTCT GATGCCAAGG    6840

CCTTGCCCAA CGGTCTATCG CTCCTCCTCA GCAAAATGGA TCCTGCAAAG AGGGAGCAGG    6900

TTATGGATGG CCTCAGGCAG CTTCTTGGTT GATGACTGGC CCACCCTTTG ATAACGGGAG    6960

CATCCATTCA GCCAGCATAA ACCGGCCTTG CTTGTTGCCA CCAAGCAAGT CCTGTCTATG    7020

GTGGACTGGG TACCAACGGA AGCGCAGACG ACGACAAGCA AATTTTACTT GCGTGGCGAG    7080

CTACAGGAGG GGGAGGTTTT TCAACTGAAA CACATTGTTT GCACATAGGT AGGAGGCATC    7140

TCATCTCAGG ACAATTTGTA TGTTTATTGT TATTACAGAT AGGTACACAC AAAGCATATG    7200

TATGCTGGAT AGATATTCGG TGTGAGTTGT TGCAATGCAA GATTCATCAT CTTAATTTAC    7260

GAGATACGTG TGATGGTCGA TGTGATAGTC CTAGTTTCCT CGGTGGCGAG GAACGCTGAG    7320

TTTCCTTTTG CTGCAGTTAT GTGATGTATA CCCTGAGAAC                          7360
```

(2) INFORMATION FOR SEQ ID NO:10:

(i) SEQUENCE CHARACTERISTICS:
        (A) LENGTH: 2257 amino acids
        (B) TYPE: amino acid
        (C) STRANDEDNESS:
        (D) TOPOLOGY: linear (xi) SEQUENCE DESCRIPTION: SEQ ID NO:10:

```
Met Val Glu Ser Asp Gln Ile Asn Gly Arg Met Ser Ser Val Asp Glu
  1               5                  10                  15

Phe Cys Lys Ala Leu Gly Gly Asp Ser Pro Ile His Ser Val Leu Val
             20                  25                  30

Ala Asn Asn Gly Met Ala Ala Val Lys Phe Met Arg Ser Ile Arg Thr
         35                  40                  45

Trp Ala Leu Glu Thr Phe Gly Asn Glu Lys Ala Ile Leu Leu Val Ala
     50                  55                  60
```

```
Met Ala Thr Pro Glu Asp Leu Arg Ile Asn Ala Glu His Ile Arg Ile
 65                  70                  75                  80

Ala Asp Gln Phe Leu Glu Val Pro Gly Gly Thr Asn Asn Asn Asn Tyr
             85                  90                  95

Ala Asn Val Gln Leu Ile Val Glu Ile Ala Glu Arg Thr Arg Val Ser
            100                 105                 110

Ala Val Trp Pro Gly Trp Gly His Ala Ser Glu Asn Pro Glu Leu Pro
            115                 120                 125

Asp Ala Leu Met Glu Lys Gly Ile Ile Phe Leu Gly Pro Pro Ser Ala
130                 135                 140

Ala Met Gly Ala Leu Gly Asp Lys Ile Gly Ser Ser Leu Ile Ala Gln
145                 150                 155                 160

Ala Ala Gly Val Pro Thr Leu Pro Trp Ser Gly Ser His Val Lys Val
            165                 170                 175

Pro Gln Glu Thr Cys His Ser Ile Pro Glu Glu Ile Tyr Lys Asn Ala
            180                 185                 190

Cys Val Ser Thr Thr Asp Glu Ala Val Ala Ser Cys Gln Val Val Gly
            195                 200                 205

Tyr Pro Ala Met Ile Lys Ala Ser Trp Gly Gly Gly Lys Gly Ile
210                 215                 220

Arg Lys Val His Asn Asp Asp Glu Val Arg Ala Leu Phe Lys Gln Val
225                 230                 235                 240

Gln Gly Glu Val Pro Gly Ser Pro Ile Phe Ile Met Lys Val Ala Ser
            245                 250                 255

Gln Ser Arg His Leu Glu Val Gln Leu Leu Cys Asp Lys His Gly Asn
            260                 265                 270

Val Ala Ala Leu His Ser Arg Asp Cys Ser Val Gln Arg Arg His Gln
            275                 280                 285

Lys Ile Ile Glu Glu Gly Pro Ile Thr Val Ala Pro Pro Glu Thr Ile
290                 295                 300

Lys Glu Leu Glu Gln Ala Ala Arg Arg Leu Ala Lys Cys Val Gln Tyr
305                 310                 315                 320

Gln Gly Ala Ala Thr Val Glu Tyr Leu Tyr Ser Met Glu Thr Gly Glu
            325                 330                 335

Tyr Tyr Phe Leu Glu Leu Asn Pro Arg Leu Gln Val Glu His Pro Val
            340                 345                 350

Thr Glu Trp Ile Ala Glu Ile Asn Leu Pro Ala Ser Gln Val Val Val
            355                 360                 365

Gly Met Gly Ile Pro Leu Tyr Asn Ile Pro Glu Ile Arg Arg Phe Tyr
            370                 375                 380

Gly Ile Glu His Gly Gly Gly Tyr His Ala Trp Lys Glu Ile Ser Ala
385                 390                 395                 400

Val Ala Thr Lys Phe Asp Leu Asp Lys Ala Gln Ser Val Lys Pro Lys
            405                 410                 415

Gly His Cys Val Ala Val Arg Val Thr Ser Glu Asp Pro Asp Asp Gly
            420                 425                 430

Phe Lys Pro Thr Ser Gly Arg Val Glu Glu Leu Asn Phe Lys Ser Lys
            435                 440                 445

Pro Asn Val Trp Ala Tyr Phe Ser Val Lys Ser Gly Gly Ala Ile His
            450                 455                 460

Glu Phe Ser Asp Ser Gln Phe Gly His Val Phe Ala Phe Gly Glu Ser
465                 470                 475                 480

Arg Ser Leu Ala Ile Ala Asn Met Val Leu Gly Leu Lys Glu Ile Gln
            485                 490                 495
```

-continued

```
Ile Arg Gly Glu Ile Arg Thr Asn Val Asp Tyr Thr Val Asp Leu Leu
            500                 505                 510
Asn Ala Ala Glu Tyr Arg Glu Asn Lys Ile His Thr Gly Trp Leu Asp
            515                 520                 525
Ser Arg Ile Ala Met Arg Val Arg Ala Glu Arg Pro Pro Trp Tyr Leu
            530                 535                 540
Ser Val Val Gly Gly Ala Leu Tyr Glu Ala Ser Ser Arg Ser Ser Ser
545                 550                 555                 560
Val Val Thr Asp Tyr Val Gly Tyr Leu Ser Lys Gly Gln Ile Pro Pro
            565                 570                 575
Lys His Ile Ser Leu Val Asn Leu Thr Val Thr Leu Asn Ile Asp Gly
            580                 585                 590
Gly Lys Tyr Thr Ile Glu Thr Val Arg Gly Pro Arg Ser Tyr Lys
            595                 600                 605
Leu Arg Ile Asn Glu Ser Glu Val Glu Ala Glu Ile His Ser Leu Arg
            610                 615                 620
Asp Gly Gly Leu Leu Met Gln Leu Asp Gly Asn Ser His Val Ile Tyr
625                 630                 635                 640
Ala Glu Thr Glu Ala Ala Gly Thr Arg Leu Leu Ile Asn Gly Arg Thr
            645                 650                 655
Cys Leu Leu Gln Lys Glu His Asp Pro Ser Arg Leu Leu Ala Asp Thr
            660                 665                 670
Pro Cys Lys Leu Leu Arg Phe Leu Val Ala Asp Gly Ser His Val Val
            675                 680                 685
Ala Asp Thr Pro Tyr Ala Glu Val Glu Val Met Lys Met Cys Met Pro
            690                 695                 700
Leu Leu Leu Pro Ala Ser Gly Val Ile His Phe Val Met Pro Glu Gly
705                 710                 715                 720
Gln Ala Met Gln Ala Ser Asp Leu Ile Ala Arg Leu Asp Leu Asp Asp
            725                 730                 735
Pro Ser Ser Val Arg Arg Ala Glu Pro Phe His Gly Thr Phe Pro Lys
            740                 745                 750
Leu Gly Pro Pro Thr Ala Ile Ser Gly Lys Val His Gln Lys Phe Ala
            755                 760                 765
Ala Ser Val Asn Ser Ala His Met Ile Leu Ala Gly Tyr Glu His Asn
            770                 775                 780
Ile Asn His Val Val Gln Asp Leu Leu Asn Cys Leu Asp Ser Pro Glu
785                 790                 795                 800
Leu Pro Phe Leu Gln Trp Gln Glu Leu Met Ser Val Leu Ala Thr Arg
            805                 810                 815
Leu Pro Lys Asp Leu Arg Asn Glu Leu Asp Ala Lys Tyr Lys Glu Tyr
            820                 825                 830
Glu Leu Asn Ala Asp Phe Arg Lys Ser Lys Asp Phe Pro Ala Lys Leu
            835                 840                 845
Leu Arg Gly Val Ile Glu Ala Asn Leu Ala Tyr Cys Ser Glu Lys Asp
            850                 855                 860
Arg Val Thr Ser Glu Arg Leu Val Glu Pro Leu Met Ser Leu Val Lys
865                 870                 875                 880
Ser Tyr Glu Gly Gly Arg Glu Ser His Ala Arg Ala Val Val Lys Ser
            885                 890                 895
Leu Phe Glu Glu Tyr Leu Ser Val Glu Glu Leu Phe Ser Asp Asp Ile
            900                 905                 910
Gln Ser Asp Val Ile Glu Arg Leu Arg Leu Gln His Ala Lys Asp Leu
```

```
                    915                 920                 925
Glu Lys Val Val Tyr Ile Val Phe Ser His Gln Gly Val Lys Ser Lys
                930                 935                 940
Asn Lys Leu Ile Leu Arg Leu Met Glu Ala Leu Val Tyr Pro Asn Pro
945                 950                 955                 960
Ser Ala Tyr Arg Asp Gln Leu Ile Arg Phe Ser Ala Leu Asn His Thr
                965                 970                 975
Ala Tyr Ser Gly Leu Ala Leu Lys Ala Ser Gln Leu Leu Glu His Thr
                980                 985                 990
Lys Leu Ser Glu Leu Arg Thr Ser Ile Ala Arg Ser Leu Ser Glu Leu
                995                 1000                1005
Glu Met Phe Thr Glu Glu Gly Glu Arg Ile Ser Thr Pro Arg Arg Lys
                1010                1015                1020
Met Ala Ile Asn Glu Arg Met Glu Asp Leu Val Cys Ala Pro Val Ala
1025                1030                1035                1040
Val Glu Asp Ala Leu Val Ala Leu Phe Asp His Ser Asp Pro Thr Leu
                1045                1050                1055
Gln Arg Arg Val Val Glu Thr Tyr Ile Arg Arg Leu Tyr Gln His Tyr
                1060                1065                1070
Leu Val Arg Gly Ser Val Arg Met Gln Trp His Arg Ser Gly Leu Ile
                1075                1080                1085
Ala Leu Trp Glu Phe Ser Glu Glu His Ile Glu Gln Arg Asn Gly Gln
                1090                1095                1100
Ser Ala Ser Leu Leu Lys Pro Gln Val Glu Asp Pro Ile Gly Arg Arg
1105                1110                1115                1120
Trp Gly Val Met Val Val Ile Lys Ser Leu Gln Leu Leu Ser Thr Ala
                1125                1130                1135
Ile Glu Ala Ala Leu Lys Glu Thr Ser His Tyr Gly Ala Gly Val Gly
                1140                1145                1150
Gly Val Ser Asn Gly Asn Pro Ile Asn Ser Asn Ser Ser Asn Met Leu
                1155                1160                1165
His Ile Ala Leu Val Gly Ile Asn Asn Gln Met Ser Thr Leu Gln Asp
                1170                1175                1180
Ser Gly Asp Glu Asp Gln Ala Gln Glu Arg Ile Asn Lys Leu Ser Lys
1185                1190                1195                1200
Ile Leu Lys Asp Asn Thr Ile Thr Ser His Leu Asn Gly Ala Gly Val
                1205                1210                1215
Arg Val Val Ser Cys Ile Ile Gln Arg Asp Glu Gly Arg Ser Pro Met
                1220                1225                1230
Arg His Ser Phe Lys Trp Ser Ser Asp Lys Leu Tyr Tyr Glu Glu Asp
                1235                1240                1245
Pro Met Leu Arg His Val Glu Pro Pro Leu Ser Thr Phe Leu Glu Leu
                1250                1255                1260
Asp Lys Val Asn Leu Glu Gly Tyr Asn Asp Ala Lys Tyr Thr Pro Ser
1265                1270                1275                1280
Arg Asp Arg Gln Trp His Met Tyr Thr Leu Val Lys Asn Lys Lys Asp
                1285                1290                1295
Pro Arg Ser Asn Asp Gln Arg Met Phe Leu Arg Thr Ile Val Arg Gln
                1300                1305                1310
Pro Ser Val Thr Asn Gly Phe Leu Phe Gly Ser Ile Asp Asn Glu Val
                1315                1320                1325
Gln Ala Ser Ser Ser Phe Thr Ser Asn Ser Ile Leu Arg Ser Leu Met
                1330                1335                1340
```

```
Ala Ala Leu Glu Glu Ile Glu Leu Arg Ala His Ser Glu Thr Gly Met
1345                1350                1355                1360

Ser Gly His Ser His Met Tyr Leu Cys Ile Met Arg Glu Gln Arg Leu
            1365                1370                1375

Phe Asp Leu Ile Pro Ser Ser Arg Met Thr Asn Glu Val Gly Gln Asp
            1380                1385                1390

Glu Lys Thr Ala Cys Thr Leu Leu Lys His Met Gly Met Ile Tyr Met
        1395                1400                1405

Ser Met Trp Cys Gln Asp Ala Ser Leu Ser Val Cys Gln Trp Glu Val
    1410                1415                1420

Lys Leu Trp Leu Asp Cys Asp Gly Gln Ala Asn Gly Ala Trp Arg Val
1425                1430                1435                1440

Val Val Thr Ser Val Thr Gly His Thr Cys Thr Val Asp Ile Tyr Arg
                1445                1450                1455

Glu Val Glu Asp Pro Asn Thr His Gln Leu Phe Tyr Arg Ser Ala Thr
            1460                1465                1470

Pro Thr Ala Gly Pro Leu His Gly Ile Ala Leu His Glu Pro Tyr Lys
        1475                1480                1485

Pro Leu Asp Ala Ile Asp Leu Lys Arg Ala Ala Arg Lys Asn Glu
    1490                1495                1500

Thr Thr Tyr Cys Tyr Asp Phe Pro Leu Ala Phe Glu Thr Ala Leu Lys
1505                1510                1515                1520

Lys Ser Trp Glu Ser Gly Ile Ser His Val Ala Glu Ser Asn Glu His
                1525                1530                1535

Asn Gln Arg Tyr Ala Glu Val Thr Glu Leu Ile Phe Ala Asp Ser Thr
            1540                1545                1550

Gly Ser Trp Gly Thr Pro Leu Val Pro Val Glu Arg Pro Pro Gly Ser
        1555                1560                1565

Asn Asn Phe Gly Val Val Ala Trp Asn Met Lys Leu Ser Thr Pro Glu
    1570                1575                1580

Phe Pro Gly Gly Arg Glu Ile Ile Val Val Ala Asn Asp Val Thr Phe
1585                1590                1595                1600

Lys Ala Gly Ser Phe Gly Pro Arg Glu Asp Ala Phe Phe Asp Ala Val
                1605                1610                1615

Thr Asn Leu Ala Cys Glu Arg Lys Ile Pro Leu Ile Tyr Leu Ser Ala
            1620                1625                1630

Thr Ala Gly Ala Arg Leu Gly Val Ala Glu Glu Ile Lys Ala Cys Phe
        1635                1640                1645

His Val Gly Trp Ser Asp Asp Gln Ser Pro Glu Arg Gly Phe His Tyr
    1650                1655                1660

Ile Tyr Leu Thr Glu Gln Asp Tyr Ser Arg Leu Ser Ser Ser Val Ile
1665                1670                1675                1680

Ala His Glu Leu Lys Val Pro Glu Ser Gly Glu Thr Arg Trp Val Val
                1685                1690                1695

Asp Thr Ile Val Gly Lys Glu Asp Gly Leu Gly Cys Glu Asn Leu His
            1700                1705                1710

Gly Ser Gly Ala Ile Ala Ser Ala Tyr Ser Lys Ala Tyr Arg Glu Thr
        1715                1720                1725

Phe Thr Leu Thr Phe Val Thr Gly Arg Ala Ile Gly Ile Gly Ala Tyr
    1730                1735                1740

Leu Ala Arg Leu Gly Met Arg Cys Ile Gln Arg Leu Asp Gln Pro Ile
1745                1750                1755                1760

Ile Leu Thr Gly Tyr Ser Ala Leu Asn Lys Leu Leu Gly Arg Glu Val
                1765                1770                1775
```

-continued

Tyr Ser Ser Gln Met Gln Leu Gly Gly Pro Lys Ile Met Ala Thr Asn
            1780                1785                1790

Gly Val Val His Leu Thr Val Ser Asp Asp Leu Glu Gly Val Ser Ala
        1795                1800                1805

Ile Leu Lys Trp Leu Ser Tyr Val Pro Pro Tyr Val Gly Gly Pro Leu
        1810                1815                1820

Pro Ile Val Lys Ser Leu Asp Pro Pro Glu Arg Ala Val Thr Tyr Phe
1825                1830                1835                1840

Pro Glu Asn Ser Cys Asp Ala Arg Ala Ala Ile Cys Gly Ile Gln Asp
                1845                1850                1855

Thr Gln Gly Gly Lys Trp Leu Asp Gly Met Phe Asp Arg Glu Ser Phe
                1860                1865                1870

Val Glu Thr Leu Glu Gly Trp Ala Lys Thr Val Ile Thr Gly Arg Ala
            1875                1880                1885

Lys Leu Gly Gly Ile Pro Val Gly Ile Ile Ala Val Glu Thr Glu Thr
            1890                1895                1900

Val Met Gln Val Ile Pro Ala Asp Pro Gly Gln Leu Asp Ser Ala Glu
1905                1910                1915                1920

Arg Val Val Pro Gln Ala Gly Gln Val Trp Phe Pro Asp Ser Ala Ala
                1925                1930                1935

Lys Thr Gly Gln Ala Leu Leu Asp Phe Asn Arg Glu Glu Leu Pro Leu
            1940                1945                1950

Phe Ile Leu Ala Asn Trp Arg Gly Phe Ser Gly Gly Gln Arg Asp Leu
            1955                1960                1965

Phe Glu Gly Ile Leu Gln Ala Gly Ser Met Ile Val Glu Asn Leu Arg
        1970                1975                1980

Thr Tyr Lys Gln Pro Ala Phe Val Tyr Ile Pro Lys Ala Gly Glu Leu
1985                1990                1995                2000

Arg Gly Gly Ala Trp Val Val Val Asp Ser Lys Ile Asn Pro Glu His
                2005                2010                2015

Ile Glu Met Tyr Ala Glu Arg Thr Ala Arg Gly Asn Val Leu Glu Ala
            2020                2025                2030

Pro Gly Leu Ile Glu Ile Lys Phe Lys Pro Asn Glu Leu Glu Glu Ser
            2035                2040                2045

Met Leu Arg Leu Asp Pro Glu Leu Ile Ser Leu Asn Ala Lys Leu Leu
        2050                2055                2060

Lys Glu Thr Ser Ala Ser Pro Ser Pro Trp Glu Thr Ala Ala Ala Ala
2065                2070                2075                2080

Glu Thr Ile Arg Arg Ser Met Ala Ala Arg Arg Lys Gln Leu Met Pro
                2085                2090                2095

Ile Tyr Thr Gln Val Ala Thr Arg Phe Ala Glu Leu His Asp Thr Ser
            2100                2105                2110

Ala Arg Met Ala Ala Lys Gly Val Ile Ser Lys Val Val Asp Trp Glu
        2115                2120                2125

Glu Ser Arg Ala Phe Phe Tyr Arg Arg Leu Arg Arg Arg Leu Ala Glu
            2130                2135                2140

Asp Ser Leu Ala Lys Gln Val Arg Glu Ala Ala Gly Glu Gln Gln Met
2145                2150                2155                2160

Pro Thr His Arg Ser Ala Leu Glu Cys Ile Lys Lys Trp Tyr Leu Ala
                2165                2170                2175

Ser Gln Gly Gly Asp Gly Glu Lys Trp Gly Asp Asp Glu Ala Phe Phe
            2180                2185                2190

Ala Trp Lys Asp Asp Pro Asp Lys Tyr Gly Lys Tyr Leu Glu Glu Leu

```
                   2195              2200              2205
        Lys Ala Glu Arg Ala Ser Thr Leu Leu Ser His Leu Ala Glu Thr Ser
            2210              2215              2220

Asp Ala Lys Ala Leu Pro Asn Gly Leu Ser Leu Leu Leu Ser Lys Met
        2225              2230              2235              2240

Asp Pro Ala Lys Arg Glu Gln Val Met Asp Gly Leu Arg Gln Leu Leu
                          2245              2250              2255

Gly
```

(2) INFORMATION FOR SEQ ID NO:11:

(i) SEQUENCE CHARACTERISTICS:
        (A) LENGTH: 984 base pairs
        (B) TYPE: nucleic acid
        (C) STRANDEDNESS: single
        (D) TOPOLOGY: linear (xi) SEQUENCE DESCRIPTION: SEQ ID NO:11:

```
ATGGCTGCAC CTGTCACGAA GAAGCCAATT CTGCTGGAGT TTGAAAAGCC CCTAGTTGAG    60

CTGGAGGAAC GGATCACGCA AATCCGCACC CTCGCAGCGG ACAACCAGGT GGATGTGAGC   120

GGCCAAATTC AGCAACTGGA AGCCCGGGCG ATTCAACTGC GGCGAGAAAT TTTTAGTAAT   180

CTCTCGCCAG CCCAGCGCAT CCAAGTGGCG CGTCATCCCC GACGTCCGAG TACCTTGGAC   240

TACATCCAAG CGATCAGCGA CGAGTGGATT GAATTACACG GCGATCGCAA CGGTAGTGAT   300

GACCTCGCAC TCGTGGGTGG TGTTGGTGCG CTCGACGGCC AGCCAGTCGT TTTCTTGGGC   360

CACCAAAAGG GGCGCGACAC CAAGGACAAC GTGCTGCGCA ACTTCGGGAT GGCTTCACCC   420

GGCGGCTATC GCAAGGCACT GCGTTTGATG GAGCATGCCG ATCGCTTCGG GATGCCGATT   480

CTGACCTTTA TCGATACACC CGGTGCTTAC GCTGGGGTCA GTGCTGAAGA ACTGGGTCAA   540

GGTGAGGCAA TCGCAGTCAA CCTGCGCGAA ATGTTCCGCT TCTCGGTGCC GATTCTCTGC   600

ACAGTGATTG GCGAAGGCGG TTCGGGCGGG GCCTTGGGCA TTGGCGTCGG CGATCGCCTG   660

CTGATGTTTG AGCATTCCGT CTACACTGTT GCCAGTCCCG AAGCCTGCGC ATCAATTCTC   720

TGGCGTGATG CGGGCAAGGC AGCCCAGGCG GCAGAAGCGC TCAAGATTAC GGCGCGAGAC   780

CTCAAGCAAT TAGGCATCCT TGACGAAATC ATCACCGAAC CTTTGGGCGG TGCCCATTCT   840

GCACCGCTGG AAACGGCCCA GAGTTTGCGT CAGGTTTTGC TGCGCCATCT GAAGGATTTG   900

CAAGCCCTCA GTCCGGCTCA GTTGCGCGAG CAGCGTTATC AAAAGTTTCG CCAGCTCGGG   960

GTGTTTCTGG AAAGCAGTGA CTAA                                         984
```

(2) INFORMATION FOR SEQ ID NO:12:

(i) SEQUENCE CHARACTERISTICS:
        (A) LENGTH: 327 amino acids
        (B) TYPE: amino acid
        (C) STRANDEDNESS:
        (D) TOPOLOGY: linear (xi) SEQUENCE DESCRIPTION: SEQ ID NO:12:

```
        Met Ala Ala Pro Val Thr Lys Lys Pro Ile Leu Leu Glu Phe Glu Lys
        1               5                   10                  15

Pro Leu Val Glu Leu Glu Glu Arg Ile Thr Gln Ile Arg Thr Leu Ala
                        20                  25                  30

Ala Asp Asn Gln Val Asp Val Ser Gly Gln Ile Gln Leu Glu Ala
                    35                  40                  45

Arg Ala Ile Gln Leu Arg Arg Glu Ile Phe Ser Asn Leu Ser Pro Ala
        50                  55                  60
```

```
Gln Arg Ile Gln Val Ala Arg His Pro Arg Arg Pro Ser Thr Leu Asp
 65                  70                  75                  80

Tyr Ile Gln Ala Ile Ser Asp Glu Trp Ile Glu Leu His Gly Asp Arg
                 85                  90                  95

Asn Gly Ser Asp Asp Leu Ala Leu Val Gly Val Gly Ala Leu Asp
            100                 105                 110

Gly Gln Pro Val Val Phe Leu Gly His Gln Lys Gly Arg Asp Thr Lys
        115                 120                 125

Asp Asn Val Leu Arg Asn Phe Gly Met Ala Ser Pro Gly Gly Tyr Arg
    130                 135                 140

Lys Ala Leu Arg Leu Met Glu His Ala Asp Arg Phe Gly Met Pro Ile
145                 150                 155                 160

Leu Thr Phe Ile Asp Thr Pro Gly Ala Tyr Ala Gly Val Ser Ala Glu
                165                 170                 175

Glu Leu Gly Gln Gly Glu Ala Ile Ala Val Asn Leu Arg Glu Met Phe
            180                 185                 190

Arg Phe Ser Val Pro Ile Leu Cys Thr Val Ile Gly Glu Gly Gly Ser
        195                 200                 205

Gly Gly Ala Leu Gly Ile Gly Val Gly Asp Arg Leu Leu Met Phe Glu
210                 215                 220

His Ser Val Tyr Thr Val Ala Ser Pro Glu Ala Cys Ala Ser Ile Leu
225                 230                 235                 240

Trp Arg Asp Ala Gly Lys Ala Ala Gln Ala Ala Glu Ala Leu Lys Ile
                245                 250                 255

Thr Ala Arg Asp Leu Lys Gln Leu Gly Ile Leu Asp Glu Ile Ile Thr
            260                 265                 270

Glu Pro Leu Gly Gly Ala His Ser Ala Pro Leu Glu Thr Ala Gln Ser
        275                 280                 285

Leu Arg Gln Val Leu Leu Arg His Leu Lys Asp Leu Gln Ala Leu Ser
    290                 295                 300

Pro Ala Gln Leu Arg Glu Gln Arg Tyr Gln Lys Phe Arg Gln Leu Gly
305                 310                 315                 320

Val Phe Leu Glu Ser Ser Asp
                325

(2) INFORMATION FOR SEQ ID NO:13:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: one-of(11, 14)
        (D) OTHER INFORMATION: /mod_base= OTHER
            /note= "N = A, C, G, or T"

(ix) FEATURE:
        (A) NAME/KEY: modified_base
        (B) LOCATION: 20
        (D) OTHER INFORMATION: /mod_base= OTHER
            /note= "R = A or G"

(ix) FEATURE:
        (A) NAME/KEY: modified_base
        (B) LOCATION: 17
        (D) OTHER INFORMATION: /mod_base= OTHER
            /note= "H = A, C, or T"

(xi) SEQUENCE DESCRIPTION: SEQ ID NO:13:
```

TCGAATTCGT NATNATHAAR GC									22

(2) INFORMATION FOR SEQ ID NO:14:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: one-of(3, 9)
        (D) OTHER INFORMATION: /mod_base= OTHER
            /note= "Y = C or T"

(ix) FEATURE:
        (A) NAME/KEY: modified_base
        (B) LOCATION: 6
        (D) OTHER INFORMATION: /mod_base= OTHER
            /note= "N = A, C, G, or T"

(ix) FEATURE:
        (A) NAME/KEY: modified_base
        (B) LOCATION: 13
        (D) OTHER INFORMATION: /mod_base= OTHER
            /note= "K = G or T"

(ix) FEATURE:
        (A) NAME/KEY: modified_base
        (B) LOCATION: 12
        (D) OTHER INFORMATION: /mod_base= OTHER
            /note= "R = A or G"

(xi) SEQUENCE DESCRIPTION: SEQ ID NO:14:

GTYCANCTYG TRKGAGATCT CG									22

(2) INFORMATION FOR SEQ ID NO:15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:15:

GCTCTAGAAT ACTATTTCCT G									21

(2) INFORMATION FOR SEQ ID NO:16:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: one-of(3, 9)
        (D) OTHER INFORMATION: /mod_base= OTHER
            /note= "Y = C or T"

(ix) FEATURE:
        (A) NAME/KEY: modified_base
        (B) LOCATION: 6
        (D) OTHER INFORMATION: /mod_base= OTHER
            /note= "N = A, C, G, or T"

(ix) FEATURE:
        (A) NAME/KEY: modified_base
        (B) LOCATION: 12
        (D) OTHER INFORMATION: /mod_base= OTHER
            /note= "R = A or G"

```
         (ix) FEATURE:
               (A) NAME/KEY: modified_base
               (B) LOCATION: 13
               (D) OTHER INFORMATION: /mod_base= OTHER
                   /note= "K = G or T"

(xi) SEQUENCE DESCRIPTION: SEQ ID NO:16:

GTYCANCTYG TRKGAGATCT CG                                              22

(2) INFORMATION FOR SEQ ID NO:17:

(i) SEQUENCE CHARACTERISTICS:
               (A) LENGTH: 23 base pairs
               (B) TYPE: nucleic acid
               (C) STRANDEDNESS: single
               (D) TOPOLOGY: linear (ix) FEATURE:
               (A) NAME/KEY: modified_base
               (B) LOCATION: one-of(9, 11, 14)
               (D) OTHER INFORMATION: /mod_base= OTHER
                   /note= "Y = C or T"

(ix) FEATURE:
               (A) NAME/KEY: modified_base
               (B) LOCATION: 18
               (D) OTHER INFORMATION: /mod_base= OTHER
                   /note= "R = A or G"

(ix) FEATURE:
               (A) NAME/KEY: modified_base
               (B) LOCATION: 21
               (D) OTHER INFORMATION: /mod_base= OTHER
                   /note= "H = A, C, or T"

(ix) FEATURE:
               (A) NAME/KEY: modified_base
               (B) LOCATION: 22
               (D) OTHER INFORMATION: /mod_base= OTHER
                   /note= "M = A or C"

(xi) SEQUENCE DESCRIPTION: SEQ ID NO:17:

GCTCTAGAYT TYAAYGARAT HMG                                             23

(2) INFORMATION FOR SEQ ID NO:18:

(i) SEQUENCE CHARACTERISTICS:
               (A) LENGTH: 22 base pairs
               (B) TYPE: nucleic acid
               (C) STRANDEDNESS: single
               (D) TOPOLOGY: linear (ix) FEATURE:
               (A) NAME/KEY: modified_base
               (B) LOCATION: 2
               (D) OTHER INFORMATION: /mod_base= OTHER
                   /note= "R = A or G"

(ix) FEATURE:
               (A) NAME/KEY: modified_base
               (B) LOCATION: one-of(3, 13)
               (D) OTHER INFORMATION: /mod_base= OTHER
                   /note= "N = A, C, G, or T"

(ix) FEATURE:
               (A) NAME/KEY: modified_base
               (B) LOCATION: 9
               (D) OTHER INFORMATION: /mod_base= OTHER
                   /note= "Y = C or T"

(ix) FEATURE:
               (A) NAME/KEY: modified_base
               (B) LOCATION: 14
               (D) OTHER INFORMATION: /mod_base= OTHER
                   /note= "W = A or T"
```

(xi) SEQUENCE DESCRIPTION: SEQ ID NO:18:

CRNTACTTYT ACNWCTTAAG CT                                               22

(2) INFORMATION FOR SEQ ID NO:19:

(i) SEQUENCE CHARACTERISTICS:
        (A) LENGTH: 398 base pairs
        (B) TYPE: nucleic acid
        (C) STRANDEDNESS: single
        (D) TOPOLOGY: linear (xi) SEQUENCE DESCRIPTION: SEQ ID NO:19:

AAAATTATCA TAGTCGCCAA TGACGTTACC TTCAAAGCTG GGTCTTTTGG TCCTAGAGAG      60

GACGCGTTTT TCCTCGCTGT GACTGAACCC TTGTGCGCGG AGAAGCTTCC CTTGATTTAC     120

TTAGCAGCAA ACTCTGGCGC CCGGCTAGGG GTGGCTGAAG AAGTCAAAGC CTGCTTTAAA     180

GTTGGATGGT CGGATGAAGT TTCCCCGGAG AATGGTTTTC AGTATATATA CCTAAGCCCT     240

GAGGATCACG AAAGGATTGG ATCATCTGTC ATTGCGCACG AAATAAAGCT GCCCAGCGGG     300

GAAACGAGGT GGGTCATTGA TACAATCGTT GGTAAAGAAG ATGGTATTGG CGTAGAGAAT     360

CTAACGGGAA GCGGGGCAAT AGCGGGTGCT TACTCGAG                             398

(2) INFORMATION FOR SEQ ID NO:20:

(i) SEQUENCE CHARACTERISTICS:
        (A) LENGTH: 132 amino acids
        (B) TYPE: amino acid
        (C) STRANDEDNESS:
        (D) TOPOLOGY: linear (xi) SEQUENCE DESCRIPTION: SEQ ID NO:20:

Lys Ile Ile Ile Val Ala Asn Asp Val Thr Phe Lys Ala Gly Ser Phe
    1               5                   10                  15

Gly Pro Arg Glu Asp Ala Phe Phe Leu Ala Val Thr Glu Pro Leu Cys
                20                  25                  30

Ala Glu Lys Leu Pro Leu Ile Tyr Leu Ala Ala Asn Ser Gly Ala Arg
            35                  40                  45

Leu Gly Val Ala Glu Glu Val Lys Ala Cys Phe Lys Val Gly Trp Ser
    50                  55                  60

Asp Glu Val Ser Pro Glu Asn Gly Phe Gln Tyr Ile Tyr Leu Ser Pro
    65                  70                  75                  80

Glu Asp His Glu Arg Ile Gly Ser Ser Val Ile Ala His Glu Ile Lys
                    85                  90                  95

Leu Pro Ser Gly Glu Thr Arg Trp Val Ile Asp Thr Ile Val Gly Lys
                100                 105                 110

Glu Asp Gly Ile Gly Val Glu Asn Leu Thr Gly Ser Gly Ala Ile Ala
                115                 120                 125

Gly Ala Tyr Ser
            130

(2) INFORMATION FOR SEQ ID NO:21:

(i) SEQUENCE CHARACTERISTICS:
        (A) LENGTH: 10 amino acids
        (B) TYPE: amino acid
        (C) STRANDEDNESS:
        (D) TOPOLOGY: linear (xi) SEQUENCE DESCRIPTION: SEQ ID NO:21:

Pro Leu Asp Phe Asn Glu Ile Arg Gln Leu
    1               5                   10

(2) INFORMATION FOR SEQ ID NO:22:

(i) SEQUENCE CHARACTERISTICS:
        (A) LENGTH: 7 amino acids
        (B) TYPE: amino acid
        (C) STRANDEDNESS:
        (D) TOPOLOGY: linear (xi) SEQUENCE DESCRIPTION: SEQ ID NO:22:

```
Leu Asp Phe Asn Glu Ile Arg
1               5
```

(2) INFORMATION FOR SEQ ID NO:23:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: one-of(9, 11, 14)
        (D) OTHER INFORMATION: /mod_base= OTHER
            /note= "Y = C or T"

(ix) FEATURE:
        (A) NAME/KEY: modified_base
        (B) LOCATION: 18
        (D) OTHER INFORMATION: /mod_base= OTHER
            /note= "R = A or G"

(ix) FEATURE:
        (A) NAME/KEY: modified_base
        (B) LOCATION: 21
        (D) OTHER INFORMATION: /mod_base= OTHER
            /note= "H = A, C, or T"

(ix) FEATURE:
        (A) NAME/KEY: modified_base
        (B) LOCATION: 22
        (D) OTHER INFORMATION: /mod_base= OTHER
            /note= "M = A or C"

(xi) SEQUENCE DESCRIPTION: SEQ ID NO:23:

```
GCTCTAGAYT TYAAYGARAT HMG                                              23
```

(2) INFORMATION FOR SEQ ID NO:24:

(i) SEQUENCE CHARACTERISTICS:
        (A) LENGTH: 5 amino acids
        (B) TYPE: amino acid
        (C) STRANDEDNESS:
        (D) TOPOLOGY: linear (xi) SEQUENCE DESCRIPTION: SEQ ID NO:24:

```
Asn Met Lys Met Xaa
1               5
```

(2) INFORMATION FOR SEQ ID NO:25:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 2
        (D) OTHER INFORMATION: /mod_base= OTHER
            /note= "R = A or G"

(ix) FEATURE:
            (A) NAME/KEY: modified_base
            (B) LOCATION: one-of(3, 13)
            (D) OTHER INFORMATION: /mod_base= OTHER
                /note= "N = A, C, G, or T"

(ix) FEATURE:
            (A) NAME/KEY: modified_base
            (B) LOCATION: 9
            (D) OTHER INFORMATION: /mod_base= OTHER
                /note= "Y = C or T"

(ix) FEATURE:
            (A) NAME/KEY: modified_base
            (B) LOCATION: 14
            (D) OTHER INFORMATION: /mod_base= OTHER
                /note= "W = A or T"

(xi) SEQUENCE DESCRIPTION: SEQ ID NO:25:

CRNTACTTYT ACNWCTTAAG CT                                                    22

(2) INFORMATION FOR SEQ ID NO:26:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ix) FEATURE:
            (A) NAME/KEY: modified_base
            (B) LOCATION: one-of(10, 16)
            (D) OTHER INFORMATION: /mod_base= OTHER
                /note= "N = A, C, G, or T"

(ix) FEATURE:
            (A) NAME/KEY: modified_base
            (B) LOCATION: 13
            (D) OTHER INFORMATION: /mod_base= OTHER
                /note= "R = A or G"

(ix) FEATURE:
            (A) NAME/KEY: modified_base
            (B) LOCATION: one-of(14, 19)
            (D) OTHER INFORMATION: /mod_base= OTHER
                /note= "Y = C or T"

(xi) SEQUENCE DESCRIPTION: SEQ ID NO:26:

GCTCTAGACN CARYTNAAYT T                                                     21

(2) INFORMATION FOR SEQ ID NO:27:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ix) FEATURE:
            (A) NAME/KEY: modified_base
            (B) LOCATION: 2
            (D) OTHER INFORMATION: /mod_base= OTHER
                /note= "R = A or G"

(ix) FEATURE:
            (A) NAME/KEY: modified_base
            (B) LOCATION: one-of(3, 13)
            (D) OTHER INFORMATION: /mod_base= OTHER
                /note= "N = A, C, G, or T"

(ix) FEATURE:
            (A) NAME/KEY: modified_base
            (B) LOCATION: 9
            (D) OTHER INFORMATION: /mod_base= OTHER
                /note= "Y = C or T"

```
    (ix) FEATURE:
          (A) NAME/KEY: modified_base
          (B) LOCATION: 14
          (D) OTHER INFORMATION: /mod_base= OTHER
              /note= "W = A or T"

(xi) SEQUENCE DESCRIPTION: SEQ ID NO:27:

CRNTACTTYG ACNWCTTAAG CT                                                    22

(2) INFORMATION FOR SEQ ID NO:28:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (xi) SEQUENCE DESCRIPTION: SEQ ID NO:28:

GAAGATCTTT ATGGGCGGTA GTATG                                                 25

(2) INFORMATION FOR SEQ ID NO:29:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (xi) SEQUENCE DESCRIPTION: SEQ ID NO:29:

GGTCGAAACG GTACAACCTA GGC                                                   23

(2) INFORMATION FOR SEQ ID NO:30:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (xi) SEQUENCE DESCRIPTION: SEQ ID NO:30:

GGGGCAAUAA UGGTGGAATC TG                                                    22

(2) INFORMATION FOR SEQ ID NO:31:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (xi) SEQUENCE DESCRIPTION: SEQ ID NO:31:

CTTGGUUGAU GACTG                                                            15
```